US009783613B2

(12) United States Patent
Karagiannis et al.

(10) Patent No.: US 9,783,613 B2
(45) Date of Patent: Oct. 10, 2017

(54) IGE ANTI-HMW-MAA ANTIBODY

(75) Inventors: Sophia Karagiannis, London (GB); Andrew Beavil, London (GB); Frank Nestle, London (GB)

(73) Assignee: IGEM Therapeutics Limited, Reading (GB)

( * ) Notice: Subject to any disclaimer, the term of this patent is extended or adjusted under 35 U.S.C. 154(b) by 92 days.

(21) Appl. No.: 14/348,997

(22) PCT Filed: Oct. 4, 2011

(86) PCT No.: PCT/GB2011/051884

§ 371 (c)(1), (2), (4) Date: Jul. 8, 2014

(87) PCT Pub. No.: WO2013/050725

PCT Pub. Date: Apr. 11, 2013

(65) Prior Publication Data

US 2014/0322246 A1 Oct. 30, 2014

(51) Int. Cl.

*C07K 16/30* (2006.01)
*A61K 47/48* (2006.01)
*A61K 39/00* (2006.01)

(52) U.S. Cl.

CPC .... *C07K 16/3053* (2013.01); *A61K 47/48623* (2013.01); *A61K 2039/505* (2013.01); *C07K 2317/24* (2013.01); *C07K 2317/52* (2013.01); *C07K 2317/732* (2013.01)

(58) Field of Classification Search

None

See application file for complete search history.

(56) References Cited

U.S. PATENT DOCUMENTS 5,866,124 A * 2/1999 Hardman ........... C07K 16/4266 424/131.1
2003/0059763 A1* 3/2003 Saxon ................ C12N 15/1034 435/4

FOREIGN PATENT DOCUMENTS

WO WO 2006/100582 * 9/2006
WO 2008/030625 3/2008

OTHER PUBLICATIONS

Paul, Fundamental Immunology, 3rd Edition, 1993, pp. 292-295.*
Rudikoff et al Proc. Natl. Acad. Sci. USA 1982 vol. 79: p. 1979.*
Casset et al BBRC 307, 198-205 2003.*
Pascalis et al The Journal of Immunology vol. 169, 3076-3084, 2002.*
Karaglannis et al, British Associated of Dermatologist 2011, p. 164 abstract: p14, IDS, # 4, filed on Apr. 23, 2014.*
Karagiannis et al, J Immuno 179:2832-43, published 2007, IDS #1 filed on Apr. 23, 2014.*
International Search Report and Written Opinion for PCT/GB2011/051884 dated May 31, 2012.
Karagiannis et al., "IgE-antibody-dependent immunotherapy of solid tumors: Cytotoxic and phagocytic mechanisms of eradiction of ovarian cancer cells," The Journal of Immunology, 179(5): 2832-2843 (2007).
Karagiannis et al., "Antibodies of the IgG and IgE classes against the melanoma-associated antigen HMW-MAA: Investigating a new therapeutic approach," rackcdn.com (Mar. 1, 2012), Retrieved from the internet: URL:http://c953383183.r83.cf2.rackcdn.com/file_attachment/attachments/8663/originalf90c554e2d5d9d48ce77cbd547475692.html? 1330573647 (retrieved on May 11, 2012).
Karagiannis et al., "IgE antibodies targeting a major melanoma antigen are more effective than IgG antibodies for tumour protection in a humanized melanoma model," British Journal of Dermatology, 166(4): E20 (2012), Annual Meeting of the British Society for Investigative Dermatology, Exeter, UK, Apr. 16-18, 2012.
Karagiannis et al., "Investigating anti-HMW-MAA IgG and anti-HMW-MAA IgE antibodies: a new approach in immunotherapy of melanoma," British Journal of Dermatology, 164(4): 922 (2011), Annual Meeting of the British Society for Investigative Dermatology, Manchester, UK, Apr. 11-13, 2011.
Josephs et al., "IgE immunotherapy of solid tumours: a novel model targeting folate receptor alpha-positive carcinomas with MOv18 IgE," British Journal of Dermatology, 162(4): 946-947 (2010) and Annual Meeting of the British Society for Investigative Dermatology, Edinburgh, UK; Apr. 12-14, 2010.
Rudman et al., "Harnessing engineered antibodies of the IgE class to combat malignancy: initial assessment of Fc•RI-mediated basophil activation by a tumour-specific IgE antibody to evaluate the risk of type I hypersensitivity," Clinical and Experimental Allergy: Journal of the British Society for Allergy and Clinical Immunology, 41(10): 1400-1413 (2011).
International Preliminary Report on Patentability; International Application No. PCT/GB2011/051884.
Karagiannis et al.,"IgE Interacts with Potent Effector Cells Against Tumors: ADCC and ADCP," Chapter 8 of Cancer and IgE: Introducing the Concept of AllergoOncology, pp. 185-213, Humana Press, Editors: Penichet and Jensen-Jarolim (2010).

* cited by examiner

*Primary Examiner* — Lei Yao

(74) *Attorney, Agent, or Firm* — Morgan, Lewis & Bockius LLP

(57) ABSTRACT

In one aspect, there is provided an antibody or a functional fragment thereof, wherein the antibody or functional fragment thereof is capable of binding specifically to high molecular weight melanoma associated antigen (HMW-MAA), and binding to an Fcε receptor.

12 Claims, 22 Drawing Sheets

SEQ ID NO:1

```
   1 MQSGPRPPLP APGLALALTL TMLARLASAA SFFGENHLEV PVATALTDID LQLQFSTSQP
  61 EALLLLAAGP ADHLLLQLYS GRLQVRLVLG QEELRLQTPA ETLLSDSIPH TVVLTVVEGW
 121 ATLSVDGFLN ASSAVPGAPL EVPYGLFVGG TGTLGLPYLR GTSRPLRGCL HAATLNGRSL
 181 LRPLTPDVHE GCAEEFSASD DVALGFSGPH SLAAFPAWGT QDEGTLEFTL TTQSRQAPLA
 241 FQAGGRRGDF IYVDIFEGHL RAVVEKGQGT VLLHNSVPVA DGQPHEVSVH INAHRLEISV
 301 DQYPTHTSNR GVLSYLEPRG SLLLGGLDAE ASRHLQEHRL GLTPEATNAS LLGCMEDLSV
 361 NGQRRGLREA LLTRNMAAGC RLEEEEYEDD AYGHYEAFST LAPEAWPAME LPEPCVPEPG
 421 LPPVFANFTQ LLTISPLVVA EGGTAWLEWR HVQPTLDLME AELRKSQVLF SVTRGARHGE
 481 LELDIPGAQA RKMFTLLDVV NRKARFIHDG SEDTSDQLVL EVSVTARVPM PSCLRRGQTY
 541 LLPIQVNPVN DPPHIIFPHG SLMVILEHTQ KPLGPEVFQA YDPDSACEGL TFQVLGTSSG
 601 LPVERRDQPG EPATEFSCRE LEAGSLVYVH RGGPAQDLTF RVSDGLQASP PATLKVVAIR
 661 PAIQIHRSTG LRLAQGSAMP ILPANLSVET NAVGQDVSVL FRVTGALQFG ELQKQGAGGV
 721 EGAEWWATQA FHQRDVEQGR VRYLSTDPQH HAYDTVENLA LEVQVGQEIL SNLSFPVTIQ
 781 RATVWMLRLE PLHTQNTQQE TLTTAHLEAT LEEAGPSPPT FHYEVVQAPR KGNLQLQGTR
 841 LSDGQGFTQD DIQAGRVTYG ATARASEAVE DTFRFRVTAP PYFSPLYTFP IHIGGDPDAP
 901 VLTNVLLVVP EGGEGVLSAD HLFVKSLNSA SYLYEVMERP RHGRLAWRGT QDKTTMVTSF
 961 TNEDLLRGRL VYQHDDSETT EDDIPFVATR QGESSGDMAW EEVRGVFRVA IQPVNDHAPV
1021 QTISRIFHVA RGGRRLLTTD DVAFSDADSG FADAQLVLTR KDLLFGSIVA VDEPTRPIYR
1081 FTQEDLRKRR VLFVHSGADR GWIQLQVSDG QHQATALLEV QASEPYLRVA NGSSLVVPQG
1141 GQGTIDTAVL HLDTNLDIRS GDEVHYHVTA GPRWGQLVRA GQPATAFSQQ DLLDGAVLYS
1201 HNGSLSPRDT MAFSVEAGPV HTDATLQVTI ALEGPLAPLK LVRHKKIYVF QGEAAEIRRD
1261 QLEAAQEAVP PADIVFSVKS PPSAGYLVMV SRGALADEPP SLDPVQSFSQ EAVDTGRVLY
1321 LHSRPEAWSD AFSLDVASGL GAPLEGVLVE LEVLPAAIPL EAQNFSVPEG GSLTLAPPLL
1381 RVSGPYFPTL LGLSLQVLEP PQHGALQKED GPQARTLSAF SWRMVEEQLI RYVHDGSETL
1441 TDSFVLMANA SEMDRQSHPV AFTVTVLPVN DQPPILTTNT GLQMWEGATA PIPAEALRST
1501 DGDSGSEDLV YTIEQPSNGR VVLRGAPGTE VRSFTQAQLD GGLVLFSHRG TLDGGFRFRL
1561 SDGEHTSPGH FFRVTAQKQV LLSLKGSQTL TVCPGSVQPL SSQTLRASSS AGTDPQLLLY
1621 RVVRGPQLGR LFHAQQDSTG EALVNFTQAE VYAGNILYEH EMPPEPFWEA HDTLELQLSS
1681 PPARDVAATL AVAVSFEAAC PQRPSHLWKN KGLWVPEGQR ARITVAALDA SNLLASVPSP
1741 QRSEHDVLFQ VTQFPSRGQL LVSEEPLHAG QPHFLQSQLA AGQLVYAHGG GGTQQDGFHF
1801 RAHLQGPAGA SVAGPQTSEA FAITVRDVNE RPPQPQASVP LRLTRGSRAP ISRAQLSVVD
1861 PDSAPGEIEY EVQRAPHNGF LSLVGGGLGP VTRFTQADVD SGRLAFVANG SSVAGIFQLS
1921 MSDGASPPLP MSLAVDILPS AIEVQLRAPL EVPQALGRSS LSQQQLRVVS DREEPEAAYR
1981 LIQGPQYGHL LVGGRPTSAF SQFQIDQGEV VFAFTNFSSS HDHFRVLALA RGVNASAVVN
2041 VTVRALLHVW AGGPWPQGAT LRLDPTVLDA GELANRTGSV PRFRLLEGPR HGRVVRVPRA
2101 RTEPGGSQLV EQFTQQDLED GRLGLEVGRP EGRAPGPAGD SLTLELWAQG VPPAVASLDF
2161 ATEPYNAARP YSVALLSVPE AARTEAGKPE SSTPTGEPGP MASSPEPAVA KGGFLSFLEA
2221 NMFSVIIPMC LVLLLLALIL PLLFYLRKRN KTGKHDVQVL TAKPRNGLAG DTETFRKVEP
2281 GQAIPLTAVP GQGPPPGGQP DPELLQFCRT PNPALKNGQY WV
```

FIG. 10

SEQ ID NO:2

```
   1 atgcagtccg ggccgcggcc cccacttcca gcccccggcc tggccttggc tttgaccctg
  61 actatgttgg ccagacttgc atccgcggct tccttcttcg gtgagaacca cctggaggtg
 121 cctgtggcca cggctctgac cgacatagac ctgcagctgc agttctccac gtcccagccc
 181 gaagccctcc ttctcctggc agcaggccca gctgaccacc tcctgctgca gctctactct
 241 ggacgcctgc aggtcagact tgttctgggc caggaggagc tgaggctgca gactccagca
 301 gagacgctgc tgagtgactc catcccccac actgtggtgc tgactgtcgt agagggctgg
 361 gccacgttgt cagtcgatgg gtttctgaac gcctcctcag cagtcccagg agccccccta
 421 gaggtcccct atgggctctt tgttgggggc actgggaccc ttggcctgcc ctacctgagg
 481 ggaaccagcc gacccctgag ggggttgcctc catgcagcca ccctcaatgg ccgcagcctc
 541 ctccggcctc tgacccccga tgtgcatgag ggctgtgctg aagagttttc tgccagtgat
 601 gatgtggccc tgggcttctc tgggccccac tctctggctg ccttccctgc ctggggcact
 661 caggacgaag gaaccctaga gtttacactc accacacaga gccggcaggc acccttggcc
 721 ttccaggcag gggccggcg tggggacttc atctatgtgg acatatttga gggccacctg
 781 cgggccgtgg tggagaaggg ccagggtacc gtattgctcc acaacagtgt gcctgtggcc
 841 gatgggcagc cccatgaggt cagtgtccac atcaatgctc accggctgga aatctccgtg
 901 gaccagtacc ctacgcatac ttcgaaccga ggagtcctca gctacctgga gccacggggc
 961 agtctccttc tcggggggct ggatgcagag gcctctcgtc acctccagga acaccgcctg
1021 ggcctgacac cagaggccac caatgcctcc ctgctgggct gcatggaaga cctcagtgtc
1081 aatggccaga ggcgggggct gcgggaagct ttgctgacgc gcaacatggc agccggctgc
1141 aggctggagg aggaggagta tgaggacgat gcctatggac attatgaagc tttctccacc
1201 ctggcccctg aggcttggcc agccatggag ctgcctgagc catgcgtgcc tgagccaggg
1261 ctgcctcctg tctttgccaa tttcacccag ctgctgacta tcagcccact ggtggtggcc
1321 gagggggca cagcctggct tgagtggagg catgtgcagc ccacgctgga cctgatggag
1381 gctgagctgc gcaaatccca ggtgctgttc agcgtgaccc gaggggcacg ccatggcgag
1441 ctcgagctgg acatcccggg agcccaggca cgaaaaatgt tcaccctcct ggacgtggtg
1501 aaccgcaagg cccgcttcat ccacgatggc tctgaggaca cctccgacca gctggtgctg
1561 gaggtgtcgg tgacggctcg ggtgcccatg ccctcatgcc ttcggagggg ccaaacatac
1621 ctcctgccca tccaggtcaa ccctgtcaat gacccacccc acatcatctt cccacatggc
1681 agcctcatgg tgatcctgga acacacgcag aagccgctgg ggcctgaggt tttccaggcc
1741 tatgacccgg actctgcctg tgagggcctc accttccagg tccttggcac ctcctctggc
1801 ctccccgtgg agcgccgaga ccagcctggg gagccggcga ccgagttctc ctgccgggag
1861 ttggaggccg gcagcctagt ctatgtccac cgcggtggtc ctgcacagga cttgacgttc
1921 cgggtcagcg atggactgca ggccagcccc ccggccacgc tgaaggtggt ggccatccgg
1981 ccggccatac agatccaccg cagcacaggg ttgcgactgg cccaaggctc tgccatgccc
2041 atcttgcccg ccaacctgtc ggtggagacc aatgccgtgg ggcaggatgt gagcgtgctg
2101 ttccgcgtca ctggggccct gcagtttggg gagctgcaga agcagggggc aggtggggtg
2161 gagggtgctg agtggtgggc cacacaggcg ttccaccagc gggatgtgga gcagggccgc
2221 gtgaggtacc tgagcactga cccacagcac cacgcttacg acaccgtgga gaacctggcc
2281 ctggaggtgc aggtgggcca ggagatcctg agcaatctgt ccttcccagt gaccatccag
2341 agagccactg tgtggatgct gcggctggag ccactgcaca ctcagaacac ccagcaggag
2401 accctcacca cagcccacct ggaggccacc ctggaggagg caggcccaag ccccccaacc
```

FIG. 11 (continued)

```
2461 ttccattatg aggtggttca ggctcccagg aaaggcaacc ttcaactaca gggcacaagg
2521 ctgtcagatg gccagggctt cacccaggat gacatacagg ctggccgggt gacctatggg
2581 gccacagcac gtgcctcaga ggcagtcgag gacaccttcc gtttccgtgt cacagctcca
2641 ccatatttct ccccactcta taccttcccc atccacattg gtggtgaccc agatgcgcct
2701 gtcctcacca atgtcctcct cgtggtgcct gagggtggtg agggtgtcct ctctgctgac
2761 cacctctttg tcaagagtct caacagtgcc agctacctct atgaggtcat ggagcggccc
2821 cgccatggga ggttggcttg gcgtgggaca caggacaaga ccactatggt gacatccttc
2881 accaatgaag acctgttgcg tggccggctg gtctaccagc atgatgactc cgagaccaca
2941 gaagatgata tcccatttgt tgctacccgc cagggcgaga gcagtggtga catggcctgg
3001 gaggaggtac ggggtgtctt ccgagtggcc atccagcccg tgaatgacca cgcccctgtg
3061 cagaccatca gccggatctt ccatgtggcc cggggtgggc ggcggctgct gactacagac
3121 gacgtggcct tcagcgatgc tgactcgggc tttgctgacg cccagctggt gcttacccgc
3181 aaggacctcc tctttggcag tatcgtggcc gtagatgagc ccacgcggcc catctaccgc
3241 ttcacccagg aggacctcag gaagaggcga gtactgttcg tgcactcagg ggctgaccgt
3301 ggctggatcc agctgcaggt gtccgacggg caacaccagg ccactgcgct gctggaggtg
3361 caggcctcgg aaccctacct ccgtgtggcc aacggctcca gccttgtggt ccctcaagga
3421 ggccagggca ccatcgacac ggccgtgctc cacctggaca ccaacctcga catccgcagt
3481 ggggatgagg tccactacca cgtcacagct ggccctcgct ggggacagct agtccgggct
3541 ggtcagccag ccacagcctt ctcccagcag gacctgctgg atggggccgt tctctatagc
3601 cacaatggca gcctcagccc ccgcgacacc atggccttct ccgtggaagc agggccagtg
3661 cacacggatg ccaccctaca agtgaccatt gccctagagg gcccactggc cccactgaag
3721 ctggtccggc acaagaagat ctacgtcttc cagggagagg cagctgagat cagaagggac
3781 cagctggagg cagcccagga ggcagtgcca cctgcagaca tcgtattctc agtgaagagc
3841 ccaccgagtg ccggctacct ggtgatggtg tcgcgtggcg ccttggcaga tgagccaccc
3901 agcctggacc ctgtgcagag cttctcccag gaggcagtgg acacaggcag ggtcctgtac
3961 ctgcactccc gccctgaggc ctggagcgat gccttctcgc tggatgtggc ctcaggcctg
4021 ggtgctcccc tcgagggcgt ccttgtggag ctggaggtgc tgcccgctgc catcccacta
4081 gaggcgcaaa acttcagcgt ccctgagggt ggcagcctca ccctggcccc tccactgctc
4141 cgtgtctccg ggccctactt ccccactctc ctgggcctca gcctgcaggt gctggagcca
4201 ccccagcatg gagccctgca gaaggaggac ggacctcaag ccaggaccct cagcgccttc
4261 tcctggagaa tggtggaaga gcagctgatc cgctacgtgc atgacgggag cgagacactg
4321 acagacagtt ttgtcctgat ggctaatgcc tccgagatgg atcgccagag ccatcctgtg
4381 gccttcactg tcactgtcct gcctgtcaat gaccaacccc ccatcctcac tacaaacaca
4441 ggcctgcaga tgtgggaggg ggccactgcg cccatccctg cggaggctct gaggagcacg
4501 gacggcgact ctgggtctga ggatctggtc tacaccatcg agcagcccag caacgggcgg
4561 gtagtgctgc gggggcgcc gggcactgag gtgcgcagct tcacgcaggc ccagctggac
4621 ggcgggctcg tgctgttctc acacagagga accctggatg gaggcttccg cttccgcctc
4681 tctgacggcg agcacacttc ccccggacac ttcttccgag tgacggccca gaagcaagtg
4741 ctcctctcgc tgaagggcag ccagacactg actgtctgcc cagggtccgt ccagccactc
4801 agcagtcaga ccctcagggc cagctccagc gcaggcactg acccccagct cctgctctac
4861 cgtgtggtgc ggggccccca gctaggccgg ctgttccacg cccagcagga cagcacaggg
4921 gaggccctgg tgaacttcac tcaggcagag gtctacgctg ggaatattct gtatgagcat
4981 gagatgcccc ccgagccctt ttgggaggcc catgataccc tagagctcca gctgtcctcg
5041 ccgcctgccc gggacgtggc cgccaccctt gctgtggctg tgtcttttga ggctgcctgt
```

FIG. 11 (continued)

```
5101 ccccagcgcc ccagccacct ctggaagaac aaaggtctct gggtccccga gggccagcgg
5161 gccaggatca ccgtggctgc tctggatgcc tccaatctct tggccagcgt tccatcaccc
5221 cagcgctcag agcatgatgt gctcttccag gtcacacagt tccccagccg gggccagctg
5281 ttggtgtccg aggagcccct ccatgctggg cagcccccact tcctgcagtc ccagctggct
5341 gcagggcagc tagtgtatgc ccacggcggt gggggcaccc agcaggatgg cttccacttt
5401 cgtgcccacc tccaggggcc agcaggggcc tccgtggctg gaccccaaac ctcagaggcc
5461 tttgccatca cggtgaggga tgtaaatgag cggccccctc agccacaggc ctctgtccca
5521 ctccggctca cccgaggctc tcgtgccccc atctcccggg cccagctgag tgtggtggac
5581 ccagactcag ctcctgggga gattgagtac gaggtccagc gggcacccca caacggcttc
5641 ctcagcctgg tgggtggtgg cctggggccc gtgacccgct tcacgcaagc cgatgtggat
5701 tcagggcggc tggccttcgt ggccaacggg agcagcgtgg caggcatctt ccagctgagc
5761 atgtctgatg ggccagccc accccctgcc atgtccctgg ctgtggacat cctaccatcc
5821 gccatcgagg tgcagctgcg ggcaccccctg gaggtgcccc aagctttggg gcgctcctca
5881 ctgagccagc agcagctccg ggtggtttca gatcgggagg agccagaggc agcataccgc
5941 ctcatccagg gaccccagta tgggcatctc ctggtgggcg ggcggcccac ctcggccttc
6001 agccaattcc agatagacca gggcgaggtg gtctttgcct tcaccaactt ctcctcctct
6061 catgaccact tcagagtcct ggcactggct aggggtgtca atgcatcagc cgtagtgaac
6121 gtcactgtga gggctctgct gcatgtgtgg gcaggtgggc catggcccca gggtgccacc
6181 ctgcgcctgg accccaccgt cctagatgct ggcgagctgg ccaaccgcac aggcagtgtg
6241 ccgcgcttcc gcctcctgga gggaccccgg catggccgcg tggtccgcgt gccccgagcc
6301 aggacggagc ccgggggcag ccagctggtg gagcagttca ctcagcagga ccttgaggac
6361 gggaggctgg ggctggaggt gggcaggcca gaggggaggg cccccggccc cgcaggtgac
6421 agtctcactc tggagctgtg ggcacagggc gtcccgcctg ctgtggcctc cctggacttt
6481 gccactgagc cttacaatgc tgcccggccc tacagcgtgg ccctgctcag tgtccccgag
6541 gccgcccgga cggaagcagg gaagccagag agcagcaccc ccacaggcga gccaggcccc
6601 atggcatcca gccctgagcc cgctgtggcc aagggaggct tcctgagctt ccttgaggcc
6661 aacatgttca gcgtcatcat ccccatgtgc ctggtacttc tgctcctggc gctcatcctg
6721 cccctgctct tctacctccg aaaacgcaac aagacgggca agcatgacgt ccaggtcctg
6781 actgccaagc cccgcaacgg cctggctggt gacaccgaga cctttcgcaa ggtggagcca
6841 ggccaggcca tcccgctcac agctgtgcct ggccaggggc cccctccagg aggccagcct
6901 gacccagagc tgctgcagtt ctgccggaca cccaaccctg cccttaagaa tggccagtac
6961 tgggtgtga
```

FIG. 11 (continued)

SEQ ID NO:3

GCCATGGCCCAGGTGAAGCTGCAGCAGTCAGGAGGGGGCTTGGTGCAACCTG
GAGGATCCATGAAACTCTCCTGTGTTGTCTCTGGATTCACTTTCAGTAATTACT
GGATGAACTGGGTCCGCCAGTCTCCAGAGAAGGGGCTTGAGTGGATTGCAGA
AATTAGATTGAAATCCAATAATTTTGGAAGATATTATGCGGAGTCTGTGAAAG
GGAGGTTCACCATCTCAAGAGATGATTCCAAAAGTAGTGCCTACCTGCAAATG
ATCAACCTAAGAGCTGAAGATACTGGCATTTATTACTGTACCAGTTATGGTAA
CTACGTTGGGCACTATTTTGACCACTGGGGCCAAGGGACCACGGTCACCGTCT
CGAGT

FIG. 12

SEQ ID NO:4

AMAQVKLQQSGGGLVQPGGSMKLSCVVSGFTFSNYWMNWVRQSPEKGLEWIA
EIRLKSNNFGRYYAESVKGRFTISRDDSKSSAYLQMINLRAEDTGIYYCTSYGNYV
GHYFDHWGQGTTVTVSS

FIG. 13

SEQ ID NO:5

GATATCGAGCTCACCCAATCTCCAAAATTCATGTCCACATCAGTAGGAGACAG
GGTCAGCGTCACCTGCAAGGCCAGTCAGAATGTGGATACTAATGTAGCGTGGT
ATCAACAAAAACCAGGGCAATCTCCTGAACCACTGCTTTTCTCGGCATCCTAC
CGTTACACTGGAGTCCCTGATCGCTTCACAGGCAGTGGATCTGGGACAGATTT
CACTCTCACCATCAGCAATGTGCAGTCTGAAGACTTGGCAGAGTATTTCTGTC
AGCAATATAACAGCTATCCTCTGACGTTCGGTGGCGGCACCAAGCTGGAAATC
AAACGGGCGGCCGCAGAA

FIG. 14

SEQ ID NO:6

DIELTQSPKFMSTSVGDRVSVTCKASQNVDTNVAWYQQKPGQSPEPLLFSASYRY
TGVPDRFTGSGSGTDFTLTISNVQSEDLAEYFCQQYNSYPLTFGGGTKLEIKRAAA
E

FIG. 15

SEQ ID NO:7

QVKLQQSGGGLVQPGGSMKLSCVVSGFTFSNYWMNWVRQSPEKGLEWIAE
IRLKSNNFGRYYAESVKGRFTISRDDSKSSAYLQMINLRAEDTGIYYCTSYGN
YVGHYFDHWGQGTTVTVSSA<u>STQSPSVFPLTRCCKNIPSNATSVTLGCLATGYF</u>
<u>PEPVMVTWDTGSLNGTTMTLPATTLTLSGHYATISLLTVSGAWAKQMFTCRVAH</u>
<u>TPSSTDWVDNKTFSVCSRDFTPPTVKILQSSCDGGGHFPPTIQLLCLVSGYTPGTINI</u>
<u>TWLEDGQVMDVDLSTASTTQEGELASTQSELTLSQKHWLSDRTYTCQVTYQGHT</u>
<u>FEDSTKKCADSNPRGVSAYLSRPSPFDLFIRKSPTITCLVVDLAPSKGTVNLTWSR</u>
<u>ASGKPVNHSTRKEEKQRNGTLTVTSTLPVGTRDWIEGETYQCRVTHPHLPRALM</u>
<u>RSTTKTSGPRAAPEVYAFATPEWPGSRDKRTLACLIQNFMPEDISVQWLHNEVQL</u>
<u>PDARHSTTQPRKTKGSGFFVFSRLEVTRAEWEQKDEFICRAVHEAASPSQTV</u>
<u>QRAVSVNPGK</u>

FIG. 16

SEQ ID NO:8

DIELTQSPKFMSTSVGDRVSVTCKASQNVDTNVAWYQQKPGQSPEPLLFSAS
YRYTGVPDRFTGSGSGTDFTLTISNVQSEDLAEYFCQQYNSYPLTFGGGTKLE
IKR<u>TVAAPSVFIFPPSDEQLKSGTASVVCLLNNFYPREAKVQWKVDNALQSGNSQ</u>
<u>ESVTEQDSKDSTYSLSSTLT LSKADYEKHKVYACEVTHQGLSSPVTKSFNRGEC</u>

FIG. 17

SEQ ID NO:9

CAAGTCAAACTGCAGCAGAGCGGTGGAGGCCTGGTGCAGCCTGGTGGCA
GCATGAAGCTGAGCTGCGTCGTGAGCGGCTTCACCTTCAGCAACTACTGG
ATGAACTGGGTCCGGCAGAGCCCCGAGAAGGGCCTGGAATGGATCGCCG
AGATCCGGCTGAAAAGCAACAACTTCGGCCGGTACTACGCCGAGAGCGT
GAAGGGCCGGTTCACCATCAGCCGGGACGACAGCAAGAGCAGCGCCTAC
CTGCAGATGATCAACCTGCGGGCCGAGGACACCGGCATCTACTACTGCA
CCAGCTACGGCAACTACGTGGGCCACTACTTCGACCACTGGGGCCAGGG
CACCACCGTGACTGTCAGCAGCGCTAGCACACAGAGCCCATCCGTCTTCCC
CTTGACCCGCTGCTGCAAAAACATTCCCTCCAATGCCACCTCCGTGACTCTGG
GCTGCCTGGCCACGGGCTACTTCCCGGAGCCGGTGATGGTGACCTGGGACACA
GGCTCCCTCAACGGGACAACTATGACCTTACCAGCCACCACCCTCACGCTCTC
TGGTCACTATGCCACCATCAGCTTGCTGACCGTCTCGGGTGCGTGGGCCAAGC
AGATGTTCACCTGCCGTGTGGCACACACTCCATCGTCCACAGACTGGGTCGAC
AACAAAACCTTCAGCGTCTGCTCCAGGGACTTCACCCCGCCCACCGTGAAGAT
CTTACAGTCGTCCTGCGACGGCGGCGGGCACTTCCCCCCGACCATCCAGCTCC
TGTGCCTCGTCTCTGGGTACACCCCAGGGACTATCAACATCACCTGGCTGGAG
GACGGGCAGGTCATGGACGTGGACTTGTCCACCGCCTCTACCACGCAGGAGG
GTGAGCTGGCCTCCACACAAAGCGAGCTCACCCTCAGCCAGAAGCACTGGCT
GTCAGACCGCACCTACACCTGCCAGGTCACCTATCAAGGTCACACCTTTGAGG
ACAGCACCAAGAAGTGTGCAGATTCCAACCCGAGAGGGGTGAGCGCCTACCT
AAGCCGGCCCAGCCCGTTCGACCTGTTCATCCGCAAGTCGCCCACGATCACCT
GTCTGGTGGTGGACCTGGCACCCAGCAAGGGGACCGTGAACCTGACCTGGTC
CCGGGCCAGTGGGAAGCCTGTGAACCACTCCACCAGAAAGGAGGAGAAGCAG
CGCAATGGCACGTTAACCGTCACGTCCACCCTGCCGGTGGGCACCCGAGACTG
GATCGAGGGGGAGACCTACCAGTGCAGGGTGACCCACCCCCACCTGCCCAGG
GCCCTCATGCGGTCCACGACCAAGACCAGCGGCCCGCGTGCTGCCCCGGAAG
TCTATGCGTTTGCGACGCCGGAGTGGCCGGGGAGCCGGGACAAGCGCACCCT
CGCCTGCCTGATCCAGAACTTCATGCCTGAGGACATCTCGGTGCAGTGGCTGC
ACAACGAGGTGCAGCTCCCGGACGCCCGGCACAGCACGACGCAGCCCCGCAA
GACCAAGGGCTCCGGCTTCTTCGTCTTCAGCCGCCTGGAGGTGACCAGGGCCG
AATGGGAGCAGAAAGATGAGTTCATCTGCCGTGCAGTCCATGAGGCAGCGAG
CCCCTCACAGACCGTCCAGCGAGCGGTGTCTGTAAATCCCGGTAAATGA

FIG. 18

SEQ ID NO:10

GACATCGAGCTGACCCAGAGCCCCAAGTTCATGAGCACCAGCGTGGGCG
ACAGAGTGTCCGTGACCTGCAAGGCCAGCCAGAACGTGGACACCAACGT
GGCCTGGTATCAGCAGAAGCCCGGCCAGAGCCCTGAGCCTCTGCTGTTC
AGCGCCAGCTACAGATACACCGGCGTGCCCGACAGATTCACAGGCAGCG
GCTCCGGCACCGACTTCACCCTGACCATCAGCAACGTGCAGAGCGAGGA
CCTGGCCGAGTACTTCTGCCAGCAGTACAACAGCTACCCCCTGACCTTCG
GCGGAGGCACCAAGCTGGAAATCAAGCGTACGGTGGCGGCGCCATCTGTCT
TCATCTTCCCGCCATCTGATGAGCAGTTGAAATCTGGAACTGCCTCTGTTGTGT
GCCTGCTGAATAACTTCTATCCCAGAGAGGCCAAAGTACAGTGGAAGGTGGA
TAACGCCCTCCAATCGGGTAACTCCCAGGAGAGTGTCACAGAGCAGGACAGC
AAGGACAGCACCTACAGCCTCAGCAGCACCCTGACGCTGAGCAAAGCAGACT
ACGAGAAACACAAAGTCTACGCCTGCGAAGTCACCCATCAGGGCCTGAGCTC
GCCCGTCACAAAGAGCTTCAACAGGGGAGAGTGTTAG

FIG. 19

SEQ ID NO:11

CAAGTCAAACTGCAGCAGAGCGGTGGAGGCCTGGTGCAGCCTGGTGGCAGCA
TGAAGCTGAGCTGCGTCGTGAGCGGCTTCACCTTCAGCAACTACTGGATGAAC
TGGGTCCGGCAGAGCCCCGAGAAGGGCCTGGAATGGATCGCCGAGATCCGGC
TGAAAAGCAACAACTTCGGCCGGTACTACGCCGAGAGCGTGAAGGGCCGGTT
CACCATCAGCCGGGACGACAGCAAGAGCAGCGCCTACCTGCAGATGATCAAC
CTGCGGGCCGAGGACACCGGCATCTACTACTGCACCAGCTACGGCAACTACGT
GGGCCACTACTTCGACCACTGGGGCCAGGGCACCACCGTGACTGTCAGCAGC
G

FIG. 20

SEQ ID NO:12

GACATCGAGCTGACCCAGAGCCCCAAGTTCATGAGCACCAGCGTGGGCGACA
GAGTGTCCGTGACCTGCAAGGCCAGCCAGAACGTGGACACCAACGTGGCCTG
GTATCAGCAGAAGCCCGGCCAGAGCCCTGAGCCTCTGCTGTTCAGCGCCAGCT
ACAGATACACCGGCGTGCCCGACAGATTCACAGGCAGCGGCTCCGGCACCGA
CTTCACCCTGACCATCAGCAACGTGCAGAGCGAGGACCTGGCCGAGTACTTCT
GCCAGCAGTACAACAGCTACCCCCTGACCTTCGGCGGAGGCACCAAGCTGGA
AATCAAGC

FIG. 21

SEQ ID NO:13

CTAGCACACAGAGCCCATCCGTCTTCCCCTTGACCCGCTGCTGCAAAAAC
ATTCCCTCCAATGCCACCTCCGTGACTCTGGGCTGCCTGGCCACGGGCTA
CTTCCCGGAGCCGGTGATGGTGACCTGGGACACAGGCTCCCTCAACGGG
ACAACTATGACCTTACCAGCCACCACCCTCACGCTCTCTGGTCACTATGC
CACCATCAGCTTGCTGACCGTCTCGGGTGCGTGGGCCAAGCAGATGTTCA
CCTGCCGTGTGGCACACACTCCATCGTCCACAGACTGGGTCGACAACAAA
ACCTTCAGCG

FIG. 22A

SEQ ID NO:14

TCTGCTCCAGGGACTTCACCCCGCCCACCGTGAAGATCTTACAGTCGTCC
TGCGACGGCGGCGGGCACTTCCCCCCGACCATCCAGCTCCTGTGCCTCG
TCTCTGGGTACACCCCAGGGACTATCAACATCACCTGGCTGGAGGACGG
GCAGGTCATGGACGTGGACTTGTCCACCGCCTCTACCACGCAGGAGGGT
GAGCTGGCCTCCACACAAAGCGAGCTCACCCTCAGCCAGAAGCACTGGC
TGTCAGACCGCACCTACACCTGCCAGGTCACCTATCAAGGTCACACCTTT
GAGGACAGCACCAAGAAGTGTGCAG

FIG. 22B

SEQ ID NO:15

ATTCCAACCCGAGAGGGGTGAGCGCCTACCTAAGCCGGCCCAGCCCGTT
CGACCTGTTCATCCGCAAGTCGCCCACGATCACCTGTCTGGTGGTGGACC
TGGCACCCAGCAAGGGGACCGTGAACCTGACCTGGTCCCGGGCCAGTGG
GAAGCCTGTGAACCACTCCACCAGAAAGGAGGAGAAGCAGCGCAATGGC
ACGTTAACCGTCACGTCCACCCTGCCGGTGGGCACCCGAGACTGGATCG
AGGGGGAGACCTACCAGTGCAGGGTGACCCACCCCCACCTGCCCAGGGC
CCTCATGCGGTCCACGACCAAGACCAGCG

FIG. 22C

SEQ ID NO:16

GCCCGCGTGCTGCCCCGGAAGTCTATGCGTTTGCGACGCCGGAGTGGCC
GGGGAGCCGGGACAAGCGCACCCTCGCCTGCCTGATCCAGAACTTCATG
CCTGAGGACATCTCGGTGCAGTGGCTGCACAACGAGGTGCAGCTCCCGG
ACGCCCGGCACAGCACGACGCAGCCCCGCAAGACCAAGGGCTCCGGCTT
CTTCGTCTTCAGCCGCCTGGAGGTGACCAGGGCCGAATGGGAGCAGAAA
GATGAGTTCATCTGCCGTGCAGTCCATGAGGCAGCGAGCCCCTCACAGA
CCGTCCAGCGAGCGGTGTCTGTAAATCCCGGTAAATGA

FIG. 22D

SEQ ID NO:17

**GTACGGTGGCGGCGCCATCTGTCTTCATCTTCCCGCCATCTGATGAGCAG
TTGAAATCTGGAACTGCCTCTGTTGTGTGCCTGCTGAATAACTTCTATCC
CAGAGAGGCCAAAGTACAGTGGAAGGTGGATAACGCCCTCCAATCGGGT
AACTCCCAGGAGAGTGTCACAGAGCAGGACAGCAAGGACAGCACCTACA
GCCTCAGCAGCACCCTGACGCTGAGCAAAGCAGACTACGAGAAACACAA
AGTCTACGCCTGCGAAGTCACCCATCAGGGCCTGAGCTCGCCCGTCACAA
AGAGCTTCAACAGGGGAGAGTGTTAG**

FIG. 23

```
                              <---------------------------------------- FRI - IMGT
                              1         5                    10                   15
                              Q   V   K   L   Q   Q   S   G   G       G   L   V   Q   P
MAA_Vh                        caa gtc aaa ctg cag cag agc ggt gga ... ggc ctg gtg cag cct
                              E               E   E
AJ972404 Musmus IGHV6-6*02 F  g-- --g --g --t g-- g-- tct --a --- ... --- t-- --- --a ---
                              -----------------------------------------> ____________
                                                  20                  25              30
                              G   G   S   M   K   L   S   C   V   V   S   G   F   T   F
MAA_Vh                        ggt ggc agc atg aag ctg agc tgc gtc gtg agc ggc ttc acc ttc

AJ972404 Musmus IGHV6-6*02 F   --a --a tc- --- --a --c tc- --t --t -cc tct --a --- --t ---
                              __ CDR1 - IMGT ___________ <-------------------------
                                              35                  40                  45
                                              S   N   Y   W   M   N   W   V   R   Q   S
MAA_Vh                        ... ... ... ... agc aac tac tgg atg aac tgg gtc cgg cag agc

AJ972404 Musmus IGHV6-6*02 F  ... ... ... ... --t --- --- --- --- --- --- --- --c --- tct
                              FR2 - IMGT ------------------------> ___________ CDR2
                                              50                  55                  60
                              P   E   K   G   L   E   W   I   A   E   I   R   L   K   S
MAA_Vh                        ccc gag aag ggc ctg gaa tgg atc gcc gag atc cgg ctg aaa agc
                                                          V       A
AJ972404 Musmus IGHV6-6*02 F  --a --- --- --g --t --g --- g-t --t --a --t a-a t-- --- tct
                              - IMGT ________ <-------------------------------------
                                              65                  70                  75
                              N   N   F   G   R   Y   Y   A   E   S   V   K       G   R
MAA_Vh                        aac aac ttc ggc cgg tac tac gcc gag agc gtg aag ... ggc cgg
                                      Y   A   T   H
AJ972404 Musmus IGHV6-6*02 F  --t --t -at -ca aca c-t --t --g --- tct --- --a ... --g a--

                              ------------------------------ FR3 - IMGT --------------
                                                  80                  85              90
MAA_Vh                        F   T   I   S   R   D   D   S   K   S   S   A   Y   L   Q
                              ttc acc atc agc cgg gac gac agc aag agc agc gcc tac ctg cag
AJ972404 Musmus IGHV6-6*02 F  --- --- --- tca a-a --t --t tc- --a --t --t -t- --- --- --a
                              ----------------------------------------------------> ___
                                                  95                  100         104
                              M   I   N   L   R   A   E   D   T   G   I   Y   Y   C   T
MAA_Vh                        atg atc aac ctg cgg gcc gag gac acc ggc atc tac tac tgc acc
                                  N
AJ972404 Musmus IGHV6-6*02 F  --- -a- --- t-a a-a --t --a --- --t --- --t --t --- --t ---
                              _____________ CDR3 - IMGT _______________
                              S   Y   G   N   Y   V   G   H   Y   F   D   H   W   G   Q
MAA_Vh                        agc tac ggc aac tac gtg ggc cac tac ttc gac cac tgg ggc cag
                              R
AJ972404 Musmus IGHV6-6*02 F  --g

MAA_Vh                        G   T   T   V   T   V   S   S
                              ggc acc acc gtg act gtc agc agc g
```

FIG. 24

```
                                 <---------------------------------------- FRI - IMGT
                                 1          5                   10                  15
                                 D   I   E   L   T   Q   S   P   K   F   M   S   T   S   V
MAA_Vk                           gac atc gag ctg acc cag agc ccc aag ttc atg agc acc agc gtg
Y15976 Musmus IGKV6-15*01 F      --- --t -t- a-- --- --- tct -aa --a --- --- tc- --a tca --a
                                 ------------------------------------> ____________
                                            20                  25                  30
                                 C   D   R   V   S   V   T   C   K   A   S   Q   N   V
MAA_Vk                           ggc gac aga gtg tcc gtg acc tgc aag gcc agc cag aac gtg ...
Y15976 Musmus IGKV6-15*01 F      --a --- --g --c ag- --c --- --- --- --- --t --- --t --- ...
                                 __ CDR1 - IMGT ___________ <-------------------------
                                            35                  40                  45
                                                     D   T   N   V   A   W   Y   Q   Q   K
MAA_Vk                           ... ... ... ... ... gac acc aac gtg gcc tgg tat cag cag aag
                                                     G
Y15976 Musmus IGKV6-15*01 F      ... ... ... ... ... -gt --t --t --a --- --- --- --a --- --a
                                 FR2 - IMGT ------------------------> ____________ CDR2
                                            50                  55                  60
                                 P   G   Q   S   P   E   P   L   L   F   S   A
MAA_Vk                           ccc ggc cag agc cct gag cct ctg ctg ttc agc gcc ... ... ...
                                                     K   A       I   Y
Y15976 Musmus IGKV6-15*01 F      --a --g --a tct --- a-a g-a --- a-t -a- tcg --a ... ... ...
                                 - IMGT ________ <-----------------------------------
                                            65                  70                  75
                                            S   Y   R   Y   T   G   V   P       D   R
MAA_Vk                           ... ... ... ... agc tac aga tac acc ggc gtg ccc ... gac aga
                                                                 S
Y15976 Musmus IGKV6-15*01 F      ... ... ... ... tc- --- c-g --- -gt --a --c --t ... --t c-c
                                 --------------------------- FR3 - IMGT -------------
                                            80                  85                  90
                                 F   T   G   S   G           S   G   T   D   F   T   L   T
MAA_Vk                           ttc aca ggc agc ggc ... ... tcc ggc acc gac ttc acc ctg acc
Y15976 Musmus IGKV6-15*01 F      --- --- --- --t --a ... ... --t --q --a --t --- --t --c ---
                                 ------------------------------------------------> ___
                                            95                  100                 104
                                 I   S   N   V   Q   S   E   D   L   A   E   Y   F   C   Q
MAA_Vk                           atc agc aac gtg cag agc gag gac ctg gcc gag tac ttc tgc cag
Y15976 Musmus IGKV6-15*01 F      --- --- --t --- --- tct --a --- t-- --a --- --t --- --t ---
                                 ______ CDR3 - IMGT _______
                                 Q   Y   N   S   Y   P   L   T   F   G   G   G   T   K   L
MAA_Vk                           cag tac aac agc tac ccc ctg acc ttc ggc gga ggc acc aag ctg
Y15976 Musmus IGKV6-15*01 F      --a --t --- --- --t --t --
                                 E   I   K
MAA_Vk                           gaa atc aag c
Y15976 Musmus IGKV6-15*01 F
```

FIG. 25

IGE ANTI-HMW-MAA ANTIBODY

SEQUENCE LISTING SUBMISSION VIA EFS-WEB

A computer readable text file, entitled "067024-5016_SequenceListing.txt," created on or about 31 Mar. 2014, with a file size of about 52 kb contains the sequence listing for this application and is hereby incorporated by reference in its entirety.

FIELD

The present invention relates to the field of antibodies, and in particular to therapeutic antibodies for the treatment of cancer, especially skin cancer.

BACKGROUND

Malignant melanoma is an immunogenic, highly aggressive and most lethal form of skin cancer. It is the most common cancer in the 17-34 years age group but affects people of all ages, and therefore has a significant socioeconomic impact for patients and their families Rates of melanoma have been rising by 5% per year, faster than any other cancer in the UK [1]. Although diagnosed skin lesions can be initially excised by surgical intervention, skin and distal metastases unfortunately occur in 20% of patients originally treated with local disease. Patients with lymph node and other distal metastases have dismal prognosis, and this is partly due to lack of effective treatments for this cohort.

Melanoma has presented major challenges to numerous targeted therapy efforts and therefore effective treatments are urgently needed for patients with this disease. The recent approval of the monoclonal antibody ipilimumab (targeting the CTLA4 blockade to enhance T cell activation) for the treatment of melanoma lends merit to the notion that activating immune responses with antibodies may have therapeutic significance and has renewed interest in the field of antibody therapies for the treatment of challenging tumours such as melanoma [2-4]. Despite the partial success and promise of various immunotherapeutic strategies, including antibodies, there are presently no promising antibody therapies that directly target antigens on the surface of melanoma cells.

Therapeutic antibodies now complement conventional treatments for a number of malignant diseases, but almost all agents currently developed rely on only one of the nine human antibody classes, namely $IgG_1$, the most abundant antibody class in the blood [5]. The human immune system naturally deploys nine antibody classes and subclasses (IgM, IgD, IgG1-4, IgA1, IgA2 and IgE) to perform immune surveillance and to mediate destruction of pathogens in different anatomical compartments. Yet only IgG (most often IgG1) has been applied in immunotherapy of cancers.

One reason may be that IgG antibodies (particularly IgG1), constitute the largest fraction of circulating antibodies in human blood. The choice of antibody class is also based on pioneering work in the late 1980s, comparing a panel of chimaeric antibodies of the same specificity, each with Fc regions belonging to one of the nine antibody classes and subclasses [6]. Antibodies were evaluated for their ability to bind complement and their potency to mediate haemolysis and cytotoxicity of antigen-expressing target cells in the presence of complement. IgG1 in combination with human peripheral blood mononuclear cells (PBMC) was the most effective IgG subclass in complement-dependent cell killing in vitro, while the IgA and IgE antibodies were completely inert.

Subsequent clinical trials with antibodies recognising the B cell marker CD20 supported the inference that IgG1 would be the subclass best suited for immunotherapy of patients with B cell malignancies such as non-Hodgkin's lymphoma [7]. Since those studies, comparisons of anti-tumour effects by different antibody classes have been confined to IgG and IgM in both murine models and patients with lymphoid malignancies, while IgA has been shown to mediate ADCC in vitro and in vivo in mouse models of lymphoma [8-12]. IgA and IgE antibodies, on the other hand, have never been tested in cancer patients.

Complement-mediated tumour cell death is now known to be only one of several mechanisms by which antibodies may mediate tumour growth restriction [13]. Known mechanisms include engaging immune effector molecules through their Fc regions to induce immune cell mediated destruction of targeted cells by antibody-dependent cell-mediated cytotoxicity (ADCC) and phagocytosis (ADCP). Antibodies can also act directly on tumour cells to inhibit growth signalling pathways, induce apoptosis, restrict proliferation and cell differentiation of tumour cells, or block tumour cell adhesion and migration. Some antibodies are developed to recognise targets associated with tumour-associated vasculature in order to starve tumours of vital nutrients delivered through blood supply, while others attack immune regulatory targets (e.g. CTLA-4 and PD-1R) to enhance T cell activation and overcome immunosuppressive elements of the immune response [14, 15, 3]. Extensive efforts have also focused on designing antibody conjugates to deliver toxic payloads in the form of drug-activating enzymes, cytokines or radionuclides to tumours [16]. Multiple antibody engineering approaches are also being devised to improve validated therapeutics, such as trastuzumab, with the principal aims to optimise antigen specificity/affinity and effector functions of IgG antibodies [17].

Accordingly, there is still a need for improved therapeutic antibodies, particularly for the treatment of neoplastic diseases such as skin cancer. In particular, there is a need for antibodies having improved effector functions compared to IgG antibodies, which may lead to an improved clinical outcome in the treatment of cancer, especially skin cancer.

SUMMARY

Accordingly, in one aspect the present invention provides an antibody or a functional fragment thereof, wherein the antibody or functional fragment thereof is capable of binding specifically to high molecular weight melanoma associated antigen (HMW-MAA), and binding to an Fcϵ receptor.

In one embodiment, the antibody is of the isotype IgE. For instance, the antibody or functional fragment thereof may comprise one or more heavy chain constant domains selected from Cϵ1, Cϵ2, Cϵ3 and Cϵ4. Preferably the antibody comprises an ϵ heavy chain. Thus in a further aspect, the present invention provides an immunoglobulin E antibody which binds specifically to the tumour-associated antigen high molecular weight melanoma associated antigen (HMW-MAA).

In another embodiment, the antibody comprises one or more variable regions capable of binding specifically to HMW-MAA, and one or more constant regions capable of binding to an Fcε receptor. In specific embodiments, the antibody is a chimaeric antibody, a humanized antibody or a human antibody.

In one embodiment, the antibody comprises one or more variable domains derived from an immunoglobulin isotype other than IgE (e.g. IgA, IgD, IgG or IgM, for example IgG1), and one or more constant domains derived from an immunoglobulin of the isotype IgE.

In another embodiment, the antibody comprises one or more complementarity-determining regions (CDRs) derived from an immunoglobulin isotype other than IgE (e.g. IgA, IgD, IgG or IgM, for example IgG1), and one or more framework regions and/or constant domains derived from an immunoglobulin of the isotype IgE.

For instance, the antibody may comprise one or more variable domains or complementarity-determining regions (CDRs) derived from an IgG, e.g. IgG1.

In one embodiment, the variable domains or CDRs are derived from a first mammalian species, and the framework regions and/or constant domains are derived from a second mammalian species different to the first mammalian species. In one embodiment, the variable regions or CDRs are derived from a non-human species, e.g. a mouse. In an alternative embodiment, the variable regions or CDRs are derived from a human sequence. Preferably the framework regions and/or constant domains are human.

In a further aspect, the invention provides a pharmaceutical composition comprising an antibody or functional fragment thereof as defined above, and a pharmaceutically acceptable carrier.

In another aspect, the invention provides a method of treating a subject suffering from cancer, comprising administering to the subject a therapeutically effective amount of an antibody or functional fragment thereof or a pharmaceutical composition as defined above.

In another aspect, there is provided use of an antibody or functional fragment thereof or a pharmaceutical composition as above, for the preparation of a medicament for the treatment of cancer.

In another aspect, there is provided an antibody or functional fragment thereof or a pharmaceutical composition as defined above, for use in the treatment of cancer.

Preferably the cancer expresses HMW-MAA. In specific embodiments, the cancer may be skin cancer, breast cancer, head and neck squamous cell carcinoma, prostate cancer, ovarian cancer, colon cancer, glioma, stomach cancer or pancreatic cancer. In a preferred embodiment the cancer is malignant melanoma.

In another aspect, the invention provides a nucleic acid molecule which encodes the antibody or functional fragment thereof as defined above. Also provided is an expression vector comprising the nucleic acid molecule operably linked to a promoter, and a host cell transformed with the expression vector.

BRIEF DESCRIPTION OF THE DRAWINGS

FIG. 10: Amino acid sequence of human HMW-MAA (SEQ ID NO:1).

FIG. 11: Nucleic acid sequence encoding human HMW-MAA (SEQ ID NO:2).

FIG. 12: Nucleic acid sequence (SEQ ID NO:3) encoding the heavy chain variable region ($V_H$) of scFv (225.28S), as previously published in Neri D, et al. (1996), Recombinant anti-human melanoma antibodies are versatile molecules, J Invest Dermatol 107: 164-170.

FIG. 13: Amino acid sequence (SEQ ID NO:4) of the heavy chain variable region ($V_H$) of scFv (225.28S), as previously published in Neri D, et al. (1996) supra.

FIG. 14: Nucleic acid sequence (SEQ ID NO:5) encoding the light chain variable region ($V_K$) of scFv (225.28S), as previously published in Neri D, et al. (1996) supra.

FIG. 15: Amino acid sequence (SEQ ID NO:6) of the light chain variable region ($V_K$) of scFv (225.28S), as previously published in Neri D, et al. (1996) supra.

FIG. 16: Amino acid sequence (SEQ ID NO:7) of the heavy (ϵ) chain of chimeric anti-HMW-MAA IgE antibody, as described in the Example below. Bold: Variable region (derived from scFv (225.28S). Underline: Constant region (human ϵ constant region).

FIG. 17: Amino acid sequence (SEQ ID NO:8) of the light (κ) chain of chimeric anti-HMW-MAA IgE antibody, as described in the Example below. Bold: Variable region (derived from scFv (225.28S). Underline: Constant region (human κ constant region).

FIG. 18: Nucleic acid sequence (SEQ ID NO:9) encoding the heavy (ϵ) chain of chimeric anti-HMW-MAA IgE antibody, as described in the Example below. Bold: Variable region-encoding part (derived from scFv (225.28S). Underline: Constant region-encoding part (human ϵ constant region).

FIG. 19: Nucleic acid sequence (SEQ ID NO:10) encoding the light (κ) chain of chimeric anti-HMW-MAA IgE antibody, as described in the Example below. Bold: Variable region-encoding part (derived from scFv (225.28S). Underline: Constant region-encoding part (human κ constant region).

FIG. 20: Nucleic acid sequence (SEQ ID NO:11) comprising human codon optimisations, encoding the heavy chain variable region ($V_H$) of chimeric anti-HMW-MAA IgE antibody, as described in the Example below.

FIG. 21: Nucleic acid sequence (SEQ ID NO:12) comprising human codon optimisations, encoding the light chain variable region ($V_K$) of chimeric anti-HMW-MAA IgE antibody, as described in the Example below.

FIG. 22: Nucleic acid sequences encoding human immunoglobulin heavy (ϵ) chain constant domains, as described in NCBI database accession number L00022.1. A: $CH_{(\epsilon)}1$ (SEQ ID NO:13); B: $CH_{(\epsilon)}2$ (SEQ ID NO:14); C: $CH_{(\epsilon)}3$ (SEQ ID NO:15); D: $CH_{(\epsilon)}4$ (SEQ ID NO:16).

FIG. 23: Nucleic acid sequence encoding human light (κ) chain constant domain (SEQ ID NO:17).

FIG. 24: Location of CDR and framework regions within the heavy chain variable domain (VH) present in mAb 225.28s and chimeric anti-HMW-MAA IgE antibodies.

FIG. 25: Location of CDR and framework regions within the light chain variable domain (VL) present in mAb 225.28s and chimeric anti-HMW-MAA IgE antibodies.

DETAILED DESCRIPTION

High Molecular Weight Melanoma-Associated Antigen (HMW-MAA)

Figure 1A:
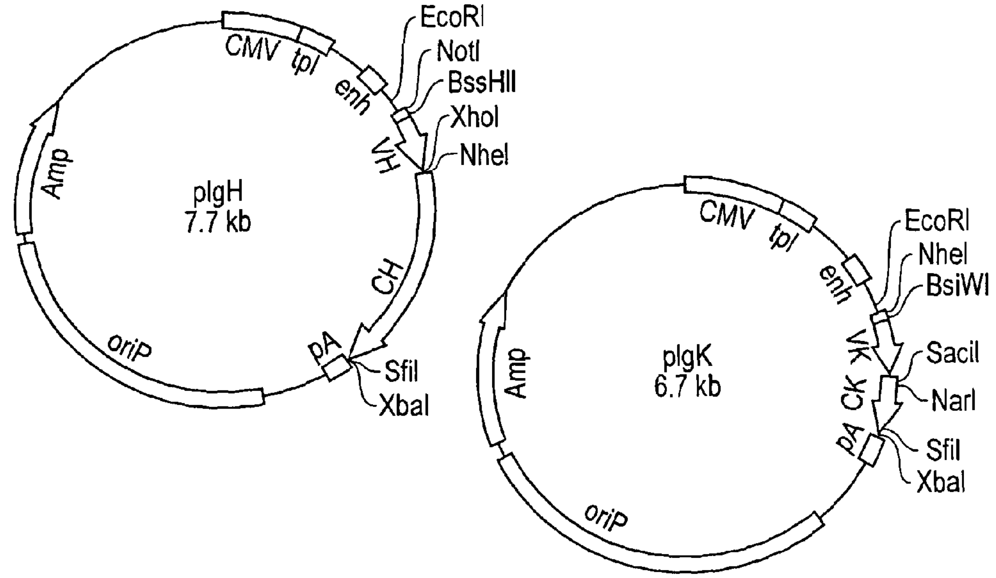
FIG. 1: A: Schematic representations of the heavy and light chain vector design for expression cloning of IgG and IgE antibodies. B: Schematic representation of the design of IgE and IgG1 antibodies of the same specificity: the variable heavy and light chains of $IgG_1$ (left, regions indicated with stars) were inserted into the epsilon heavy chain regions of IgE and the epsilon heavy chain was combined with the kappa light chain to produce the corresponding IgE antibody (right). Glycosylation sites are depicted by black circles.

Antibodies or fragments thereof according to embodiments of the present invention bind to high molecular weight melanoma-associated antigen (HMW-MAA).

HMW-MAA is also known as Melanoma-Associated Chondroitin Sulfate Proteoglycan (MCSP), "human melanoma proteoglycan" (HMP), "melanoma-associated proteoglycan antigen" (MPG) and "melanoma chondroitin sulfate proteoglycan" (mel-CSPG). HMW-MAA is also known as CSPG4. HMW-MAA is a human melanoma-associated chondroitin sulfate proteoglycan that plays a role in stabilizing cell-substratum interactions during early events of melanoma cell spreading on endothelial basement membranes.

Thus HMW-MAA represents an integral membrane chondroitin sulfate proteoglycan expressed by human malignant melanoma cells. In vivo, it is present in a molecule that consists of two noncovalently associated glycopolypeptides. One has an apparent molecular weight of 280K, and the other has an apparent molecular weight greater than 440K.

HMW-MAA is synthesized and expressed by human melanoma cells (Spiro, R. C. et al. F. Biol. Chem. 264:1779 (1989); Esko, J. D., et al., Science 241:1092, 1988). Proteoglycans are glycoproteins with glycosaminoglycan (GAG) polysaccharide chains covalently attached to the serine residue in their core. The HMW-MAA core protein is initially translated as a precursor with a molecular mass of 240K with asparagine N-linked oligosaccharides of the high mannose type.

In one embodiment, HMW-MAA has an amino acid sequence as shown in SEQ ID NO:1. The amino acid sequence of HMW-MAA is also disclosed in NCBI database accession no. NP_001888.2 and SwissProt entry no. Q6UVK1.

In one embodiment, HMW-MAA is encoded by a nucleic acid sequence as shown in SEQ ID NO:2. The nucleic acid sequence encoding HMW-MAA is also disclosed in NCBI database accession no. NM_001897.4.

The antibodies described herein bind specifically to HMW-MAA. For instance, the antibodies may bind (e.g. via the antigen-specific binding site(s) or paratopes of the antibody, which are present within the variable regions) to an antigenic epitope present within the HMW-MAA protein. Typically the antibody may bind to HMW-MAA with high affinity, e.g. with a dissociation constant ($K_d$) of less than 1 μM, preferably less than 1 nM. Preferably the antibody specifically binds to HMW-MAA and does not significantly bind unrelated antigens.

Binding affinity of the antibody for HMW-MAA may be calculated using standard methods, e.g. based on the Scatchard method as described by Frankel et al., Mol. Immunol., 16:101-106, 1979. Binding affinity may also be measured by calculating the antigen/antibody dissociation rate, by a competition radioimmunoassay, by enzyme-linked immunosorbent assay (ELISA), or by Surface Plasmon Resonance.

Antibodies

Antibodies are polypeptide ligands comprising at least a light chain or heavy chain immunoglobulin variable region which specifically recognizes and specifically binds an epitope of an antigen, such as HMW-MAA, or a fragment thereof. Antibodies are typically composed of a heavy and a light chain, each of which has a variable region, termed the variable heavy (VH) region and the variable light (VL) region. Together, the VH region and the VL region are responsible for binding the antigen recognized by the antibody.

Antibodies include intact immunoglobulins and the variants and portions of antibodies well known in the art, provided that such fragments are capable of binding an Fcϵ receptor. Antibodies also include genetically engineered forms such as chimaeric, humanized (for example, humanized antibodies with murine sequences contained in the variable regions) or human antibodies, heteroconjugate antibodies (such as, bispecific antibodies), e.g. as described in Kuby, J., Immunology, 3rd Ed., W.H. Freeman & Co., New York, 1997.

Typically, a naturally occurring immunoglobulin has heavy (H) chains and light (L) chains interconnected by disulfide bonds. There are two types of light chain, lambda (λ) and kappa (κ). There are nine main isotypes or classes which determine the functional activity of an antibody molecule: IgA1-2, IgD, IgE, IgG1-4 and IgM, corresponding to the heavy chain types α, δ, ε, γ, and μ. Thus, the type of heavy chain present defines the class of antibody. Distinct heavy chains differ in size and composition; α and γ contain approximately 450 amino acids, while μ and ε have approximately 550 amino acids. The differences in the constant regions of each heavy chain type account for the different effector functions of each antibody isotype, by virtue of their selective binding to particular types of receptor (e.g. Fc receptors). Accordingly, in embodiments of the present invention the antibody preferably comprises an epsilon (ε) heavy chain, i.e. the antibody is of the isotype IgE which binds to Fcε receptors.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs." The extent of the framework region and CDRs has been defined (see, Kabat et al., Sequences of Proteins of Immunological Interest, U.S. Department of Health and Human Services, 1991). The Kabat database is now maintained online. The sequences of the framework regions of different light or heavy chains are relatively conserved within a species, such as humans. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a VH CDR3 is located in the variable domain of the heavy chain of the antibody in which it is found, whereas a VL CDR1 is the CDR1 from the variable domain of the light chain of the antibody in which it is found.

Antibodies which bind HMW-MAA may have a specific VH region and the VL region sequence, and thus specific CDR sequences. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs). Thus in embodiments of the present invention, the antibody comprises at least one, two, three, four, five or six CDRs (e.g. 3 heavy chain CDRs and/or 3 light chain CDRs) or at least one variable domain (e.g. a VH or VL domain) derived from an antibody which binds to HMW-MAA.

References to "VH" refer to the variable region of an immunoglobulin heavy chain. References to "VL" refer to the variable region of an immunoglobulin light chain.

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "chimaeric antibody" comprises sequences derived from two different antibodies, which are typically derived from different species. For example, chimaeric antibodies may include human and murine antibody domains, e.g. human constant regions and murine variable regions (e.g. from a murine antibody that specifically binds HMW-MAA).

Chimaeric antibodies are typically constructed by fusing variable and constant regions, e.g. by genetic engineering, from light and heavy chain immunoglobulin genes belonging to different species. For example, the variable segments of the genes from a mouse monoclonal antibody can be joined to human constant segments, such as kappa and epsilon. In one example, a therapeutic chimaeric antibody is thus a hybrid protein composed of the variable or antigen-binding domain from a mouse antibody and the constant or effector domain from a human antibody, e.g. an Fc (effector) domain from a human IgE antibody, although other mammalian species can be used, or the variable region can be produced by molecular techniques. Methods of making chimaeric antibodies are well known in the art, e.g., see U.S. Pat. No. 5,807,715.

A "humanized" antibody is an antibody including human framework regions and one or more CDRs from a non-human (for example a mouse, rat, or synthetic) antibody. The non-human immunoglobulin providing the CDRs is termed a "donor", and the human immunoglobulin providing the framework is termed an "acceptor". In one embodiment, all the CDRs are from the donor immunoglobulin in a humanized immunoglobulin. The constant regions are typically substantially identical to human immunoglobulin constant regions, i.e., at least about 85-90%, such as about 95% or more identical. Hence, all parts of a humanized immunoglobulin, except the CDRs, are substantially identical to corresponding parts of natural human immunoglobulin sequences.

A humanized antibody typically comprises a humanized immunoglobulin light chain and a humanized immunoglobulin heavy chain. A humanized antibody typically binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions.

Humanized immunoglobulins can be constructed by means of genetic engineering (see for example, U.S. Pat. No. 5,585,089). Typically humanized monoclonal antibodies are produced by transferring donor antibody complementarity determining regions from heavy and light variable chains of a mouse immunoglobulin into a human variable domain, and then substituting human residues in the framework regions of the donor counterparts. The use of antibody components derived from humanized monoclonal antibodies obviates potential problems associated with the immunogenicity of the constant regions of the donor antibody. Techniques for producing humanized monoclonal antibodies are described, for example, by Jones et al., Nature 321:522, 1986; Riechmann et al., Nature 332:323, 1988; Verhoeyen et al., Science 239:1534, 1988; Carter et al., Proc. Nat'l Acad. Sci. U.S.A. 89:4285, 1992; Sandhu, Crit. Rev. Biotech. 12:437, 1992; and Singer et al., J. Immunol. 150:2844, 1993.

A "human" antibody (also called a "fully human" antibody) is an antibody that includes human framework regions and all of the CDRs from a human immunoglobulin. In one example, the framework and the CDRs are from the same originating human heavy and/or light chain amino acid sequence. However, frameworks from one human antibody can be engineered to include CDRs from a different human antibody.

In embodiments of the present invention, the antibodies may be monoclonal or polyclonal antibodies, including chimaeric, humanized or fully human antibodies.

Antibodies which Bind to HMW-MAA

In some embodiments, the antibody binds specifically to HMW-MAA to form an immune complex. Typically the antibody may comprise an antigen-binding region (e.g. one or more variable regions, or one to 6 CDRs) derived from an antibody which is known to bind. HMW-MAA, preferably human HMW-MAA.

Antibodies which bind to HMW-MAA are disclosed, for example, in WO 89/11296. Such antibodies include mouse monoclonal antibodies 225.28s; 763.74; VF1-TP41.2; VT80.112; 653.25; 763.74; TP61.5 and T8-203 (see WO 89/11296; Drake et al., Cancer Immunol. Immunother. DOI 10: 1007, s00262-008-0567-5, 2008; Goto et al., Clin. Cancer Res. 14: 3401-3407, 2008).

In one specific embodiment, the antibody comprises a variable region (e.g. a heavy chain variable domain (VH) and/or a light chain variable domain (VL)) or at least one, two, three, four, five or six CDRs (e.g. 3 heavy chain CDRs or 3 light chain CDRs) from mouse monoclonal antibody (mAb) 225.28s. The amino acid sequences of the VH and VL domains of mAb 225.28s are shown in SEQ ID NO:4 and SEQ ID NO:6, respectively, and the corresponding nucleic acid sequences which encode these domains are shown in SEQ ID NO:3 and SEQ ID NO:5 respectively. The heavy and light chain CDR sequences from mAb 225.28s are shown in FIGS. 24 and 25 respectively, and in SEQ ID NO:s 18 to 20 and 21 to 23 respectively. In another embodiment, the antibody is a chimaeric, humanized or fully human antibody that specifically binds the epitope bound by mAb 225.28s.

In another specific example, the antibody comprises a variable region (e.g. a heavy chain variable domain and/or a light chain variable domain) or at least one, two, three, four, five or six CDRs (e.g. 3 heavy chain CDRs or 3 light chain CDRs) from mAb 763.74, or is a chimaeric, humanized or fully human antibody that specifically binds the epitope bound by mAb 763.74.

In another example, the antibody comprises a variable region (e.g. a heavy chain variable domain and/or a light chain variable domain) or at least one, two, three, four, five or six CDRs (e.g. 3 heavy chain CDRs or 3 light chain CDRs) derived from a human B cell clone that recognises an epitope found on HMW-MAA, preferably human HMW-MAA.

In one embodiment, the antibody comprises one or more human constant regions, e.g. one or more human heavy chain constant domains (e.g. E constant domains) and/or a human light chain (e.g. κ or λ) constant domain. A nucleotide sequence encoding a human light (κ) chain constant domain is shown in SEQ ID NO:17. More preferably the antibody comprises one or more human framework regions within the VH and/or VL domains.

In one embodiment, the sequence of the humanized immunoglobulin heavy chain variable region framework can be at least about 65% identical to the sequence of the donor immunoglobulin heavy chain variable region framework. Thus, the sequence of the humanized immunoglobulin heavy chain variable region framework can be at least about 75%, at least about 85%, at least about 99% or at least about 95%, identical to the sequence of the donor immunoglobulin heavy chain variable region framework. Human framework regions, and mutations that can be made in a humanized antibody framework regions, are known in the art (see, for example, U.S. Pat. No. 5,585,089).

Fully human antibodies and fragments thereof which bind to HMW-MAA are disclosed in WO 2010/045495, e.g. an scFv fragment isolated from a semi-synthetic phage display scFv antibody library and designated C21. In some embodiments, the antibody may comprise a heavy chain variable domain and/or a light chain variable domain) or at least one, two, three, four, five or six CDRs (e.g. 3 heavy chain CDRs or 3 light chain CDRs) from scFv C21.

Further antibodies against HMW-MAA sequences may also be generated by well-established methods, and at least the variable regions or CDRs from such antibodies may be used in the antibodies of the present invention (e.g. the generated antibodies may be used to donate CDR or variable region sequences into IgE acceptor sequences). Methods for synthesizing polypeptides and immunizing a host animal are well known in the art. Typically, the host animal (e.g. a mouse) is inoculated intraperitoneally with an amount of immunogen (i.e. HMW-MAA or a polypeptide comprising an immunogenic fragment thereof), and (in the case of monoclonal antibody production) hybridomas prepared from its lymphocytes and immortalized myeloma cells using the general somatic cell hybridization technique of Kohler, B. and Milstein, C. (1975) Nature 25 6:495-497.

Hybridomas that produce suitable antibodies may be grown in vitro or in vivo using known procedures. Monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity if present, can be removed, for example, by running the preparation over adsorbents made of the immunogen attached to a solid phase and eluting or releasing the desired antibodies off the immunogen. If desired, the antibody (monoclonal or polyclonal) of interest may be sequenced and the polynucleotide sequence may then be cloned into a vector for expression or propagation. The sequence encoding the antibody may be maintained in a vector in a host cell and the host cell can then be expanded and frozen for future use.

Phage display technology, for instance as described in U.S. Pat. No. 5,565,332 and other published documents, may be used to select and produce human antibodies and antibody fragments in vitro, from immunoglobulin variable (V) domain gene repertoires from unimmunized donors (e.g. from human subjects, including patients suffering from a relevant disorder). For example, existing antibody phage display libraries may be panned in parallel against a large collection of synthetic polypeptides. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus antibody sequences selected using phage display from human libraries may include human CDR or variable region sequences conferring specific binding to HMW-MAA, which may be used to provide fully human antibodies for use in the present invention.

Methods for deriving heavy and light chain sequences from human B cell and plasma cell clones are also well known in the art and typically performed using polymerase chain reaction (PCR) techniques, examples of the methods are described in: Kuppers R, Methods Mol Biol. 2004; 271:225-38; Yoshioka M et al., BMC Biotechnol. 2011 Jul. 21; 11:75; Scheeren F A et al., PLoS ONE 2011, 6(4): e17189. doi:10.1371/journal.pone.0017189; Wrammert J et al., Nature 2008 453, 667-671; Kurosawa N et al., BMC Biotechnol. 2011 Apr. 13; 11:39; Tiller et al., J Immunol Methods. 2008 Jan. 1; 329(1-2): 112-124. Thus antibody sequences selected using B cell clones may include human CDR or variable region sequences conferring specific binding to HMW-MAA, which may be used to provide fully human antibodies for use in the present invention.

Antibodies which Bind Fcϵ Receptors

The antibodies described herein are also capable of binding to Fcϵ receptors, e.g. to the FcϵRI and/or the FcϵRII receptors. Preferably the antibody is at least capable of binding to FcϵRI (i.e. the high affinity Fcϵ receptor) or is at least capable of binding to FcϵRII (CD23, the low affinity Fcϵ receptor). Typically the antibodies are also capable of activating Fcϵ receptors, e.g. expressed on cells of the immune system, in order to initiate effector functions mediated by IgE.

The epsilon (ϵ) heavy chain is definitive for IgE antibodies, and comprises an N-terminal variable domain VH, and four constant domains Cϵ1-Cϵ4. As with other antibody isotypes, the variable domains confer antigen specificity and the constant domains recruit the isotype-specific effector functions.

IgE differs from the more abundant IgG isotypes, in that it is unable to fix complement and does not bind to the Fc receptors FcγRI, RII and RIII expressed on the surfaces of mononuclear cells, NK cells and neutrophils. However, IgE is capable of very specific interactions with the “high affinity” IgE receptor on a variety of immune cells such as mast cells, basophils, monocytes/macrophages, eosinophils (FcϵRI, Ka. $10^{11}$ $M^{-1}$), and with the “low affinity” receptor, Fcϵ RII (Ka. $10^{7}$ $M^{-1}$), also known as CD23, expressed on inflammatory and antigen presenting cells (e.g. monocytes/macrophages, platelets, dendritic cells, T and B lymphocytes.

The sites on IgE responsible for these receptor interactions have been mapped to peptide sequences on the Cϵ chain, and are distinct. The FcγRI site lies in a cleft created by residues between Gln 301 and Arg 376, and includes the junction between the Cϵ2 and Cϵ3 domains [Helm, B. et al. (1988) Nature 331, 180183]. The FcϵRII binding site is located within Cϵ3 around residue Val 370 [Vercelli, D. et al. (1989) Nature 338, 649-651]. A major difference distinguishing the two receptors is that FcϵRI binds monomeric Cϵ, whereas FcϵRII will only bind dimerised Cϵ, i.e. the two Cϵ chains must be associated. Although IgE is glycosylated in vivo, this is not necessary for its binding to FcϵRI and FcϵRRII. Binding is in fact marginally stronger in the absence of glycosylation [Vercelli, D. et al. (1989) et. supra].

Thus binding to Fcϵ receptors and related effector functions are typically mediated by the heavy chain constant domains of the antibody, in particular by domains which together form the Fc region of the antibody. The antibodies described herein typically comprise at least a portion of an IgE antibody e.g. one or more constant domains derived from an IgE, preferably a human IgE. In particular embodiments, the antibodies comprise one or more domains (derived from IgE) selected from Cϵ1, Cϵ2, Cϵ3 and Cϵ4. In one embodiment, the antibody comprises at least Cϵ2 and Cϵ3, more preferably at least Cϵ2, Cϵ3 and Cϵ4, preferably wherein the domains are derived from a human IgE. In one embodiment, the antibody comprises an epsilon (ϵ) heavy chain, preferably a human ϵ heavy chain.

Nucleotide sequences encoding constant domains derived from human IgE, in particular Cϵ1, Cϵ2, Cϵ3 and Cϵ4 domains, are shown in SEQ ID NO:s 13, 14, 15 and 16 respectively and are disclosed in NCBI database accession no. L00022.1. The amino acid sequences corresponding to these nucleic acid sequences can be deduced by a skilled person according to the genetic code and are also indicated in NCBI database accession no. L00022.1. The full length heavy (ϵ) chain constant region amino acid sequence encoded by the combination of SEQ ID NO:s 13, 14, 15 and 16 is also shown in FIG. 16 (SEQ ID NO:7, underlined part). The amino acid sequences of other human and mammalian IgEs and domains thereof, including human Cϵ1, Cϵ2, Cϵ3 and Cϵ4 domains and human c heavy chain sequences, are known in the art and are available from public-accessible databases. For instance, databases of human immunoglobulin sequences are accessible from the International ImMuNoGeneTics Information System (IMGT®) website at www.imgt.org. As one example, the sequences of various human IgE heavy (ϵ) chain alleles and their individual constant domains (Cϵ1-4) are accessible on the world-wide web at www.imgt.org/Th1GT GENEDB/GENE1ect?query=2+IGHE&species=Homo+sapiens.

Preferred Anti-HMW-MAA Antibodies which Bind Fcϵ Receptors

In one embodiment, the anti-HMW-MAA antibody comprises a VH domain encoded by a nucleotide sequence comprising at least a portion of SEQ ID NO: 3 or SEQ ID NO:11, e.g. comprising at least 50, 100, 200, 300 or 350 nucleotides of SEQ ID NO:3 or SEQ ID NO:11, or the full length of SEQ ID NO:3 or SEQ ID NO:11. In one embodiment, the anti-HMW-MAA antibody comprises a VH domain comprising at least a portion of the amino acid sequence as defined in SEQ ID NO:4, e.g. comprising at least 20, 30, 50 or 100 amino acids of SEQ ID NO:4 or the full length of SEQ ID NO:4.

In one embodiment, the anti-HMW-MAA antibody comprises a VL domain encoded by the nucleotide sequence comprising at least a portion of SEQ ID NO: 5 or SEQ ID NO:12, e.g. comprising at least 50, 100, 200, or 300 nucleotides of SEQ ID NO:5 or SEQ ID NO:12, or the full length of SEQ ID NO:5 or SEQ ID NO:12. In one embodiment, the anti-HMW-MAA antibody has a VL domain comprising at least a portion of the amino acid sequence as defined in SEQ ID NO:6, e.g. comprising at least 20, 30, 50 or 100 amino acids of SEQ ID NO:6 or the full length of SEQ ID NO:6.

In one embodiment, the anti-HMW-MAA antibody comprises a heavy chain encoded by a nucleotide sequence comprising at least a portion of SEQ ID NO: 9, e.g. comprising at least 100, 500, 1000 or 1500 nucleotides of SEQ ID NO:9 or the full length of SEQ ID NO:9. In one embodiment, the anti-HMW-MAA antibody comprises a heavy chain comprising at least a portion of the amino acid sequence as defined in SEQ ID NO:7, e.g. comprising at least 50, 100, 300 or 500 amino acids of SEQ ID NO:7 or the full length of SEQ ID NO:7.

In one embodiment, the anti-HMW-MAA antibody comprises a light chain encoded by a nucleotide sequence comprising at least a portion of SEQ ID NO: 10, e.g. comprising at least 50, 100, 300 or 500 nucleotides of SEQ ID NO:10 or the full length of SEQ ID NO:10. In one embodiment, the anti-HMW-MAA antibody comprises a light chain comprising at least a portion of the amino acid sequence as defined in SEQ ID NO:8, e.g. comprising at least 50, 100, 150 or 200 amino acids of SEQ ID NO:8.

In one embodiment, the anti-HMW-MAA antibody comprises one or more heavy chain constant domains encoded by at least a portion of SEQ ID NO:13, SEQ ID NO:14, SEQ ID NO:15 and/or SEQ ID NO:16, e.g. encoded by at least 50, 100, 200 or 300 nucleotides of, or by the full length sequence of one or more of SEQ ID NO:s 13 to 16. In a specific embodiment, the anti-HMW-MAA antibody comprises a heavy chain constant domain encoded by SEQ ID NO:13, SEQ ID NO:14, SEQ ID NO:15 and SEQ ID NO:16.

In one embodiment, the anti-HMW-MAA antibody comprises a light chain constant domain encoded by at least a portion of SEQ ID NO:17, e.g. encoded by at least 50, 100, 200 or 300 nucleotides of, or by the full length sequence of SEQ ID NO:17.

In one embodiment, the anti-HMW-MAA antibody comprises one or more heavy chain CDR sequences selected from GFTFSNYW (SEQ ID NO:18), IRLKSNNFGR (SEQ ID NO:19) and TSYGNYVGHYFDH (SEQ ID NO:20). In another embodiment, the anti-HMW-MAA antibody comprises one or more light chain CDR sequences selected from QNVDTN (SEQ ID NO:21), SAS (SEQ ID NO:22) and QQYNSYPLT (SEQ ID NO:23). Preferably the antibody comprises a heavy chain CDR1 comprising (SEQ ID NO:18), a heavy chain CDR2 comprising (SEQ ID NO:19), a heavy chain CDR3 comprising (SEQ ID NO:20), a light chain CDR1 comprising (SEQ ID NO:21), a light chain CDR2 comprising (SEQ ID NO:22) and/or a light chain CDR3 comprising (SEQ ID NO:23).

In general, functional fragments of the sequences defined above may be used in the present invention. Functional fragments may be of any length as specified above (e.g. at least 50, 100, 300 or 500 nucleotides, or at least 50, 100, 200 or 300 amino acids), provided that the fragment retains the required activity when present in the antibody (e.g. specific binding to HMW-MAA and/or a Fcϵ receptor).

Variants of the above amino acid and nucleotide sequences may also be used in the present invention, provided that the resulting antibody binds HMW-MAA and a Fcϵ receptor. Typically such variants have a high degree of sequence identity with one of the sequences specified above.

The similarity between amino acid or nucleotide sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of the amino acid or nucleotide sequence will possess a relatively high degree of sequence identity when aligned using standard methods.

Methods of alignment of sequences for comparison are well known in the art. Various programs and alignment algorithms are described in: Smith and Waterman, Adv. Appl. Math. 2:482, 1981; Needleman and Wunsch, J. Mol. Biol. 48:443, 1970; Pearson and Lipman, Proc. Natl. Acad. Sci. U.S.A. 85:2444, 1988; Higgins and Sharp, Gene 73:237, 1988; Higgins and Sharp, CABIOS 5:151, 1989; Corpet et al., Nucleic Acids Research 16:10881, 1988; and Pearson and Lipman, Proc. Natl. Acad. Sci. U.S.A. 85:2444, 1988. Altschul et al., Nature Genet. 6:119, 1994, presents a detailed consideration of sequence alignment methods and homology calculations.

The NCBI Basic Local Alignment Search Tool (BLAST) (Altschul et al., J. Mol. Biol. 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of the anti-HMW-MAA antibody or a domain thereof (e.g. a VL, VH, CL or CH domain) typically have at least about 75%, for example at least about 80%, 90%, 95%, 96%, 97%, 98% or 99% sequence identity with the original sequence (e.g. a sequence defined above), for example counted over the full length alignment with the amino acid sequence of the antibody or domain thereof using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Typically variants may contain one or more conservative amino acid substitutions compared to the original amino acid or nucleic acid sequence. Conservative substitutions are those substitutions that do not substantially affect or decrease the affinity of an antibody to HMW-MAA and/or Fcϵ receptors. For example, a human antibody that specifically binds HMW-MAA may include up to 1, up to 2, up to 5, up to 10, or up to 15 conservative substitutions compared to the original sequence (e.g. as defined above) and retain specific binding to the HMW-MAA polypeptide. The term conservative variation also includes the use of a substituted amino acid in place of an unsubstituted parent amino acid, provided that antibody specifically binds HMW-MAA. Non-conservative substitutions are those that reduce an activity or binding to HMW-MAA and/or Fcϵ receptors.

Functionally similar amino acids which may be exchanged by way of conservative substitution are well known to one of ordinary skill in the art. The following six groups are examples of amino acids that are considered to be conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

Production of Anti-HMW-MAA Antibodies and Nucleic Acids

Nucleic acid molecules (also referred to as polynucleotides) encoding the polypeptides provided herein (including, but not limited to antibodies and functional fragments thereof) can readily be produced by one of skill in the art, using the amino acid sequences provided herein, sequences available in the art, and the genetic code. In addition, one of skill can readily construct a variety of clones containing functionally equivalent nucleic acids, such as nucleic acids which differ in sequence but which encode the same effector molecule or antibody sequence. Thus, nucleic acids encoding antibodies are provided herein.

Nucleic acid sequences encoding the antibodies that specifically bind HMW-MAA, or functional fragments thereof that specifically bind HMW-MAA, can be prepared by any suitable method including, for example, cloning of appropriate sequences or by direct chemical synthesis by methods such as the phosphotriester method of Narang et al., Meth. Enzymol. 68:90-99, 1979; the phosphodiester method of Brown et al., Meth. Enzymol. 68:109-151, 1979; the diethylphosphoramidite method of Beaucage et al., Tetra. Lett. 22:1859-1862, 1981; the solid phase phosphoramidite triester method described by Beaucage & Caruthers, Tetra. Letts. 22(20):1859-1862, 1981, for example, using an automated synthesizer as described in, for example, Needham-VanDevanter et al., Nucl. Acids Res. 12:6159-6168, 1984; and, the solid support method of U.S. Pat. No. 4,458,066. Chemical synthesis produces a single stranded oligonucleotide. This can be converted into double stranded DNA by hybridization with a complementary sequence or by polymerization with a DNA polymerase using the single strand as a template. One of skill would recognize that while chemical synthesis of DNA is generally limited to sequences of about 100 bases, longer sequences may be obtained by the ligation of shorter sequences.

Exemplary nucleic acids encoding antibodies that specifically bind HMW-MAA, or functional fragments thereof that specifically bind HMW-MAA, can be prepared by cloning techniques. Examples of appropriate cloning and sequencing techniques, and instructions sufficient to direct persons of skill through many cloning exercises are found see, for example, Molecular Cloning: A Laboratory Manual, 2nd ed., vol. 1-3, ed. Sambrook et al., Cold Spring Harbor Laboratory Press, Cold Spring Harbor, N.Y., 1989); and Current Protocols in Molecular Biology (Ausubel et al., eds 1995 supplement)). Product information from manufacturers of biological reagents and experimental equipment also provide useful information. Such manufacturers include the SIGMA Chemical Company (Saint Louis, Mo.), R&D Systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (Carlsbad, Calif.), and Applied Biosystems (Foster City, Calif.), as well as many other commercial sources known to one of skill.

Nucleic acids encoding native anti-HMW-MAA antibodies can be modified to faun the antibodies described herein. Modification by site-directed mutagenesis is well known in the art. Nucleic acids can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill.

In one embodiment, antibodies are prepared by inserting a cDNA which encodes one or more antibody domains (e.g. a mouse IgG1 heavy chain variable region which binds human HMW-MAA) into a vector which comprises a cDNA encoding one or more further antibody domains (e.g. a human heavy chain ϵ constant region). The insertion is made so that the antibody domains are read in frame, that is in one continuous polypeptide which contains a functional antibody region.

In one embodiment, cDNA encoding a heavy chain constant region is ligated to a heavy chain variable region so that the constant region is located at the carboxyl terminus of the antibody. The heavy chain-variable and/or constant regions can subsequently be ligated to a light chain variable and/or constant region of the antibody using disulfide bonds.

Once the nucleic acids encoding the anti-HMW-MAA antibody or functional fragment thereof have been isolated and cloned, the desired protein can be expressed in a recombinantly engineered cell such as bacteria, plant, yeast, insect and mammalian cells. It is expected that those of skill in the art are knowledgeable in the numerous expression systems available for expression of proteins including *E. coli*, other bacterial hosts, yeast, and various higher eukaryotic cells such as the COS, CHO, HeLa and myeloma cell lines.

One or more DNA sequences encoding the antibody or fragment thereof can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art. Hybridomas expressing the antibodies of interest are also encompassed by this disclosure.

The expression of nucleic acids encoding the isolated antibodies and antibody fragments described herein can be achieved by operably linking the DNA or cDNA to a promoter (which is either constitutive or inducible), followed by incorporation into an expression cassette. The cassettes can be suitable for replication and integration in either prokaryotes or eukaryotes. Typical expression cassettes contain specific sequences useful for regulation of the expression of the DNA encoding the protein. For example, the expression cassettes can include appropriate promoters, enhancers, transcription and translation terminators, initiation sequences, a start codon (i.e., ATG) in front of a protein-encoding gene, splicing signal for introns, maintenance of the correct reading frame of that gene to permit proper translation of mRNA, and stop codons.

To obtain high level expression of a cloned gene, it is desirable to construct expression cassettes which contain, at the minimum, a strong promoter to direct transcription, a ribosome binding site for translational initiation, and a transcription/translation terminator. For *E. coli*, this includes a promoter such as the T7, trp, lac, or lambda promoters, a ribosome binding site, and preferably a transcription termination signal. For eukaryotic cells, the control sequences can include a promoter and/or an enhancer derived from, for example, an immunoglobulin gene, SV40 or cytomegalovirus, and a polyadenylation sequence, and can further include splice donor and acceptor sequences. The cassettes can be transferred into the chosen host cell by well-known methods such as transformation or electroporation for *E. coli* and calcium phosphate treatment, electroporation or lipofection for mammalian cells. Cells transformed by the cassettes can be selected by resistance to antibiotics conferred by genes contained in the cassettes, such as the amp, gpt, neo and hyg genes.

When the host is a eukaryote, such methods of transfection of DNA as calcium phosphate coprecipitates, conventional mechanical procedures such as microinjection, electroporation, insertion of a plasmid encased in liposomes, or virus vectors may be used. Eukaryotic cells can also be co-transformed with polynucleotide sequences encoding the antibody, labelled antibody, or functional fragment thereof, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, Eukaryotic Viral Vectors, Cold Spring Harbor Laboratory, Gluzman ed., 1982). One of skill in the art can readily use an expression systems such as plasmids and vectors of use in producing proteins in cells including higher eukaryotic cells such as the COS, CHO, HeLa and myeloma cell lines.

Modifications can be made to a nucleic acid encoding a polypeptide described herein (i.e., a human HMW-MAA-specific monoclonal antibody) without diminishing its biological activity. Some modifications can be made to facilitate the cloning, expression, or incorporation of the targeting molecule into a fusion protein. Such modifications are well known to those of skill in the art and include, for example, termination codons, a methionine added at the amino terminus to provide an initiation, site, additional amino acids placed on either terminus to create conveniently located restriction sites, or additional amino acids (such as poly His) to aid in purification steps. In addition to recombinant methods, the antibodies of the present disclosure can also be constructed in whole or in part using standard peptide synthesis well known in the art.

Once expressed, the recombinant antibodies can be purified according to standard procedures of the art, including ammonium sulfate precipitation, affinity columns, column chromatography, and the like (see, generally, R. Scopes, PROTEIN PURIFICATION, Springer-Verlag, N.Y., 1982). The antibodies, immunoconjugates and effector molecules need not be 100% pure. Once purified, partially or to homogeneity as desired, if to be used therapeutically, the polypeptides should be substantially free of endotoxin.

Methods for expression of single chain antibodies and/or refolding to an appropriate active form, including single chain antibodies, from bacteria such as *E. coli* have been described and are well-known and are applicable to the antibodies disclosed herein. See, Buchner et al., Anal. Biochem. 205:263-270, 1992; Pluckthun, Biotechnology 9:545, 1991; Huse et al., Science 246:1275, 1989 and Ward et al., Nature 341:544, 1989.

Often, functional heterologous proteins from *E. coli* or other bacteria are isolated from inclusion bodies and require solubilization using strong denaturants, and subsequent refolding. During the solubilization step, as is well known in the art, a reducing agent must be present to separate disulfide bonds. An exemplary buffer with a reducing agent is: 0.1 M Tris pH 8, 6 M guanidine, 2 mM EDTA, 0.3 M DTE (dithioerythritol). Reoxidation of the disulfide bonds can occur in the presence of low molecular weight thiol reagents in reduced and oxidized form, as described in Saxena et al., Biochemistry 9: 5015-5021, 1970, and especially as described by Buchner et al., supra.

Renaturation is typically accomplished by dilution (for example, 100-fold) of the denatured and reduced protein into refolding buffer. An exemplary buffer is 0.1 M Tris, pH 8.0, 0.5 M L-arginine, 8 mM oxidized glutathione (GSSG), and 2 mM EDTA.

As a modification to the two chain antibody purification protocol, the heavy and light chain regions are separately solubilized and reduced and then combined in the refolding solution. An exemplary yield is obtained when these two proteins are mixed in a molar ratio such that a 5 fold molar excess of one protein over the other is not exceeded. Excess oxidized glutathione or other oxidizing low molecular weight compounds can be added to the refolding solution after the redox-shuffling is completed.

In addition to recombinant methods, the antibodies, labelled antibodies and functional fragments thereof that are disclosed herein can also be constructed in whole or in part using standard peptide synthesis. Solid phase synthesis of the polypeptides of less than about 50 amino acids in length can be accomplished by attaching the C-terminal amino acid of the sequence to an insoluble support followed by sequential addition of the remaining amino acids in the sequence. Techniques for solid phase synthesis are described by Barany & Merrifield, The Peptides: Analysis, Synthesis, Biology. Vol. 2: Special Methods in Peptide Synthesis, Part A. pp. 3-284; Merrifield et al., J. Am. Chem. Soc. 85:2149-2156, 1963, and Stewart et al., Solid Phase Peptide Synthesis, 2nd ed., Pierce Chem. Co., Rockford, Ill., 1984. Proteins of greater length may be synthesized by condensation of the amino and carboxyl termini of shorter fragments.

Methods of forming peptide bonds by activation of a carboxyl terminal end (such as by the use of the coupling reagent N,N'-dicylohexylcarbodimide) are well known in the art.

In one embodiment, the antibodies, nucleic acids, expression vectors, host cells or other biological products are isolated. By "isolated" it is meant that the product has been substantially separated or purified away from other biological components in the environment (such as a cell) in which the component naturally occurs, i.e., other chromosomal and extra-chromosomal DNA and RNA, proteins and organelles. Nucleic acids and antibodies that have been "isolated" include nucleic acids and antibodies purified by standard purification methods. The term also embraces nucleic acids and antibodies prepared by recombinant expression in a host cell as well as chemically synthesized nucleic acids.

Immunoconjugates Comprising Anti-HMW-MAA Antibodies

The antibodies, or functional fragments thereof, that specifically bind HMW-MAA can be used in therapeutic methods. In several embodiments, the antibodies or functional fragments thereof described herein can be conjugated to a therapeutic agent. Immunoconjugates include, but are not limited to, molecules in which there is a covalent linkage of a therapeutic agent to an antibody. A therapeutic agent is an agent with a particular biological activity directed against a particular target molecule or a cell bearing a target molecule. One of skill in the art will appreciate that therapeutic agents can include various drugs such as vinblastine, daunomycin and the like, cytotoxins such as native or modified *Pseudomonas* exotoxin or Diphtheria toxin, encapsulating agents (such as liposomes) which themselves contain pharmacological compositions, radioactive agents such as $^{125}I$, $^{32}P$, $^{14}C$, $^{3}H$ and $3^{5}S$ and other labels, target moieties and ligands.

The choice of a particular therapeutic agent depends on the particular target molecule or cell, and the desired biological effect. Thus, for example, the therapeutic agent can be a cytotoxin that is used to bring about the death of a particular target cell. Conversely, where it is desired to invoke a non-lethal biological response, the therapeutic agent can be conjugated to a non-lethal pharmacological agent or a liposome containing a non-lethal pharmacological agent.

With the therapeutic agents and antibodies described herein, one of skill can readily construct a variety of clones containing functionally equivalent nucleic acids, such as nucleic acids which differ in sequence but which encode the same EM or antibody sequence. Thus, the present invention provides nucleic acids encoding antibodies and conjugates and fusion proteins thereof.

Effector molecules can be linked to an antibody of interest using any number of means known to those of skill in the art. Both covalent and noncovalent attachment means may be used. The procedure for attaching an effector molecule to an antibody varies according to the chemical structure of the effector. Polypeptides typically contain a variety of functional groups; such as carboxylic acid (—COOH), free amine (—NH2) or sulfhydryl (—SH) groups, which are available for reaction with a suitable functional group on an antibody to result in the binding of the effector molecule. Alternatively, the antibody is derivatized to expose or attach additional reactive functional groups. The derivatization may involve attachment of any of a number of linker molecules such as those available from Pierce Chemical Company, Rockford, Ill. The linker can be any molecule used to join the antibody to the effector molecule. The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (such as through a disulfide linkage to cysteine) or to the alpha carbon amino and carboxyl groups of the terminal amino acids.

In some circumstances, it is desirable to free the effector molecule from the antibody when the immunoconjugate has reached its target site. Therefore, in these circumstances, immunoconjugates will comprise linkages that are cleavable in the vicinity of the target site. Cleavage of the linker to release the effector molecule from the antibody may be prompted by enzymatic activity or conditions to which the immunoconjugate is subjected either inside the target cell or in the vicinity of the target site.

In view of the large number of methods that have been reported for attaching a variety of radiodiagnostic compounds, radiotherapeutic compounds, label (such as enzymes or fluorescent molecules) drugs, toxins, and other agents to antibodies one skilled in the art will be able to determine a suitable method for attaching a given agent to an antibody or other polypeptide.

The antibodies or antibody fragments that specifically bind HMW-MAA disclosed herein can be derivatized or linked to another molecule (such as another peptide or protein). In general, the antibodies or portion thereof is derivatized such that the binding to HMW-MAA is not affected adversely by the derivatization or labeling. For example, the antibody can be functionally linked (by chemical coupling, genetic fusion, noncovalent association or otherwise) to one or more other molecular entities, such as another antibody (for example, a bispecific antibody or a diabody), a detection agent, a pharmaceutical agent, and/or a protein or peptide that can mediate associate of the antibody or antibody portion with another molecule (such as a streptavidin core region or a polyhistidine tag).

One type of derivatized antibody is produced by crosslinking two or more antibodies (of the same type or of different types, such as to create bispecific antibodies). Suitable crosslinkers include those that are heterobifunctional, having two distinctly reactive groups separated by an appropriate spacer (such as m-maleimidobenzoyl-N-hydroxysuccinimide ester) or homobifunctional (such as disuccinimidyl suberate). Such linkers are available from Pierce Chemical Company, Rockford, Ill.

An antibody that specifically binds HMW-MAA or functional fragment thereof can be labeled with a detectable moiety. Useful detection agents include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, Green fluorescent protein (GFP), Yellow fluorescent protein (YFP). An antibody can also be labeled with enzymes that are useful for detection, such as horseradish peroxidase, beta -galactosidase, luciferase, alkaline phosphatase, glucose oxidase and the like.

When an antibody is labeled with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. An antibody may also be labeled with biotin, and detected through indirect measurement of avidin or streptavidin binding. It should be noted that the avidin itself can be labeled with an enzyme or a fluorescent label.

An antibody may be labeled with a magnetic agent, such as gadolinium. Antibodies can also be labeled with lanthanides (such as europium and dysprosium), and manganese. Paramagnetic particles such as superparamagnetic iron oxide are also of use as labels. An antibody may also be labeled with a predetermined polypeptide epitopes recognized by a secondary reporter (such as leucine zipper pair sequences, binding sites for secondary antibodies, metal binding domains, epitope tags). In some embodiments, labels are attached by spacer arms of various lengths to reduce potential steric hindrance.

An antibody can also be labeled with a radiolabel, e.g. a radiolabeled amino acid. The radiolabel may be used for both diagnostic and therapeutic purposes. For instance, the radiolabel may be used to detect HMW-MAA by x-ray, emission spectra, magnetic resonance imaging (MRI), commuted tomography (CT) scan, positron emission tomography (PET), or other diagnostic techniques. Examples of labels for polypeptides include, but are not limited to, the following radioisotopes or radionucleotides: $^{35}$F, $^{11}$C, $^{13}$N, $^{15}$O, $^{18}$F, $^{19}$F, $^{99m}$Tc, $^{131}$I, $^{3}$H, $^{14}$C, $^{15}$N, $^{90}$Y, $^{99}$Tc, $^{111}$In, and $^{125}$I.

Labelled antibodies can be used in a variety of immunoassays, including Fluorescence activated cells sorting (FACS), immunohistochemistry, radioimmune assays (RIAs), and enzyme-linked immunosorbant assays (ELISA). Means of detecting such labels are well known to those of skill in the art. Thus, for example, radiolabels may be detected using photographic film or scintillation counters, fluorescent markers may be detected using a photodetector to detect emitted illumination.

An antibody can also be derivatized with a chemical group such as polyethylene glycol (PEG), a methyl or ethyl group, or a carbohydrate group. These groups may be useful to improve the biological characteristics of the antibody, such as to increase serum half-life or to increase tissue binding.

Toxins can be employed with the HMW-MAA-specific antibodies, and functional fragments thereof, that are described herein, to produce immunotoxins. Exemplary toxins include ricin, abrin, diphtheria toxin and subunits thereof, as well as botulinum toxins A through F. These toxins are readily available from commercial sources (for example, Sigma Chemical Company, St. Louis, Mo.). Contemplated toxins also include variants of the toxins described herein (see, for example, see, U.S. Pat. Nos. 5,079,163 and 4,689,401). In one embodiment, the toxin is *Pseudomonas* exotoxin (PE) (U.S. Pat. No. 5,602,095). As used herein "*Pseudomonas* exotoxin" refers to a full-length native (naturally occurring) PE or a PE that has been modified. Such modifications can include, but are not limited to, elimination of domain Ia, various amino acid deletions in domains Ib, II and III, single amino acid substitutions and the addition of one or more sequences at the carboxyl terminus (for example, see Siegall et al., J. Biol. Chem. 264:14256-14261, 1989). In one embodiment, the cytotoxic fragment of PE retains at least 50%, at least 75%, at least 90%, or at lest 95% of the cytotoxicity of native PE. In some examples, the cytotoxic fragment is more toxic than native PE.

Native *Pseudomonas* exotoxin A (PE) is an extremely active monomeric protein (molecular weight 66 kD), secreted by *Pseudomonas aeruginosa*, which inhibits protein synthesis in eukaryotic cells. The method of PE action is inactivation of the ADP-ribosylation of elongation factor 2 (EF-2). The exotoxin contains three structural domains that act in concert to cause cytotoxicity. Domain 1a mediates cell binding. Domain II is responsible for translocation into the cytosol and domain III mediates ADP ribosylation of elongation factor 2. The function of domain 1b is unknown. PE employed with the monoclonal antibodies described herein can include the native sequence, cytotoxic fragments of the native sequence, and conservatively modified variants of native PE and its cytotoxic fragments. Cytotoxic fragments of PE include those which are cytotoxic with or without subsequent proteolytic or other processing in the target cell. Cytotoxic fragments of PE include PE40, PE38, and PE35. For additional description of PE and variants thereof, see for example, U.S. Pat. Nos. 4,892,827; 5,512,658; 5,602,095; 5,608,039; 5,821,238; and 5,854,044; WO 99/51643; Pai et al., Proc. Natl. Acad. Sci. USA 88:3358-3362, 1991; Kondo et al., J. Biol. Chem. 263:9470-9475, 1988; Pastan et al., Biochim. Biophys. Acta 1333:C1-C6, 1997.

The antibodies and functional fragments thereof described herein can also be used to target any number of different diagnostic or therapeutic compounds to cells expressing HMW-MAA on their surface. Thus, an antibody of the present disclosure can be attached directly or via a linker to a drug that is to be delivered directly to cells expressing cell-surface HMW-MAA. Therapeutic agents include such compounds as nucleic acids, proteins, peptides, amino acids or derivatives, glycoproteins, radioisotopes, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides.

Alternatively, the molecule linked to an anti-HMW-MAA antibody can be an encapsulation system, such as a liposome or micelle that contains a therapeutic composition such as a drug, a nucleic acid (for example, an antisense nucleic acid), or another therapeutic moiety that is preferably shielded from direct exposure to the circulatory system. Means of preparing liposomes attached to antibodies are well known to those of skill in the art (see, for example, U.S. Pat. No. 4,957,735; Connor et al., Pharm. Ther. 28:341-365, 1985).

Compositions and Therapeutic Methods

Compositions are provided herein that include a carrier and one or more antibodies that specifically bind HMW-MAA, or functional fragments thereof that specifically binds HMW-MAA. The compositions can be prepared in unit dosage forms for administration to a subject. The amount and timing of administration are at the discretion of the treating physician to achieve the desired purposes. The antibody can be formulated for systemic or local (such as intra-tumour) administration. In one example, the antibody that specifically binds HMW-MAA is formulated for parenteral administration, such as intravenous administration.

The compositions for administration can include a solution of the antibody that specifically binds HMW-MAA (or a functional fragment thereof) dissolved in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibody in these formulations can vary widely, and will be selected primarily based on fluid volumes, viscosities, body weight and the like in accordance with the particular mode of administration selected and the subject's needs.

A typical dose of the pharmaceutical composition for intravenous administration includes about 0.1 to 15 mg of antibody per kg body weight of the subject per day. Dosages from 0.1 up to about 100 mg per kg per day may be used, particularly if the agent is administered to a secluded site and not into the circulatory or lymph system, such as into a body cavity or into a lumen of an organ. Actual methods for preparing administrable compositions will be known or apparent to those skilled in the art and are described in more detail in such publications as Remington's Pharmaceutical Science, 19th ed., Mack Publishing Company, Easton, Pa. (1995).

Antibodies may be provided in lyophilized form and rehydrated with sterile water before administration, although they are also provided in sterile solutions of known concentration. The antibody solution is then added to an infusion bag containing 0.9% sodium chloride, USP, and typically administered at a dosage of from 0.5 to 15 mg/kg of body weight. Considerable experience is available in the art in the administration of antibody drugs, which have been marketed in the U.S. since the approval of RITUXAN (Registered trademark) in 1997. Antibodies can be administered by slow infusion, rather than in an intravenous push or bolus. In one example, a higher loading dose is administered, with subsequent, maintenance doses being administered at a lower level. For example, an initial loading dose of 4 mg/kg may be infused over a period of some 90 minutes, followed by weekly maintenance doses for 4-8 weeks of 2 mg/kg infused over a 30 minute period if the previous dose was well tolerated.

The antibody that specifically binds HMW-MAA (or functional fragment thereof) can be administered to slow or inhibit the growth of cells, such as cancer cells. In these applications, a therapeutically effective amount of an antibody is administered to a subject in an amount sufficient to inhibit growth, replication or metastasis of cancer cells, or to inhibit a sign or a symptom of the cancer. In some embodiments, the antibodies are administered to a subject to inhibit or prevent the development of metastasis, or to decrease the size or number of metasases, such as micrometastases, for example micrometastases to the regional lymph nodes (Goto et al., Clin. Cancer Res. 14(11):3401-3407, 2008).

Suitable subjects may include those diagnosed with a cancer that expresses HMW-MAA, such as, but not limited to, melanoma, prostate cancer, squamous cell carcinoma (such as head and neck squamous cell carcinoma), breast cancer (including, but not limited to basal breast carcinoma, ductal carcinoma and lobular breast carcinoma), leukemia (such as acute myelogenous leukemia and 11g23-positive acute leukemia), a neural crest tumour (such as an astrocytoma, glioma or neuroblastoma), ovarian cancer, colon cancer, stomach cancer, pancreatic cancer, bone cancer (such as a chordoma), glioma or a sarcoma (such as chondrosarcoma). Preferably the antibody is administered to treat a solid tumour. More preferably the antibody is administered to a subject suffering from skin cancer, e.g. malignant melanoma.

A therapeutically effective amount of a HMW-MAA-specific antibody will depend upon the severity of the disease and the general state of the patient's health. A therapeutically effective amount of the antibody is that which provides either subjective relief of a symptom(s) or an objectively identifiable improvement as noted by the clinician or other qualified observer. These compositions can be administered in conjunction with another chemotherapeutic agent, either simultaneously or sequentially.

Many chemotherapeutic agents are presently known in the art. In one embodiment, the chemotherapeutic agents is selected from the group consisting of mitotic inhibitors, alkylating agents, anti-metabolites, intercalating antibiotics, growth factor inhibitors, cell cycle inhibitors, enzymes, topoisomerase inhibitors, anti-survival agents, biological response modifiers, anti-hormones, e.g. anti-androgens, and anti-angiogenesis agents.

Anti-angiogenesis agents, such as MMP-2 (matrix-metalloproteinase 2) inhibitors, MMP-9 (matrix-metalloproteinase 9) inhibitors, and COX-II (cyclooxygenase II) inhibitors, can be used in conjunction with a compound of the invention. Examples of useful COX-II inhibitors include CELEBREX (Registered Trademark) (alecoxib), valdecoxib, and rofecoxib. Examples of useful matrix metalloproteinase inhibitors are described in WO 96/33172, WO 96/27583, WO 98/07697, WO 98/03516, WO 98/34918, WO 98/34915, WO 98/33768, WO 98/30566, EP606,046, EP931,788, WO 90/05719, WO 99/52910, WO 99/52889, WO 99/29667, U.S. Pat. No. 5,863,949, U.S. Pat. No. 5,861,510 and EP780,386.

In one example, the MMP inhibitors do not induce arthralgia upon administration. In another example, the MMP inhibitor selectively inhibits MMP-2 and/or MMP-9 relative to the other matrix-metalloproteinases (such as MMP-1, MMP-3, MMP-4, MMP-5, MMP-6, MMP-7, MMP-8, MMP-10, MMP-11, MMP-12, and MMP-13). Some specific examples of MMP inhibitors of use are AG-3340, RO 32-3555, RS 13-0830, 3-[[4-(4-fluoro-phenoxy)-benzenesulfonyl]-(1-hydroxycarbamoyl-cyclopentyl)-amino]-propionic acid; 3-exo-3-[4-(4-fluoro-phenoxy)-benzenesulfonylamino]-8-oxa-bicyclo[3.2.1]octane-3-carboxylic acid hydroxyamide; (2R,3R) 1-[4-(2-chloro-4-fluoro-benzyloxy)-benzenesulfonyl]-3-hydroxy-3-methyl-piperidine-2-carboxylic acid hydroxyamide; 4-[4-(4-fluoro-phenoxy)-benzenesulfonylamino]-tetrahydro-pyran-4-carboxylic acid hydroxyamide; 3-[[4-(4-fluoro-phenoxy)-benzenesulfonyl]-(1-hydroxycarbamoyl-cyclobutyl)-amino]-propionic acid; 4-[4-(4-chloro-phenoxy)-benzenesulfonylamino]-tetrahydro-pyran-4-carboxylic acid hydroxyamide; (R) 3-[[4-(4-chloro-phenoxy)-benzenesulfonylamino]-tetrahydro-pyran-3-carboxylic acid hydroxyamide; (2R,3R) 1-[4-(4-fluoro-2-methyl-benzyloxy)-benzenesulfonyl]-3-hydroxy-3-methyl-piperidine-2-carboxylic acid hydroxyamide; 3-[[4-(4-fluoro-phenoxy)-benzenesulfonyl]-(1-hydroxycarbamoyl-1-methyl-ethyl)-amino]-propionic acid; 3-[[4-(4-fluoro-phenoxy)-benzenesulfonyl]-(4-hydroxycarbamoyl-tetrahydro-pyran-4-yl)-amino]-propionic acid; 3-exo-3-[4-(4-chloro-phenoxy)-benzenesulfonylamino]-8-oxaicyclo[3.2.1]octane-3-carboxylic acid hydroxyamide; 3-endo-3-[4-(4-fluoro-phenoxy)-benzenesulfonylamino]-8-oxa-icyclo[3.2.1]octane-3-carboxylic acid hydroxyamide; and (R) 3-[4-(4-fluoro-phenoxy)-benzenesulfonylamino]-tetrahydro-furan-3-carboxylic acid hydroxyamide; and pharmaceutically acceptable salts and solvates of said compounds.

The antibodies that specifically bind HMW-MAA can also be used with signal transduction inhibitors, such as agents that can inhibit EGF-R (epidermal growth factor receptor) responses, such as EGF-R antibodies, EGF antibodies, and molecules that are EGF-R inhibitors; VEGF (vascular endothelial growth factor) inhibitors, such as VEGF receptors and molecules that can inhibit VEGF; and erbB2 receptor inhibitors, such as organic molecules or antibodies that bind to the erbB2 receptor, for example, HERCEPTIN (Registered Trademark) (Genentech, Inc.). EGF-R inhibitors are described in, for example in WO 95/19970, WO 98/14451, WO 98/02434, and U.S. Pat. No. 5,747,498. EGFR-inhibiting agents also include, but are not limited to, the monoclonal antibodies C225 and anti-EGFR 22Mab (ImClone Systems Incorporated), ABX-EGF (Abgenix/Cell Genesys), EMD-7200 (Merck KgaA), EMD-5590 (Merck KgaA), MDX-447/H-477 (Medarex Inc. and Merck KgaA), and the compounds ZD-1834, ZD-1838 and ZD-1839 (AstraZeneca), PKI-166 (Novartis), PKI-166/CGP-75166 (Novartis), PTK 787 (Novartis), CP 701 (Cephalon), leflunomide (Pharmacia/Sugen), CI-1033 (Warner Lambert Parke Davis), CI-1033/PD 183,805 (Warner Lambert Parke Davis), CL-387,785 (Wyeth-Ayerst), BBR-1611 (Boehringer Mannheim GmbH/Roche), Naamidine A (Bristol Myers Squibb), RC-3940-II (Pharmacia), BIBX-1382 (Boehringer Ingelheim), OLX-103 (Merck & Co.), VRCTC-310 (Ventech Research), EGF fusion toxin (Seragen Inc.), DAB-389 (Seragen/Lilgand), ZM-252808 (Imperial Cancer Research Fund), RG-50864 (INSERM), LFM-A12 (Parker Hughes Cancer Center), WH1-P97 (Parker Hughes Cancer Center), GW-282974 (Glaxo), KT-8391 (Kyowa Hakko) and EGF-R Vaccine (York Medical/Centro de Immunologia Molecular (CIM)).

VEGF inhibitors, for example SU-5416 and SU-6668 (Sugen Inc.), SH-268 (Schering), and NX-1838 (NeXstar) can also be used in conjunction with an antibody that specifically binds HMW-MAA. VEGF inhibitors are described in, for example in WO 99/24440, WO 95/21613, WO 99/61422, U.S. Pat. No. 5,834,504, WO 98/50356, U.S. Pat. Nos. 5,883,113, 5,886,020, 5,792,783, WO 99/10349, WO 97/32856, WO 97/22596, WO 98/54093, WO 98/02438, WO 99/16755 and WO 98/02437. Other examples of some specific VEGF inhibitors are IM862 (Cytran Inc.); anti-VEGF monoclonal antibody of Genentech, Inc.; and angiozyme, a synthetic ribozyme from Ribozyme and Chiron. These and other VEGF inhibitors can be used in conjunction with an antibody that specifically binds HMW-MAA.

ErbB2 receptor inhibitors, such as GW-282974 (Glaxo Wellcome plc), and the monoclonal antibodies AR-209

(Aronex Pharmaceuticals Inc.) and 2B-1 (Chiron), can furthermore be combined with the compound of the invention, for example those indicated in WO 98/02434, WO 99/35146, WO 99/35132, WO 98/02437, WO 97/13760, WO 95/19970, U.S. Pat. No. 5,587,458 and U.S. Pat. No. 5,877,305.

For the treatment of cancer, such as melanoma, the antibodies disclosed herein can be used with surgical treatment, or with another therapeutic including dacarbazine (also termed DTIC), or interleukin-2 (IL-2) or interferon, such as interferon-α2b (IFN-α2b), or bisphosphonates, such as zoledronate. For the treatment of a superficial melanoma, the antibodies can be used in conjunction with Imiquimod. For treatment of prostate cancer, the antibodies can be used in conjunction with, for example, surgery, radiation therapy, chemotherapy and hormonal therapy (such as anti-androgens or GnRH antagonists). For the treatment of HNSCC, the antibodies provided herein can be used in conjunction with surgery, radiation therapy, chemotherapy, other antibodies (such as cetuximab and bevacizumab) or small-molecule therapeutics (such as erlotinib).

Single or multiple administrations of the compositions are administered depending on the dosage and frequency as required and tolerated by the patient. In any event, the composition should provide a sufficient quantity of at least one of the antibodies (or functional fragments thereof) disclosed herein to effectively treat the patient. The dosage can be administered once but may be applied periodically until either a therapeutic result is achieved or until side effects warrant discontinuation of therapy. In one example, a dose of the antibody is infused for thirty minutes every other day. In this example, about one to about ten doses can be administered, such as three or six doses can be administered every other day. In a further example, a continuous infusion is administered for about five to about ten days. The subject can be treated at regular intervals, such as monthly, until a desired therapeutic result is achieved. Generally, the dose is sufficient to treat or ameliorate symptoms or signs of disease without producing unacceptable toxicity to the patient.

Controlled release parenteral formulations can be made as implants, oily injections, or as particulate systems. For a broad overview of protein delivery systems see, Banga, A. J., Therapeutic Peptides and Proteins: Formulation, Processing, and Delivery Systems, Technomic Publishing Company, Inc., Lancaster, Pa., (1995). Particulate systems include microspheres, microparticles, microcapsules, nanocapsules, nanospheres, and nanoparticles. Microcapsules contain the therapeutic protein, such as a cytotoxin or a drug, as a central core. In microspheres the therapeutic is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly. See, for example, Kreuter, J., Colloidal Drug Delivery Systems, J. Kreuter, ed., Marcel Dekker, Inc., New York, N.Y., pp. 219-342 (1994); and Tice & Tabibi, Treatise on Controlled Drug Delivery, A. Kydonieus, ed., Marcel Dekker, Inc. New York, N.Y., pp. 315-339, (1992).

Polymers can be used for ion-controlled release of the antibody compositions disclosed herein. Various degradable and nondegradable polymeric matrices for use in controlled drug delivery are known in the art (Langer, Accounts Chem. Res. 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., Pharm. Res. 9:425-434, 1992; and Pec et al., J. Parent. Sci. Tech. 44(2):58-65, 1990). Alternatively, hydroxyapatite has been used as a microcarrier for controlled release of proteins (Ijntema et al., Int. J. Pharm. 112:215-224, 1994). In yet another aspect, liposomes are used for controlled release as well as drug targeting of the lipid-capsulated drug (Betageri et al., Liposome Drug Delivery Systems, Technomic Publishing Co., Inc., Lancaster, Pa. (1993)). Numerous additional systems for controlled delivery of therapeutic proteins are known (see U.S. Pat. Nos. 5,055,303; 5,188,837; 4,235,871; 4,501,728; 4,837,028; 4,957,735; 5,019,369; 5,055,303; 5,514,670; 5,413,797; 5,268,164; 5,004,697; 4,902,505; 5,506,206; 5,271,961; 5,254,342 and 5,534,496).

Relative Therapeutic Efficacy of IgE and IgG Antibodies Against a Melanoma-Associated Antigen Therapeutic antibodies now complement conventional treatments of some malignant diseases and have improved prognosis for many cancer patients. More than half of antibodies are approved for the treatment of blood malignancies, but antibody treatments of solid, non-haematopoietic, tumours are urgently needed.

IgG is the only antibody class examined in the immunotherapy of cancer. Poor tissue penetration of IgG antibodies and low affinity of IgGs for their receptors on immune cells may partly account for the weak immune responses observed and resulting poor performance of many IgG antibodies against solid tumours.

IgE class antibodies play a major role in the human allergic response, but are also key contributors to the body's defence against parasitic infections. IgE antibodies naturally reside in tissues. They can be transported from the circulation into tissues, where, through their strong affinity for their receptors on immune cells, they are known to trigger powerful immune responses.

In embodiments of the present invention, the antibody is directed against the cell surface melanoma antigen HMW-MAA (high molecular weight melanoma associated antigen), which is over-expressed by >80% of melanomas, as a target for antibody immunotherapy. As demonstrated in the Example below, two chimaeric monoclonal antibodies (one IgG and one IgE) of the same specificity against HMW-MAA (each comprising the same variable region sequences of a mouse antibody) had differential effects in vivo. Due to differential immune effector cell-mediated melanoma tumour killing by each antibody, the IgE antibody had superior efficacy in an in vivo xenograft model of melanoma.

It has been surprisingly demonstrated herein that engineering antibodies with Fc regions of a different antibody class can improve antibody effector functions, if antibodies of this class can exert natural immune surveillance in anatomical locations where tumours may be found. This concept may be particularly relevant in the case of solid tumours, since these are frequently refractory to treatment with IgG antibodies. With a serum half-life of 21-24 days, compared to a half-life of 2-3 days in tissues, IgG antibodies may be the most effective antibody class to target blood-resident tumours and circulating tumour cells, while their ability to exert tumour surveillance in tissues may be less potent [18, 19]. Other parameters that may modulate IgG anti-tumoural functions could be slow or ineffective recruitment and/or local suppression of activator immune effector cells by tumour cells in lesions and the presence/induction of immunoregulatory cells by tumours in situ [20]. For antibodies of the IgG class that do localise in tumour lesions, overcoming these immunomodulatory environments may be challenging. Additionally, factors such as the low affinity of IgG for its Fc gamma receptors and the presence of the inhibitory receptor FcγRIIb in tumour-infiltrating immune cells such as macrophages may negatively influence the efficacy of IgG antibodies in tissues [21, 22].

Since each antibody class operates in different anatomic compartments, and functions through unique Fc-receptors and immune effector cells, we have focused on antibodies of the IgE class, commonly known for their role in the allergic response and parasite protection. Antibodies of this class function through their specific high-affinity Fc receptors on a different spectrum of effector cells to IgG, and naturally reside in tissues where they exert immunological surveillance. The results shown herein demonstrate that these properties may translate to superior efficacy in targeting tissue-resident tumours such as melanoma.

Advantages of IgE as an Antibody Therapy for the Treatment of Solid Tumours

Tissue Residency:

The concentration of IgE in the serum of normal individuals is minute (<150 ng/ml, i.e. 1/10,000 the concentration of IgG), and unlike IgG, the presence of IgE in the blood is short-lived (half-life of 1.5 days) [23, 24, 19]. Yet, IgE is sequestered in tissues and retained locally by powerful IgE receptor-expressing resident cells such as mast cells, macrophages and dendritic cells with a measured half-life of two weeks, proportionately longer than that of IgG (2-3 days) [24, 18].

High Affinity for IgE Receptors:

The affinity of IgE for its high-affinity receptor, FcεR1, ($K_a=10^{11}M^{-1}$) is $10^2$-$10^5$ times higher than that of IgGs for their receptors, making it the only antibody strongly retained by effector cells in the absence of antigen [23, 25, 19]. The slow dissociation of the IgE-FcεR1 complex and local retention of IgE in tissues may translate to lower effective therapeutic doses and/or reduced frequency of administration compared to IgG.

Lack of Inhibitory Receptor:

Unlike IgG, IgE is subject to no inhibitory receptor (cf. FcγRIIb), with the potential implication that the suppressive properties of tumour microenvironments may not bear as heavily on tumour-specific IgE effector functions against tissue resident tumours.

Tissue Resident Immune Effector Cells in Tumours:

A large proportion, as much as 50%, of tumour lesions are made up of infiltrating immune cells which are also concentrated round the tumours [26]. Some of these infiltrates are known powerful FcεR-expressing effector cells such as monocytes/macrophages, mast cells, dendritic cells and eosinophils. In the absence of tumour antigen-specific IgE, these cells may lack the required activity to target tumour cells due to immunosuppressive signals in the tumour microenvironment [27, 28].

Powerful Effector Functions:

IgE is extremely potent in recruiting and activating effector cells (T cells, monocytes, eosinophils, basophils) to the site of antigen challenge, through release of cytokines (IL-3, IL-4, IL-5, IL-6, IL-9, IL-13, GM-CSF and TNF-α), and also in activating these cells in situ. Mediators released by mast cells (histamine, leukotrienes and proteases) promote further recruitment and activation of blood effector cells [29]. In the context of their protective role in parasitic infections, IgE antibodies are known to trigger both antibody-mediated cellular cytotoxicity (ADCC), and antibody-mediated cellular phagocytosis of parasites [30-34]. Both IgE receptors are up-regulated by IgE and IL-4 on effector cells in situ, and are known to participate in these mechanisms of action.

These properties of IgE antibodies may be redirected to enhance cytotoxicity and phagocytosis of tumour cells, as well as initiate IgE antibody-dependent antigen presentation by IgE receptor-bearing antigen-presenting cells such as dendritic cells, B cells and macrophages. Thus, passive and active immunity against solid tumours could act in conjunction in tissues such as skin, naturally populated by IgE effector cells. The strength of IgE-mediated immune responses in tissues, then, carries the expectation of increased potency as well as longevity of immune surveillance by IgE and effector cells against skin tumours.

HMW-MAA is a Suitable Target for Antibody Immunotherapy

We have identified the high-molecular-weight melanoma-associated antigen (HMW-MAA) as an appropriate target for antibody immunotherapy. A cell surface chondroitin sulfate proteoglycan HMW-MAA is expressed by >80% of melanoma lesions, but not normal melanocytes. Its restricted distribution in normal tissues is well-documented (basal cells of the epidermis, epidermal and hair follicle progenitors, chondrocytes). Expression in primary and metastatic lesions and limited heterogeneity across tumours potentially render it a highly suitable therapeutic target [35]. Its presence in activated pericytes in tumour-associated angiogenic vasculature suggests a role in regulating and promoting tumour angiogenesis [36]. This could offer an additional advantage for antibody therapy, not only in targeting HMW-MAA-expressing tumour cells, but also in restricting angiogenesis and reducing tumour cell growth and migration. HMW-MAA enhances motility, migration and the metastatic capacity of melanoma cells by enhancing interactions with the extracellular matrix. It may also act as an auxiliary growth factor and has a role in melanoma cell proliferation. This gives the hope of preferential elimination of the more aggressive—that is to say, most proliferative and metastatic—HMW-MAA-expressing melanoma cells by specific antibodies. Pre-clinical and clinical studies have studied the efficacy of HMW-MAA-directed immunotherapy of melanoma. However, it has been suggested that mouse antibodies to HMW-MAA do not function by immunological mechanisms in vitro and in animal models [37], thus efforts to engineer derivatives that may trigger human Fc-expressing effector cell functions (i.e. cloning with human Fc regions) have not been disclosed.

mAb 225.28s: a Monoclonal Antibody Against HMW-MAA

In one embodiment, the antibody comprises an antigen-binding region derived from mAb 225.28s. The 225.28s monoclonal antibody is directed against HMW-MAA, and was developed in Prof. Soldano Ferrone's laboratory (now at University of Pittsburg, USA). The variable region sequences were published in 1996 by Neri et al, and the original mouse clone was made in a hybridoma format [38]. It has been established that the antibody binds with high affinity and high specificity to an epitope on the target protein, and that it is univalent—a requirement for safety in the context of an IgE therapeutic, as explained above. The efficacy of this clone was tested in a number of in vitro and in vivo models [39, 40].

Early in vitro studies indicate that the mouse 225.28s antibody clone provokes, though only weakly, both complement and cell-mediated melanoma cell toxicity. The evidence in fact suggests that the main mechanisms by which antibodies such as 225.28s developed against HMW MAA work are not immunological, for they are associated with reduced proliferation and neovascularisation, restriction of cell migration and metastasis. These mechanisms have recently been reported in the context of triple-negative breast cancer cells which express the antigen. Further studies have demonstrated the ability of the mouse 225.28s IgG antibody to suppress melanoma tumour growth in a human xenograft grown s.c. in SCID mice. Although the mechanisms of its function were not fully analysed, it was conceded by the authors that the restricted access of these (IgG class) antibodies to solid tissues was a likely explanation for the modest extent of tumour regressions observed. In a different model, the mouse IgG coupled to methotrexate, was active in targeting and inhibiting growth of a human melanoma xenograft, grown s.c. in nude mice. A toxin-conjugated derivative of 225.28s has reached clinical testing, and scFv derivatives have been designed [41, 42].

However, to-date, a molecule of this specificity has not been engineered into a chimaeric or humanised recombinant form. The mouse antibody clone suffers from two obvious disadvantages: a) mouse sequences are expected to induce HAMA (human anti-murine antibody) responses in patients, resulting in neutralisation of the antibody and rapid clearance from the circulation, thereby significantly reducing any efficacy against tumour cells, and b) an antibody with Fc regions of mouse origin is not expected to effectively recruit FcR-expressing human immune effector cells which may target and kill tumour cells by mechanisms such as cytotoxicity and/or phagocytosis. Therefore the potential therapeutic relevance of a recombinant agent with this specificity has not previously been proposed. Therefore as described in the Example below; we conducted a direct comparison, based on chimaeric 225.28s antibodies of different classes, IgG1 and IgE, and examine their potential efficacy in the treatment of melanoma.

The invention will now be further described with reference to the following non-limiting example.

EXAMPLE

Engineering of Melanoma Antigen-Specific Antibodies

Figure 1B:
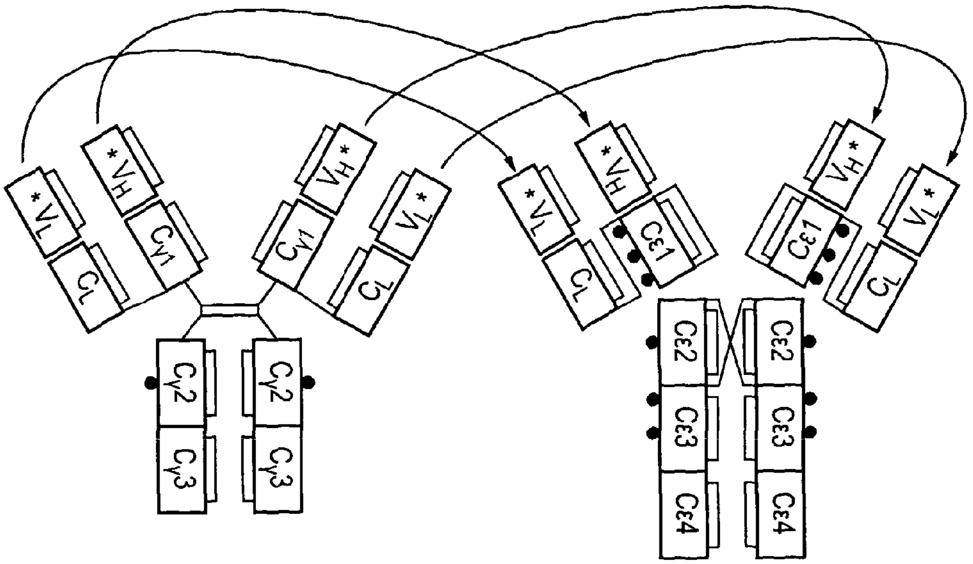

Engineering and Characterization of Chimaeric IgE and IgG1 Antibodies Recognising the HMW-MAA Antigen The system for expression cloning used in the present study allows production of antibodies of any class within a few weeks (see FIG. 1). Nucleotide sequences encoding the heavy and light chain variable regions of murine antibody clone 225.28s (see FIGS. 12 to 15, SEQ ID NO:s 3 to 6) were codon-optimised for expression in humans. The human codon-optimised sequences (shown in FIGS. 20 and 21, SEQ ID NO:s 11 and 12) were inserted into the human IgG1 and IgE heavy and kappa light chain vectors (comprising human IgG1 and IgE heavy and kappa light chain constant regions). The nucleotide sequence encoding the IgE heavy chain constant region is shown in FIG. 22 (SEQ ID NO:s 13 to 16) and the sequence encoding the kappa light chain constant region is shown in FIG. 23 (SEQ ID NO: 17). The heavy and light chain amino acid and nucleotide sequences of the resultant chimeric IgE antibody are shown in FIGS. 16 to 19 (SEQ ID NO:s 7 to 10). The vectors comprising the chimaeric sequences were used to transfect HEK297 cells with production efficiencies of up to 15-20 mg per litre of supernatant.

Figure 2:
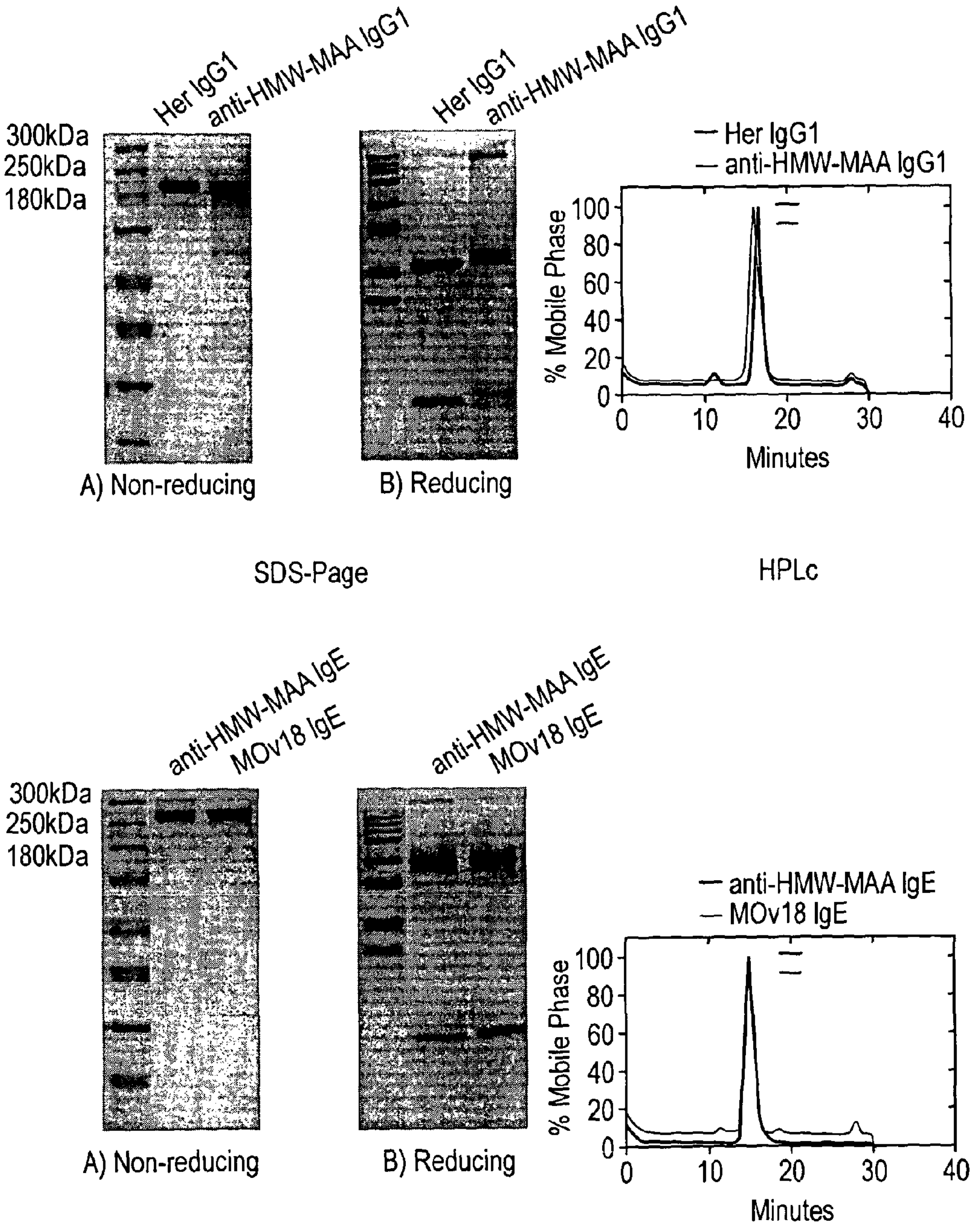
FIG. 2: Characterisation of the engineered HMW-MAA melanoma antigen-specific IgE (top panel) and $IgG_1$ (bottom panel) antibodies. Native (left) and reduced (middle) SDS polyacrylamide gel electrophoresis of HMW-MAA IgE (top) and $IgG_1$ (bottom) protein products, compared with the previously-characterised chimaeric antibodies MOv18 IgE and $IgG_1$. Right: Elution profiles of the affinity column-purified antibodies by size-exclusion chromatography analysis.

The antibodies were purified by routine methods previously published [43-47]. The biophysical properties of engineered chimaeric antibodies are routinely tested by gel electrophoresis and by HPLC size-exclusion chromatography analysis, and compared to previously tested MOv18 IgG1 and IgE antibodies raised against FRα, and also to clinical-grade Trastuzumab (Herceptin®, IgG1) (FIG. 2), to ascertain product quality and purity.

Figure 3A:
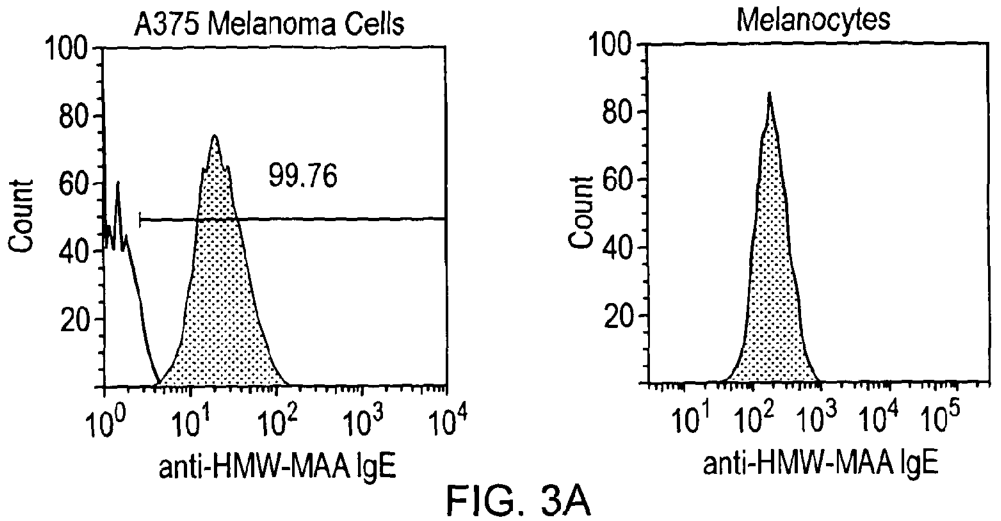
FIG. 3: Flow cytometric histograms showing HMW-MAA-IgE binding. A: Binding of chimaeric IgE to A375 melanoma tumour cells (left) but not to melanocytes (right). B: Binding of IgE to U937 monocytic cells (left) and to primary melanocytes (right). Antibody binding was detected using a goat anti-human IgE-FITC antibody. C: Flow cytometric histograms showing HMW-MAA-IgG binding to A375 melanoma tumour cells (left) and U937 monocytic cells (right). Antibody binding was detected using a goat anti-human IgG-FITC antibody.
Figure 3B:
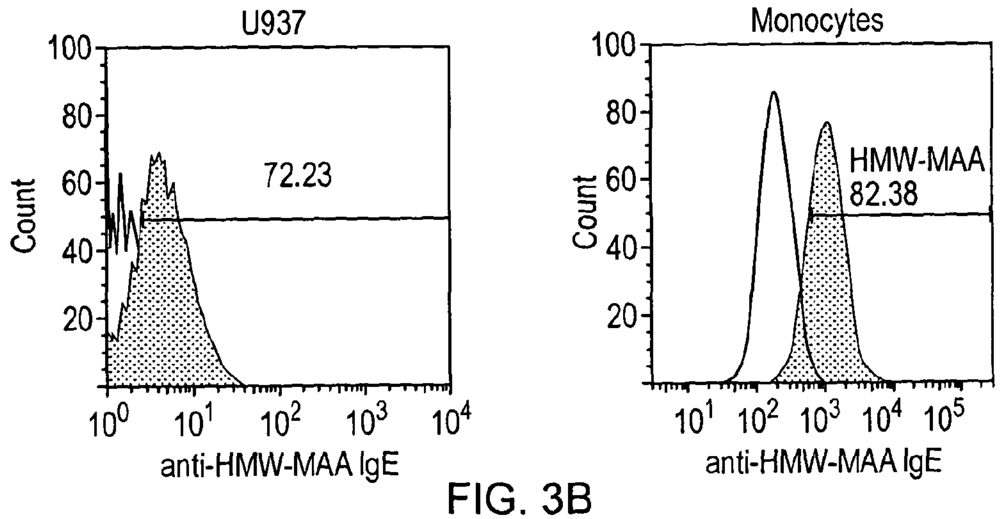
Figure 3C:
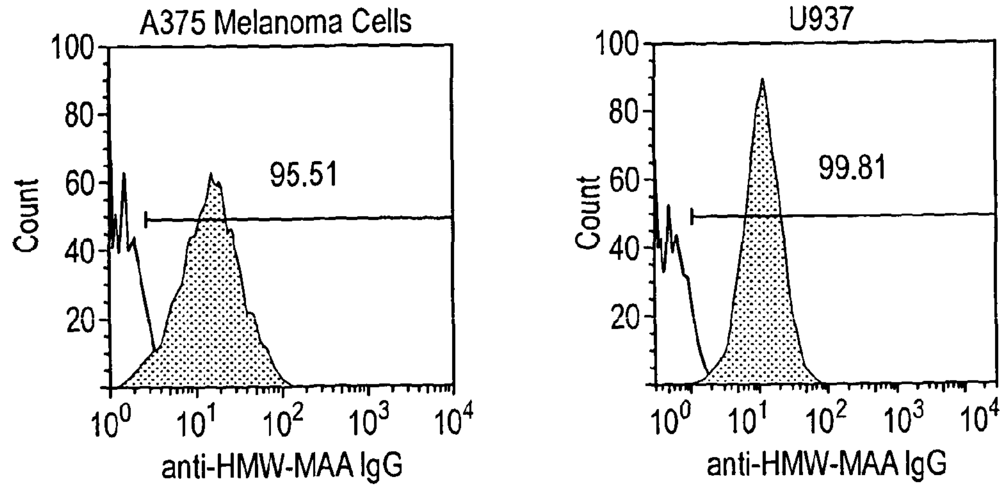
Figure 4:
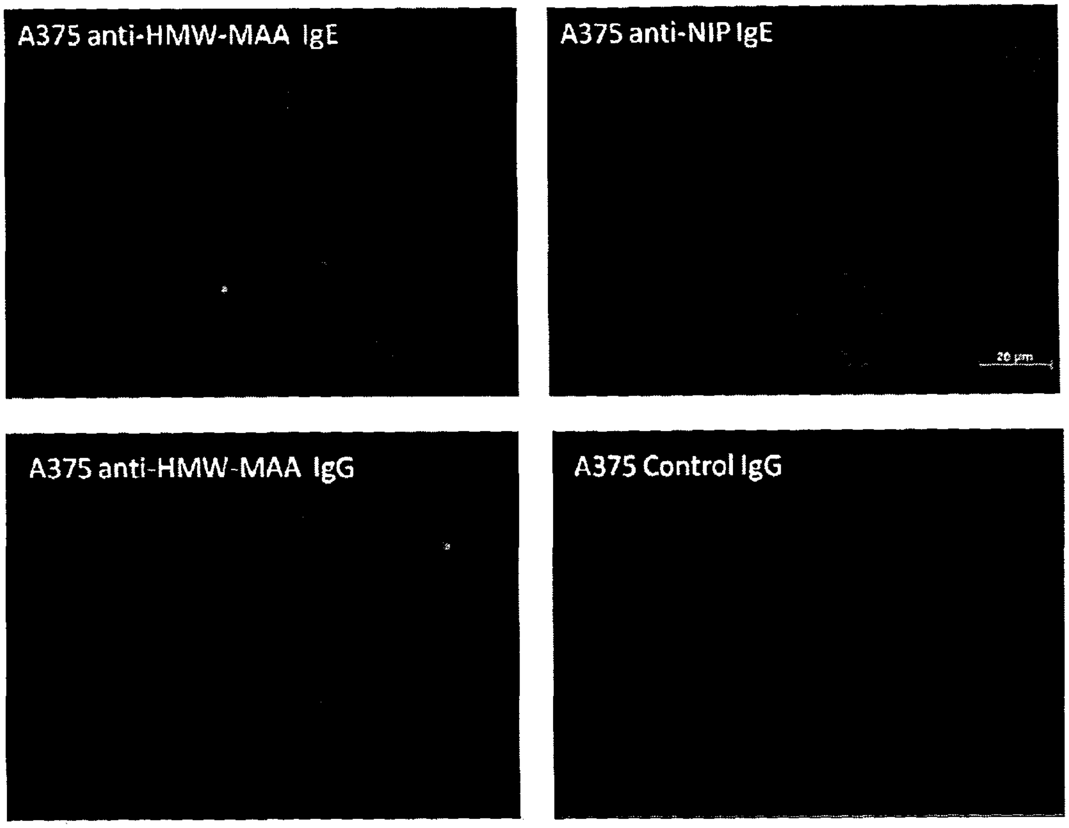
FIG. 4: Binding specificity of HMW-MAA-IgE and $IgG_1$ antibodies to A375 melanoma tumour cells vs. isotype control hapten specific IgE and IgG1 antibodies. Antibodies bound to tumour cells were detected using a goat anti-human IgE-FITC antibody. Images were captured using a 63× oil objective. Scale bar=20 μm.

The interactions of anti-HMW-MAA antibodies with A375 melanoma tumour cells were analysed by flow cytometry and immunofluoresence. Anti-HMW-MAA IgE recognized the HMW-MAA antigen on A375 cells (99.81%), but did not bind human primary melanocytes. The IgE antibody also bound to FcϵR-expressing human primary monocytes and cells of the monocytic cell line U937, which also express both IgE receptors, FcϵRI and FcϵRII at low densities (FIG. 3). The $IgG_1$ antibody bound to the surface of A375 melanoma cells and U937 monocytic cells (FIG. 3C). Specific binding of the chimaeric IgE and $IgG_1$ antibodies to the surface of the A375 tumour cells was confirmed by immunofluorescence microscopy, while a hapten specific isotype control IgE antibody (NIP IgE) and a human $IgG_1$ antibody control did not show binding above background (FIG. 4). Therefore, both chimaeric antibodies of known specificity could be engineered that recognised the expected tumour target and immune effector cells.

In Vitro Functional Assays

Figure 5A:
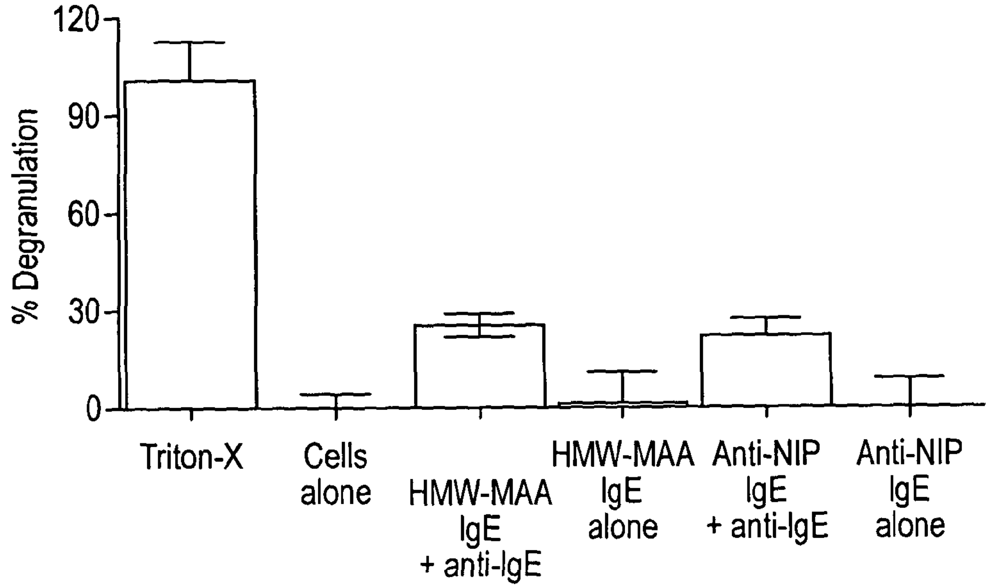
FIG. 5: HMW-MAA IgE stimulates functional degranulation detected (as measured by β-hexosaminidase release) of RBL SX-38 cells after cross-linking with a polyclonal anti-human IgE antibody (A). MTS cell viability assays explored potential direct effects of the anti-HMW-MAA antibodies on melanoma tumour cell proliferation (B). Effects on proliferation were compared with those of trastuzumab ($IgG_1$), which is known to reduce tumour cell proliferation.
Figure 5B:
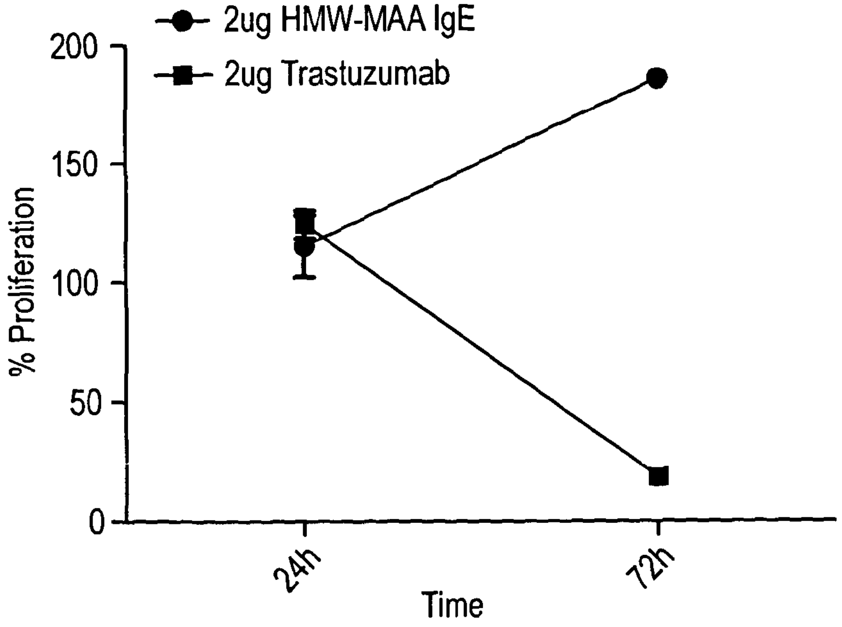
Figure 6:
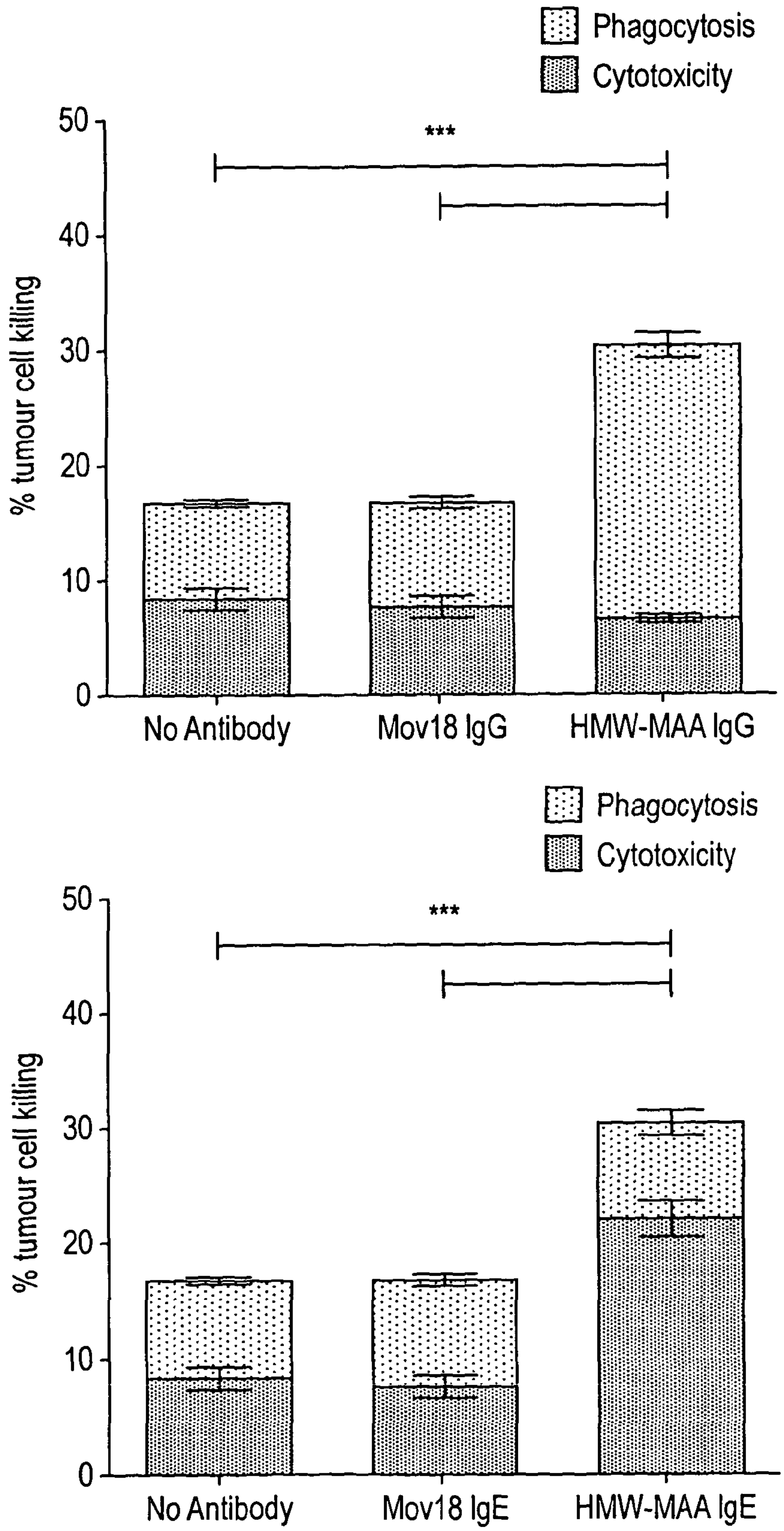
FIG. 6: ADCC/ADCP assays confirmed that anti-HMW-MAA $IgG_1$ (left) and IgE (right) mediated significant levels of ADCP and ADCC respectively of A375 tumour cells by monocytic cells (n=5; *$p<0.05$; $p<0.01$; *$p<0.001$; ns: $p>0.05$).

We employed a number of in vitro assays to examine the capacity of the engineered antibodies to target and kill tumour cells, namely Fc receptor-mediated effector cell activation assays such as functional degranulation and ADCC/ADCP assays, and cell viability assays (MTT) to study the potential to directly kill tumour cells through antigen recognition. We observed that:

1) In a functional degranulation assay measuring % β-hexosaminidase release by RBL SX-38 rat basophilic leukaemia cells expressing human FcϵRI, the HMW-MAA IgE antibody alone did not potentiate β-hexosaminidase release (0.6%). However, the antibody induced significant degranulation of RBL SX-38 cells following stimulation with a polyclonal anti-human IgE antibody (FIG. 5), demonstrating the ability of this antibody to activate immune effector cells through engagement of its high affinity receptor.
2) In vitro cell viability (MIT) assays demonstrated that unlike trastuzumab (IgE and IgG1) antibodies, and as previously reported for the mouse IgG antibody of the same specificity, neither anti-HMW-MAA chimaeric IgE nor the IgG1 counterpart exerted any direct effects on cell proliferation (FIG. 5).
3) Both antibodies were capable of activating immune effector cells to kill cancer cells in vitro with similar effectiveness, but each by different mechanisms: the chimaeric IgG1 activated human monocytes to kill tumour cells by ADCP, while the IgE mediated ADCC of tumour cells (FIG. 6).

Figure 7:
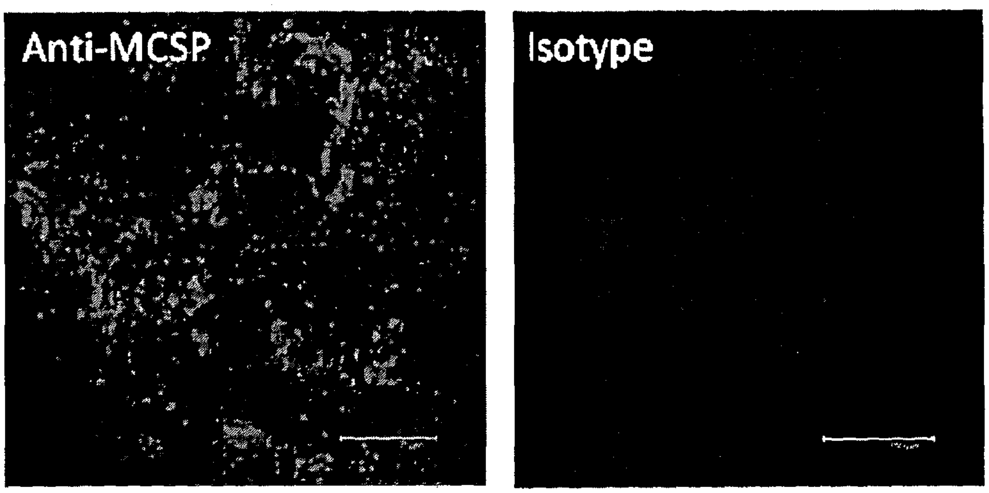
FIG. 7: Immunohistochemical analysis of subcutaneous tumour model of A375 metastatic melanoma cells, labelling for expression of the melanoma marker HMW-MAA (left) and mouse IgG isotype control antibody (right). Images were captured using a 10× objective.

Studies of Efficacy in a Human Melanoma Xenograft Model in NOD/SCID $\gamma^{-/-}$ Mice Engrafted with Human Immune Effector Cells Studies to assess the ability of the melanoma antigen-specific chimaeric antibodies to restrict tumour growth in vivo were conducted in an immunodeficient mouse model of human melanoma grown subcutaneously in NOD/SCID $\gamma^{-/-}$ mice of BALB/c background. Human immune effector cells administered in this model in the form of PBLs, reproducibly demonstrate over 40% spleen engraftment in mice, rendering this in vivo system equivalent to a humanised phenotype. A tumour cell challenge of $5\times10^5$ melanoma cells per mouse resulted in reproducible tumour growth over a period of ~4 weeks, and lesions were positive for the HMW-MAA antigen (FIG. 7).

Figure 8A:
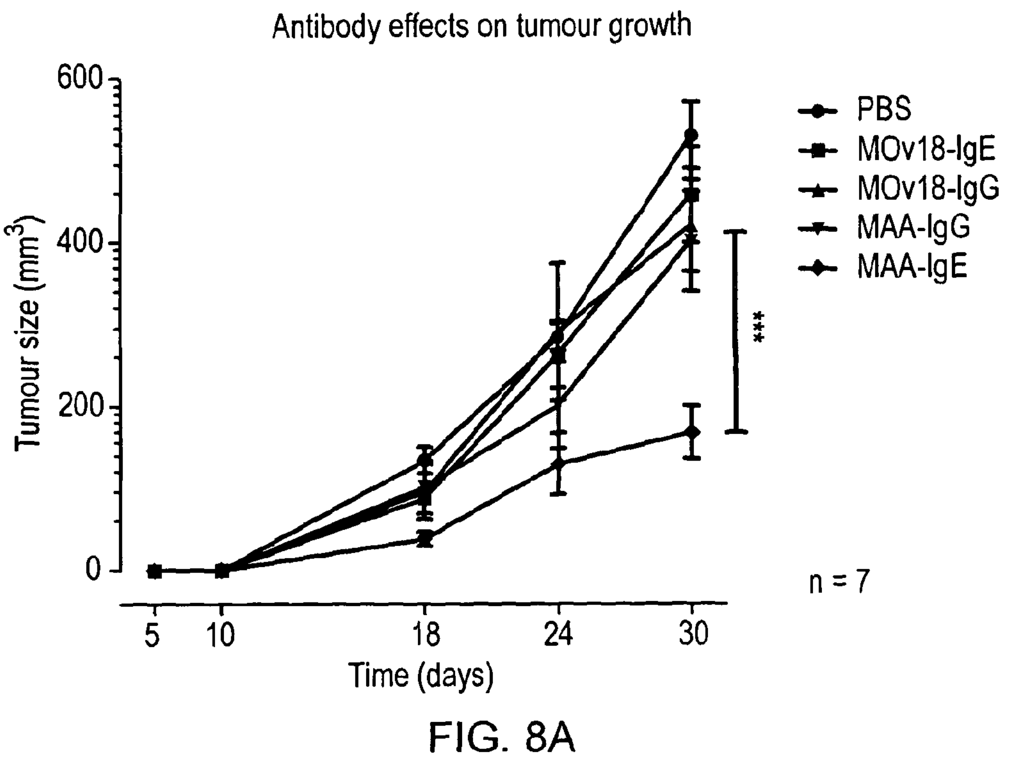
FIG. 8: Testing of engineered antibodies using the subcutaneous melanoma tumour model. A: Monitoring subcutaneous growth ($mm^3$) of melanoma tumours at different time points following tumour challenge (n=7). B: Measurements of tumour mass (mg) at the end of the study (30 days) for each treatment group.
Figure 8B:
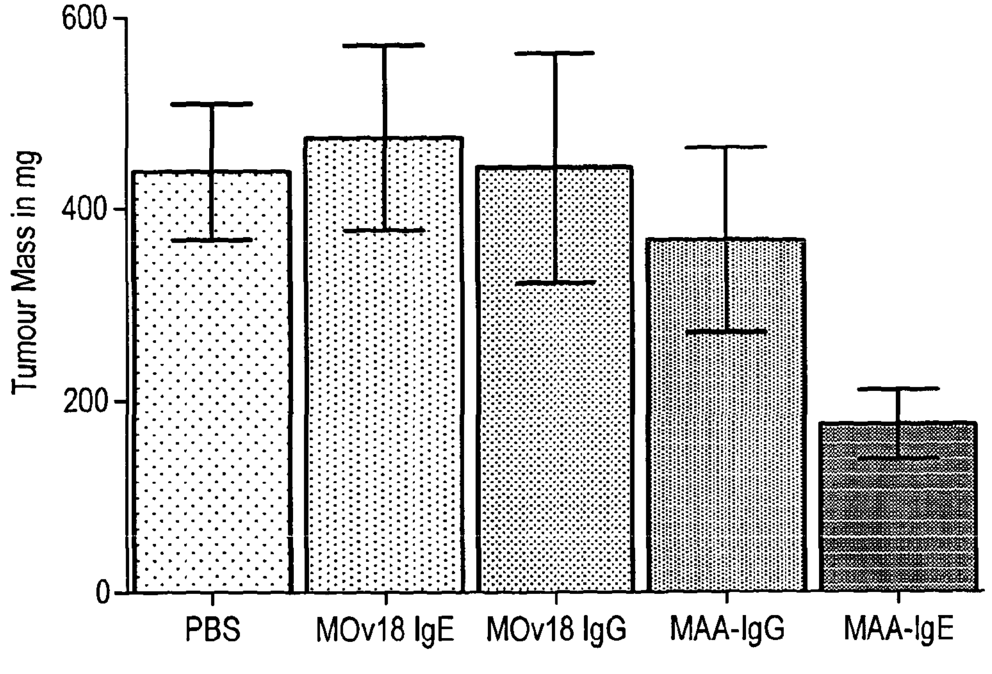
Figure 9:
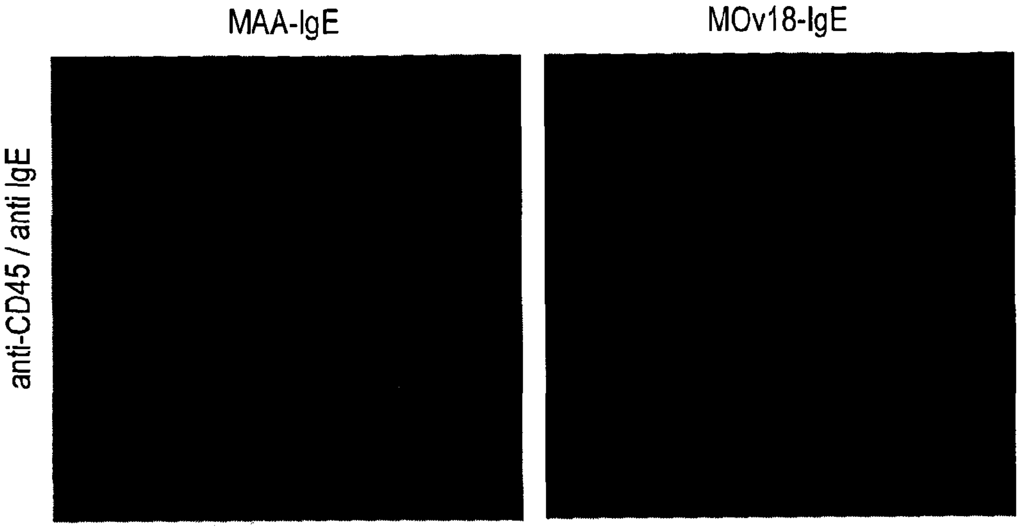
FIG. 9: IgE and human immune cells are recruited in melanoma lesions of mice treated with melanoma antigen specific IgE, but not in lesions from animals treated with a non-specific chimaeric antibody.

Using this subcutaneous in vivo model of melanoma and engraftment of human immune effector cells in these mice, treatment with weekly doses of IgE (10 mg/kg) resulted in severely-restricted melanoma tumour growth over a period of 30 days compared to those treated with the corresponding chimaeric IgG1 at the same doses and to those given non-specific antibody controls (n=7, FIG. 8). Therefore, despite similar levels of tumour cell killing efficiencies in vitro, we observed improved efficacy for anti-HMW-MAA IgE compared to the corresponding IgG1 of the same specificity in vivo.

We also observed profound human immune cell infiltration and the presence of human IgE in tumour lesions from mice that received the anti-HMW-MAA IgE antibody, but neither human immune cell infiltration nor IgE antibody localisation were detected in lesions from animals treated with the non-specific chimaeric IgE antibody MOv18 IgE. We therefore concluded that treatment with melanoma antigen-specific IgE antibody was superior in inducing tumour growth restriction in vivo compared to the corresponding IgG1. Furthermore, systemic treatment with tumour antigen-specific IgE was associated with strong localisation of IgE and infiltration of human immune effector cells in tumour lesions in an antigen-specific manner.

In conclusion, antibodies of different classes and different specificities may have different functional properties against cancer cells, by activating different families of Fc receptors on immune effector cells to destroy tumours. In the context of melanoma, these studies indicate that an IgE antibody against a melanoma antigen has superior efficacy compared to the corresponding IgG1, which may relate to activation and/or recruitment of FcϵR immune effector cells in a mouse xenograft model of melanoma.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

REFERENCES

1 Karim-Kos H E, Kiemeney L A, Louwman M W, Coebergh J W, Vries E D (2011) Progress against cancer in the Netherlands since the late 1980s: an epidemiological evaluation. Int J Cancer 2 Culver M E, Gatesman M L, Mancl E E, Lowe D K (2011) Ipilimumab: a novel treatment for metastatic melanoma. Ann Pharmacother 45: 510-519

3 Kaehler K C, Piel S, Livingstone E, Schilling B, Hauschild A, Schadendorf D (2010) Update on immunologic therapy with anti-CTLA-4 antibodies in melanoma: identification of clinical and biological response patterns, immune-related adverse events, and their management. Semin Oncol 37: 485-498

4 Nataraj an N, Telang S, Miller D, Chesney J (2011) Novel immunotherapeutic agents and small molecule antagonists of signalling kinases for the treatment of metastatic melanoma. Drugs 71: 1233-1250

5 Weiner L M, Surana R, Wang S (2010) Monoclonal antibodies: versatile platforms for cancer immunotherapy. Nat Rev Immunol 10: 317-327

6 Bruggemann M, Williams G T, Bindon C I, Clark M R, Walker M R, Jefferis R, Waldmann H, Neuberger M S (1987) Comparison of the effector functions of human immunoglobulins using a matched set of chimeric antibodies. J Exp Med 166: 1351-1361

7 Alduaij W, Illidge T M (2011) The future of anti-CD20 monoclonal antibodies: are we making progress? Blood 117: 2993-3001

8 Dechant M, Valerius T (2001) IgA antibodies for cancer therapy. Crit Rev Oncol Hematol 39: 69-77

9 Dechant M, Vidarsson G, Stockmeyer B, Repp R, Glennie M J, Gramatzki M, van De Winkel J G, Valerius T (2002) Chimeric IgA antibodies against HLA class II effectively trigger lymphoma cell killing. Blood 100: 4574-4580

10 Dyer M J, Hale G, Hayhoe F G, Waldmann H (1989) Effects of CAMPATH-1 antibodies in vivo in patients with lymphoid malignancies: influence of antibody isotype. Blood 73: 1431-1439

11 Imai M, Landen C, Ohta R, Cheung N K, Tomlinson S (2005) Complement-mediated mechanisms in anti-GD2 monoclonal antibody therapy of murine metastatic cancer. Cancer Res 65: 10562-10568

12 Lohse S, Derer S, Beyer T, Klausz K, Peipp M, Leusen J H, van de Winkel J G, Dechant M, Valerius T (2011) Recombinant dimeric IgA antibodies against the epidermal growth factor receptor mediate effective tumor cell killing. J Immunol 186: 3770-3778

13 Weiner G J (2007) Monoclonal antibody mechanisms of action in cancer. Immunol Res 39: 271-278

14 Ascierto P A, Simeone E, Sznol M, Fu Y X, Melero I (2010) Clinical experiences with anti-CD137 and anti-PD1 therapeutic antibodies. Semin Oncol 37: 508-516

15 Cai J, Han S, Qing R, Liao D, Law B, Boulton M E (2011) In pursuit of new anti-angiogenic therapies for cancer treatment. Front Biosci 16: 803-814

16 Govindan S V, Goldenberg D M (2010) New antibody conjugates in cancer therapy. Scientific World Journal 10: 2070-2089

17 Kubota T, Niwa R, Satoh M, Akinaga S, shitara K, Hanai N (2009) Engineered therapeutic antibodies with improved effector functions. Cancer Sci 100: 1566-1572

18 Hellman L (2007) Regulation of IgE homeostasis, and the identification of potential targets for therapeutic intervention. Biomed Pharmacother 61: 34-49

19 Ravetch J V, Kinet J P (1991) Fc receptors. Annu Rev Immunol 9: 457-492

20 Brigati C, Noonan D M, Albini A, Benelli R (2002) Tumors and inflammatory infiltrates: friends or foes? Clin Exp Metastasis 19: 247-258

21 Kraft S, Kinet J P (2007) New developments in FcepsilonRI regulation, function and inhibition. Nat Rev Immunol 7: 365-378

22 Maenaka K, van der Merwe P A, Stuart D I, Jones E Y, Sondermann P (2001) The human low affinity Fcgamma receptors IIa, IIb, and III bind IgG with fast kinetics and distinct thermodynamic properties. J Biol Chem 276: 44898-44904

23 Gould H J, Sutton B J (2008) IgE in allergy and asthma today. Nat Rev Immunol 8: 205-217

24 Gould H J, Sutton B J, Beavil A J, Beavil R L, McCloskey N, Coker H A, Fear D, Smurthwaite L (2003) The biology of IGE and the basis of allergic disease. Annu Rev Immunol 21: 579-628

25 Kinet J P (1999) The high-affinity IgE receptor (Fc epsilon RI): from physiology to pathology. Annu Rev Immunol 17: 931-972

26 Pages F, Galon J, Dieu-Nosjean M C, Tartour E, Sautes-Fridman C, Fridman W H (2010) Immune infiltration in human tumors: a prognostic factor that should not be ignored. Oncogene 29: 1093-1102

27 Lewis C E, Pollard J W (2006) Distinct role of macrophages in different tumor microenvironments. Cancer Res 66: 605-612

28 Lin E Y, Pollard J W (2004) Role of infiltrated leucocytes in tumour growth and spread. Br J Cancer 90: 2053-2058

29 Matsuda H, Watanabe N, Kiso Y, Hirota S, Ushio H, Kannan Y, Azuma M, Koyama H, Kitamura Y (1990) Necessity of IgE antibodies and mast cells for manifestation of resistance against larval *Haemaphysalis longicornis* ticks in mice. J Immunol 144: 259-262

30 Dombrowicz D, Quatannens B, Papin J P, Capron A, Capron M (2000) Expression of a functional Fc epsilon R1 on rat eosinophils and macrophages. J Immunol 165: 1266-1271

31 Mossalayi M D, Arock M, Mazier D, Vincendeau P, Vouldoukis I (1999) The human immune response during cutaneous leishmaniasis: NO problem. Parasitol Today 15: 342-345

32 Mossalayi M D, Paul-Eugene N, Ouaaz F, Arock M, Kolb J P, Kilchherr E, Debre P, Dugas B (1994) Involvement of Fc epsilon RII/CD23 and L-arginine-dependent pathway in IgE-mediated stimulation of human monocyte functions. Int Immunol 6: 931-934

33 Paul-Eugene N, Mossalayi D, Sarfati M, Yamaoka K, Aubry J P, Bonnefoy J Y, Dugas B, Kolb J P (1995) Evidence for a role of Fc epsilon RII/CD23 in the IL-4-induced nitric oxide production by normal human mononuclear phagocytes. Cell Immunol 163: 314-318

34 Vouldoukis I, Riveros-Moreno V, Dugas B, Ouaaz F, Becherel P, Debre P, Moncada S, Mossalayi M D (1995) The killing of *Leishmania* major by human macrophages is mediated by nitric oxide induced after ligation of the Fc epsilon RII/CD23 surface antigen. Proc Natl Acad Sci USA 92: 7804-7808

35 Campoli M, Ferrone S, Wang X Functional and clinical relevance of chondroitin sulfate proteoglycan 4. Adv Cancer Res 109: 73-121

36 Maciag P C, Seavey M M, Pan Z K, Ferrone S, Paterson Y (2008) Cancer immunotherapy targeting the high molecular weight melanoma-associated antigen protein results in a broad antitumor response and reduction of pericytes in the tumor vasculature. Cancer Res 68: 8066-8075

37 Chang C C, Campoli M, Luo W, Zhao W, Zaenker K S, Ferrone S (2004) Immunotherapy of melanoma targeting human high molecular weight melanoma-associated antigen: potential role of nonimmunological mechanisms. Ann N Y Acad Sci 1028: 340-350

38 Neri D, Natali P G, Petrul H, Soldani P, Nicotra M R, Vola R, Rivella A, Creighton A M, Neri P, Mariani M (1996) Recombinant anti-human melanoma antibodies are versatile molecules. J Invest Dermatol 107: 164-170

39 Ferrone S, Kageshita T (1988) Human high molecular weight-melanoma associated antigen as a target for active specific immunotherapy—a phase I clinical trial with murine antiidiotypic monoclonal antibodies. J Dermatol 15: 457-465

40 Hafner C, Breiteneder H, Ferrone S, Thallinger C, Wagner S, Schmidt W M, Jasinska J, Kundi M, Wolff K, Zielinski C C et al (2005) Suppression of human melanoma tumor growth in SCID mice by a human high molecular weight-melanoma associated antigen (HMW-MAA) specific monoclonal antibody. Int J Cancer 114: 426-432

41 Imai K, Nakanishi T, Noguchi T, Yachi A, Ferrone S (1983) Selective in vitro toxicity of purothionin conjugated to the monoclonal antibody 225.28S to a human high-molecular-weight melanoma-associated antigen. Cancer Immunol Immunother 15: 206-209

42 Matsui M, Nakanishi T, Noguchi T, Imai K, Yachi A, Ferrone S (1985) Suppression of human melanoma growth in nude mice injected with anti high-molecular-weight melanoma-associated antigen monoclonal antibody 225.28S conjugated to purothionin. Jpn J Cancer Res 76: 119-123

43 Gould H J, Mackay G A, Karagiannis S N, O'Toole C M, Marsh P J, Daniel B E, Coney L R, Zurawski V R, Jr., Joseph M, Capron M et al (1999) Comparison of IgE and IgG antibody-dependent cytotoxicity in vitro and in a SCID mouse xenograft model of ovarian carcinoma. Eur J Immunol 29: 3527-3537

44 Karagiannis P, Singer J, Hunt J, Gan S K, Rudman S M, Mechtcheriakova D, Knittelfelder R, Daniels T R, Hobson P S, Beavil A J et al (2009) Characterisation of an engineered trastuzumab IgE antibody and effector cell mechanisms targeting HER2/neu-positive tumour cells. Cancer Immunol Immunother 58: 915-930

45 Karagiannis S N, Bracher M G, Beavil R L, Beavil A J, Hunt J, McCloskey N, Thompson R G, East N, Burke F, Sutton B J et al (2008) Role of IgE receptors in IgE antibody-dependent cytotoxicity and phagocytosis of ovarian tumor cells by human monocytic cells. Cancer Immunol Immunother 57: 247-263

46 Karagiannis S N, Bracher M G, Hunt J, McCloskey N, Beavil R L, Beavil A J, Fear D J, Thompson R G, East N, Burke F et al (2007) IgE-antibody-dependent immunotherapy of solid tumors: cytotoxic and phagocytic mechanisms of eradication of ovarian cancer cells. J Immunol 179: 2832-2843

47 Karagiannis S N, Wang Q, East N, Burke F, Riffard S, Bracher M G, Thompson R G, Durham S R, Schwartz L B, Balkwill F R et al (2003) Activity of human monocytes in IgE antibody-dependent surveillance and killing of ovarian tumor cells. Eur J Immunol 33: 1030-1040

The invention claimed is:

1. An IgE antibody, wherein the antibody is capable of:

(a) binding specifically to high molecular weight melanoma associated antigen (HMW-MAA); and (b) binding to an Fcϵ receptor, wherein the antibody comprises heavy chain CDR sequences of SEQ ID NO: 18, SEQ ID NO: 19and SEQ ID NO: 20 and light chain CDR sequences of SEQ ID NO: 21, SEQ ID NO: 22 and SEQ ID NO: 23.

2. The antibody of claim 1, wherein the antibody comprises one or more constant regions capable of binding to an Fcϵ receptor.

3. The antibody of claim 1 wherein the antibody has framework regions or constant domains that are derived from a mammalian species other than a mouse.

4. The antibody of claim 3, wherein the framework regions or constant domains are derived from a human.

5. The antibody of claim 1, comprising one or more heavy chain constant domains selected from the group consisting of Cϵ1, Cϵ2, Cϵ3, and Cϵ4.

6. The antibody of claim 1, wherein the antibody or functional fragment thereof comprises an ϵ heavy chain.

7. The antibody of claim 1, wherein the antibody or functional fragment thereof comprises one or more variable domains derived from an IgG.

8. The antibody of claim 1, wherein the antibody is conjugated to a detectable label, or a therapeutic agent, a cytotoxin, an encapsulating agent or a radioactive moiety.

9. The antibody of claim 1, wherein the antibody comprises a VH domain comprising SEQ ID NO:4 or a VL domain comprising SEQ ID NO:6.

10. The antibody of claim 1, wherein the antibody comprises a heavy chain comprising the amino acid sequence as defined in SEQ ID NO:7, or a light chain comprising the amino acid sequence as defined in SEQ ID NO:8.

11. A pharmaceutical composition comprising the antibody of claim 1, and a pharmaceutically acceptable carrier.

12. A method of treating malignant melanoma in a subject, comprising administering to the subject a therapeutically effective amount of the pharmaceutical composition of claim 11, wherein the malignant melanoma expresses HMW-MAA.

* * * * *

SEQUENCE LISTING

```
<160> NUMBER OF SEQ ID NOS: 28

<210> SEQ ID NO 1
<211> LENGTH: 2322
<212> TYPE: PRT
```

<213> ORGANISM: Homo sapiens

<400> SEQUENCE: 1

```
Met Gln Ser Gly Pro Arg Pro Pro Leu Pro Ala Pro Gly Leu Ala Leu
1               5                   10                  15

Ala Leu Thr Leu Thr Met Leu Ala Arg Leu Ala Ser Ala Ala Ser Phe
            20                  25                  30

Phe Gly Glu Asn His Leu Glu Val Pro Val Ala Thr Ala Leu Thr Asp
        35                  40                  45

Ile Asp Leu Gln Leu Gln Phe Ser Thr Ser Gln Pro Glu Ala Leu Leu
    50                  55                  60

Leu Leu Ala Ala Gly Pro Ala Asp His Leu Leu Leu Gln Leu Tyr Ser
65                  70                  75                  80

Gly Arg Leu Gln Val Arg Leu Val Leu Gly Gln Glu Glu Leu Arg Leu
                85                  90                  95

Gln Thr Pro Ala Glu Thr Leu Leu Ser Asp Ser Ile Pro His Thr Val
            100                 105                 110

Val Leu Thr Val Val Glu Gly Trp Ala Thr Leu Ser Val Asp Gly Phe
        115                 120                 125

Leu Asn Ala Ser Ser Ala Val Pro Gly Ala Pro Leu Glu Val Pro Tyr
    130                 135                 140

Gly Leu Phe Val Gly Gly Thr Gly Thr Leu Gly Leu Pro Tyr Leu Arg
145                 150                 155                 160

Gly Thr Ser Arg Pro Leu Arg Gly Cys Leu His Ala Ala Thr Leu Asn
                165                 170                 175

Gly Arg Ser Leu Leu Arg Pro Leu Thr Pro Asp Val His Glu Gly Cys
            180                 185                 190

Ala Glu Glu Phe Ser Ala Ser Asp Asp Val Ala Leu Gly Phe Ser Gly
        195                 200                 205

Pro His Ser Leu Ala Ala Phe Pro Ala Trp Gly Thr Gln Asp Glu Gly
    210                 215                 220

Thr Leu Glu Phe Thr Leu Thr Thr Gln Ser Arg Gln Ala Pro Leu Ala
225                 230                 235                 240

Phe Gln Ala Gly Gly Arg Arg Gly Asp Phe Ile Tyr Val Asp Ile Phe
                245                 250                 255

Glu Gly His Leu Arg Ala Val Val Glu Lys Gly Gln Gly Thr Val Leu
            260                 265                 270

Leu His Asn Ser Val Pro Val Ala Asp Gly Gln Pro His Glu Val Ser
        275                 280                 285

Val His Ile Asn Ala His Arg Leu Glu Ile Ser Val Asp Gln Tyr Pro
    290                 295                 300

Thr His Thr Ser Asn Arg Gly Val Leu Ser Tyr Leu Glu Pro Arg Gly
305                 310                 315                 320

Ser Leu Leu Leu Gly Gly Leu Asp Ala Glu Ala Ser Arg His Leu Gln
                325                 330                 335

Glu His Arg Leu Gly Leu Thr Pro Glu Ala Thr Asn Ala Ser Leu Leu
            340                 345                 350

Gly Cys Met Glu Asp Leu Ser Val Asn Gly Gln Arg Arg Gly Leu Arg
        355                 360                 365

Glu Ala Leu Leu Thr Arg Asn Met Ala Ala Gly Cys Arg Leu Glu Glu
    370                 375                 380

Glu Glu Tyr Glu Asp Asp Ala Tyr Gly His Tyr Glu Ala Phe Ser Thr
385                 390                 395                 400
```

-continued

```
Leu Ala Pro Glu Ala Trp Pro Ala Met Glu Leu Pro Glu Pro Cys Val
                405                 410                 415

Pro Glu Pro Gly Leu Pro Pro Val Phe Ala Asn Phe Thr Gln Leu Leu
            420                 425                 430

Thr Ile Ser Pro Leu Val Val Ala Glu Gly Gly Thr Ala Trp Leu Glu
        435                 440                 445

Trp Arg His Val Gln Pro Thr Leu Asp Leu Met Glu Ala Glu Leu Arg
    450                 455                 460

Lys Ser Gln Val Leu Phe Ser Val Thr Arg Gly Ala Arg His Gly Glu
465                 470                 475                 480

Leu Glu Leu Asp Ile Pro Gly Ala Gln Ala Arg Lys Met Phe Thr Leu
                485                 490                 495

Leu Asp Val Val Asn Arg Lys Ala Arg Phe Ile His Asp Gly Ser Glu
            500                 505                 510

Asp Thr Ser Asp Gln Leu Val Leu Glu Val Ser Val Thr Ala Arg Val
        515                 520                 525

Pro Met Pro Ser Cys Leu Arg Arg Gly Gln Thr Tyr Leu Leu Pro Ile
    530                 535                 540

Gln Val Asn Pro Val Asn Asp Pro Pro His Ile Ile Phe Pro His Gly
545                 550                 555                 560

Ser Leu Met Val Ile Leu Glu His Thr Gln Lys Pro Leu Gly Pro Glu
                565                 570                 575

Val Phe Gln Ala Tyr Asp Pro Asp Ser Ala Cys Glu Gly Leu Thr Phe
            580                 585                 590

Gln Val Leu Gly Thr Ser Ser Gly Leu Pro Val Glu Arg Arg Asp Gln
        595                 600                 605

Pro Gly Glu Pro Ala Thr Glu Phe Ser Cys Arg Glu Leu Glu Ala Gly
    610                 615                 620

Ser Leu Val Tyr Val His Arg Gly Gly Pro Ala Gln Asp Leu Thr Phe
625                 630                 635                 640

Arg Val Ser Asp Gly Leu Gln Ala Ser Pro Pro Ala Thr Leu Lys Val
                645                 650                 655

Val Ala Ile Arg Pro Ala Ile Gln Ile His Arg Ser Thr Gly Leu Arg
            660                 665                 670

Leu Ala Gln Gly Ser Ala Met Pro Ile Leu Pro Ala Asn Leu Ser Val
        675                 680                 685

Glu Thr Asn Ala Val Gly Gln Asp Val Ser Val Leu Phe Arg Val Thr
    690                 695                 700

Gly Ala Leu Gln Phe Gly Glu Leu Gln Lys Gln Gly Ala Gly Gly Val
705                 710                 715                 720

Glu Gly Ala Glu Trp Trp Ala Thr Gln Ala Phe His Gln Arg Asp Val
                725                 730                 735

Glu Gln Gly Arg Val Arg Tyr Leu Ser Thr Asp Pro Gln His His Ala
            740                 745                 750

Tyr Asp Thr Val Glu Asn Leu Ala Leu Glu Val Gln Val Gly Gln Glu
        755                 760                 765

Ile Leu Ser Asn Leu Ser Phe Pro Val Thr Ile Gln Arg Ala Thr Val
    770                 775                 780

Trp Met Leu Arg Leu Glu Pro Leu His Thr Gln Asn Thr Gln Gln Glu
785                 790                 795                 800

Thr Leu Thr Thr Ala His Leu Glu Ala Thr Leu Glu Glu Ala Gly Pro
                805                 810                 815

Ser Pro Pro Thr Phe His Tyr Glu Val Val Gln Ala Pro Arg Lys Gly
```

-continued

```
            820                 825                 830

Asn Leu Gln Leu Gln Gly Thr Arg Leu Ser Asp Gly Gln Gly Phe Thr
        835                 840                 845

Gln Asp Asp Ile Gln Ala Gly Arg Val Thr Tyr Gly Ala Thr Ala Arg
    850                 855                 860

Ala Ser Glu Ala Val Glu Asp Thr Phe Arg Phe Arg Val Thr Ala Pro
865                 870                 875                 880

Pro Tyr Phe Ser Pro Leu Tyr Thr Phe Pro Ile His Ile Gly Gly Asp
                885                 890                 895

Pro Asp Ala Pro Val Leu Thr Asn Val Leu Leu Val Val Pro Glu Gly
            900                 905                 910

Gly Glu Gly Val Leu Ser Ala Asp His Leu Phe Val Lys Ser Leu Asn
        915                 920                 925

Ser Ala Ser Tyr Leu Tyr Glu Val Met Glu Arg Pro Arg His Gly Arg
    930                 935                 940

Leu Ala Trp Arg Gly Thr Gln Asp Lys Thr Thr Met Val Thr Ser Phe
945                 950                 955                 960

Thr Asn Glu Asp Leu Leu Arg Gly Arg Leu Val Tyr Gln His Asp Asp
                965                 970                 975

Ser Glu Thr Thr Glu Asp Asp Ile Pro Phe Val Ala Thr Arg Gln Gly
            980                 985                 990

Glu Ser Ser Gly Asp Met Ala Trp  Glu Glu Val Arg Gly  Val Phe Arg
        995                 1000                 1005

Val Ala  Ile Gln Pro Val Asn  Asp His Ala Pro Val  Gln Thr Ile
    1010                 1015                 1020

Ser Arg  Ile Phe His Val Ala  Arg Gly Gly Arg Arg  Leu Leu Thr
    1025                 1030                 1035

Thr Asp  Asp Val Ala Phe Ser  Asp Ala Asp Ser Gly  Phe Ala Asp
    1040                 1045                 1050

Ala Gln  Leu Val Leu Thr Arg  Lys Asp Leu Leu Phe  Gly Ser Ile
    1055                 1060                 1065

Val Ala  Val Asp Glu Pro Thr  Arg Pro Ile Tyr Arg  Phe Thr Gln
    1070                 1075                 1080

Glu Asp  Leu Arg Lys Arg Arg  Val Leu Phe Val His  Ser Gly Ala
    1085                 1090                 1095

Asp Arg  Gly Trp Ile Gln Leu  Gln Val Ser Asp Gly  Gln His Gln
    1100                 1105                 1110

Ala Thr  Ala Leu Leu Glu Val  Gln Ala Ser Glu Pro  Tyr Leu Arg
    1115                 1120                 1125

Val Ala  Asn Gly Ser Ser Leu  Val Val Pro Gln Gly  Gly Gln Gly
    1130                 1135                 1140

Thr Ile  Asp Thr Ala Val Leu  His Leu Asp Thr Asn  Leu Asp Ile
    1145                 1150                 1155

Arg Ser  Gly Asp Glu Val His  Tyr His Val Thr Ala  Gly Pro Arg
    1160                 1165                 1170

Trp Gly  Gln Leu Val Arg Ala  Gly Gln Pro Ala Thr  Ala Phe Ser
    1175                 1180                 1185

Gln Gln  Asp Leu Leu Asp Gly  Ala Val Leu Tyr Ser  His Asn Gly
    1190                 1195                 1200

Ser Leu  Ser Pro Arg Asp Thr  Met Ala Phe Ser Val  Glu Ala Gly
    1205                 1210                 1215

Pro Val  His Thr Asp Ala Thr  Leu Gln Val Thr Ile  Ala Leu Glu
    1220                 1225                 1230
```

-continued

```
Gly Pro  Leu Ala Pro Leu Lys  Leu Val Arg His Lys  Lys Ile Tyr
    1235                 1240                 1245

Val Phe  Gln Gly Glu Ala Ala  Glu Ile Arg Arg Asp  Gln Leu Glu
    1250                 1255                 1260

Ala Ala  Gln Glu Ala Val Pro  Pro Ala Asp Ile Val  Phe Ser Val
    1265                 1270                 1275

Lys Ser  Pro Pro Ser Ala Gly  Tyr Leu Val Met Val  Ser Arg Gly
    1280                 1285                 1290

Ala Leu  Ala Asp Glu Pro Pro  Ser Leu Asp Pro Val  Gln Ser Phe
    1295                 1300                 1305

Ser Gln  Glu Ala Val Asp Thr  Gly Arg Val Leu Tyr  Leu His Ser
    1310                 1315                 1320

Arg Pro  Glu Ala Trp Ser Asp  Ala Phe Ser Leu Asp  Val Ala Ser
    1325                 1330                 1335

Gly Leu  Gly Ala Pro Leu Glu  Gly Val Leu Val Glu  Leu Glu Val
    1340                 1345                 1350

Leu Pro  Ala Ala Ile Pro Leu  Glu Ala Gln Asn Phe  Ser Val Pro
    1355                 1360                 1365

Glu Gly  Gly Ser Leu Thr Leu  Ala Pro Pro Leu Leu  Arg Val Ser
    1370                 1375                 1380

Gly Pro  Tyr Phe Pro Thr Leu  Leu Gly Leu Ser Leu  Gln Val Leu
    1385                 1390                 1395

Glu Pro  Pro Gln His Gly Ala  Leu Gln Lys Glu Asp  Gly Pro Gln
    1400                 1405                 1410

Ala Arg  Thr Leu Ser Ala Phe  Ser Trp Arg Met Val  Glu Glu Gln
    1415                 1420                 1425

Leu Ile  Arg Tyr Val His Asp  Gly Ser Glu Thr Leu  Thr Asp Ser
    1430                 1435                 1440

Phe Val  Leu Met Ala Asn Ala  Ser Glu Met Asp Arg  Gln Ser His
    1445                 1450                 1455

Pro Val  Ala Phe Thr Val Thr  Val Leu Pro Val Asn  Asp Gln Pro
    1460                 1465                 1470

Pro Ile  Leu Thr Thr Asn Thr  Gly Leu Gln Met Trp  Glu Gly Ala
    1475                 1480                 1485

Thr Ala  Pro Ile Pro Ala Glu  Ala Leu Arg Ser Thr  Asp Gly Asp
    1490                 1495                 1500

Ser Gly  Ser Glu Asp Leu Val  Tyr Thr Ile Glu Gln  Pro Ser Asn
    1505                 1510                 1515

Gly Arg  Val Val Leu Arg Gly  Ala Pro Gly Thr Glu  Val Arg Ser
    1520                 1525                 1530

Phe Thr  Gln Ala Gln Leu Asp  Gly Gly Leu Val Leu  Phe Ser His
    1535                 1540                 1545

Arg Gly  Thr Leu Asp Gly Gly  Phe Arg Phe Arg Leu  Ser Asp Gly
    1550                 1555                 1560

Glu His  Thr Ser Pro Gly His  Phe Phe Arg Val Thr  Ala Gln Lys
    1565                 1570                 1575

Gln Val  Leu Leu Ser Leu Lys  Gly Ser Gln Thr Leu  Thr Val Cys
    1580                 1585                 1590

Pro Gly  Ser Val Gln Pro Leu  Ser Ser Gln Thr Leu  Arg Ala Ser
    1595                 1600                 1605

Ser Ser  Ala Gly Thr Asp Pro  Gln Leu Leu Leu Tyr  Arg Val Val
    1610                 1615                 1620
```

-continued

```
Arg Gly  Pro Gln Leu Gly Arg  Leu Phe His Ala Gln  Gln Asp Ser
    1625                 1630                 1635

Thr Gly  Glu Ala Leu Val Asn  Phe Thr Gln Ala Glu  Val Tyr Ala
    1640                 1645                 1650

Gly Asn  Ile Leu Tyr Glu His  Glu Met Pro Pro Glu  Pro Phe Trp
    1655                 1660                 1665

Glu Ala  His Asp Thr Leu Glu  Leu Gln Leu Ser Ser  Pro Pro Ala
    1670                 1675                 1680

Arg Asp  Val Ala Ala Thr Leu  Ala Val Ala Val Ser  Phe Glu Ala
    1685                 1690                 1695

Ala Cys  Pro Gln Arg Pro Ser  His Leu Trp Lys Asn  Lys Gly Leu
    1700                 1705                 1710

Trp Val  Pro Glu Gly Gln Arg  Ala Arg Ile Thr Val  Ala Ala Leu
    1715                 1720                 1725

Asp Ala  Ser Asn Leu Leu Ala  Ser Val Pro Ser Pro  Gln Arg Ser
    1730                 1735                 1740

Glu His  Asp Val Leu Phe Gln  Val Thr Gln Phe Pro  Ser Arg Gly
    1745                 1750                 1755

Gln Leu  Leu Val Ser Glu Glu  Pro Leu His Ala Gly  Gln Pro His
    1760                 1765                 1770

Phe Leu  Gln Ser Gln Leu Ala  Ala Gly Gln Leu Val  Tyr Ala His
    1775                 1780                 1785

Gly Gly  Gly Gly Thr Gln Gln  Asp Gly Phe His Phe  Arg Ala His
    1790                 1795                 1800

Leu Gln  Gly Pro Ala Gly Ala  Ser Val Ala Gly Pro  Gln Thr Ser
    1805                 1810                 1815

Glu Ala  Phe Ala Ile Thr Val  Arg Asp Val Asn Glu  Arg Pro Pro
    1820                 1825                 1830

Gln Pro  Gln Ala Ser Val Pro  Leu Arg Leu Thr Arg  Gly Ser Arg
    1835                 1840                 1845

Ala Pro  Ile Ser Arg Ala Gln  Leu Ser Val Val Asp  Pro Asp Ser
    1850                 1855                 1860

Ala Pro  Gly Glu Ile Glu Tyr  Glu Val Gln Arg Ala  Pro His Asn
    1865                 1870                 1875

Gly Phe  Leu Ser Leu Val Gly  Gly Gly Leu Gly Pro  Val Thr Arg
    1880                 1885                 1890

Phe Thr  Gln Ala Asp Val Asp  Ser Gly Arg Leu Ala  Phe Val Ala
    1895                 1900                 1905

Asn Gly  Ser Ser Val Ala Gly  Ile Phe Gln Leu Ser  Met Ser Asp
    1910                 1915                 1920

Gly Ala  Ser Pro Pro Leu Pro  Met Ser Leu Ala Val  Asp Ile Leu
    1925                 1930                 1935

Pro Ser  Ala Ile Glu Val Gln  Leu Arg Ala Pro Leu  Glu Val Pro
    1940                 1945                 1950

Gln Ala  Leu Gly Arg Ser Ser  Leu Ser Gln Gln Gln  Leu Arg Val
    1955                 1960                 1965

Val Ser  Asp Arg Glu Glu Pro  Glu Ala Ala Tyr Arg  Leu Ile Gln
    1970                 1975                 1980

Gly Pro  Gln Tyr Gly His Leu  Leu Val Gly Gly Arg  Pro Thr Ser
    1985                 1990                 1995

Ala Phe  Ser Gln Phe Gln Ile  Asp Gln Gly Glu Val  Val Phe Ala
    2000                 2005                 2010

Phe Thr  Asn Phe Ser Ser Ser  His Asp His Phe Arg  Val Leu Ala
```

-continued

```
    2015                2020                2025

Leu Ala  Arg Gly Val Asn Ala  Ser Ala Val Val Asn  Val Thr Val
    2030                2035                2040

Arg Ala  Leu Leu His Val Trp  Ala Gly Gly Pro Trp  Pro Gln Gly
    2045                2050                2055

Ala Thr  Leu Arg Leu Asp Pro  Thr Val Leu Asp Ala  Gly Glu Leu
    2060                2065                2070

Ala Asn  Arg Thr Gly Ser Val  Pro Arg Phe Arg Leu  Leu Glu Gly
    2075                2080                2085

Pro Arg  His Gly Arg Val Val  Arg Val Pro Arg Ala  Arg Thr Glu
    2090                2095                2100

Pro Gly  Gly Ser Gln Leu Val  Glu Gln Phe Thr Gln  Gln Asp Leu
    2105                2110                2115

Glu Asp  Gly Arg Leu Gly Leu  Glu Val Gly Arg Pro  Glu Gly Arg
    2120                2125                2130

Ala Pro  Gly Pro Ala Gly Asp  Ser Leu Thr Leu Glu  Leu Trp Ala
    2135                2140                2145

Gln Gly  Val Pro Pro Ala Val  Ala Ser Leu Asp Phe  Ala Thr Glu
    2150                2155                2160

Pro Tyr  Asn Ala Ala Arg Pro  Tyr Ser Val Ala Leu  Leu Ser Val
    2165                2170                2175

Pro Glu  Ala Ala Arg Thr Glu  Ala Gly Lys Pro Glu  Ser Ser Thr
    2180                2185                2190

Pro Thr  Gly Glu Pro Gly Pro  Met Ala Ser Ser Pro  Glu Pro Ala
    2195                2200                2205

Val Ala  Lys Gly Gly Phe Leu  Ser Phe Leu Glu Ala  Asn Met Phe
    2210                2215                2220

Ser Val  Ile Ile Pro Met Cys  Leu Val Leu Leu Leu  Leu Ala Leu
    2225                2230                2235

Ile Leu  Pro Leu Leu Phe Tyr  Leu Arg Lys Arg Asn  Lys Thr Gly
    2240                2245                2250

Lys His  Asp Val Gln Val Leu  Thr Ala Lys Pro Arg  Asn Gly Leu
    2255                2260                2265

Ala Gly  Asp Thr Glu Thr Phe  Arg Lys Val Glu Pro  Gly Gln Ala
    2270                2275                2280

Ile Pro  Leu Thr Ala Val Pro  Gly Gln Gly Pro Pro  Pro Gly Gly
    2285                2290                2295

Gln Pro  Asp Pro Glu Leu Leu  Gln Phe Cys Arg Thr  Pro Asn Pro
    2300                2305                2310

Ala Leu  Lys Asn Gly Gln Tyr  Trp Val
    2315                2320


<210> SEQ ID NO 2
<211> LENGTH: 6969
<212> TYPE: DNA
<213> ORGANISM: Homo sapiens

<400> SEQUENCE: 2

atgcagtccg ggccgcggcc cccacttcca gcccccggcc tggccttggc tttgaccctg     60

actatgttgg ccagacttgc atccgcggct tccttcttcg gtgagaacca cctggaggtg    120

cctgtggcca cggctctgac cgacatagac ctgcagctgc agttctccac gtcccagccc    180

gaagccctcc ttctcctggc agcaggccca gctgaccacc tcctgctgca gctctactct    240

ggacgcctgc aggtcagact tgttctgggc caggaggagc tgaggctgca gactccagca    300
```

```
gagacgctgc tgagtgactc catcccccac actgtggtgc tgactgtcgt agagggctgg    360
gccacgttgt cagtcgatgg gtttctgaac gcctcctcag cagtcccagg agccccccta    420
gaggtcccct atgggctctt tgttgggggc actgggaccc ttggcctgcc ctacctgagg    480
ggaaccagcc gacccctgag ggttgcctc catgcagcca ccctcaatgg ccgcagcctc    540
ctccggcctc tgacccccga tgtgcatgag ggctgtgctg aagagttttc tgccagtgat    600
gatgtggccc tgggcttctc tgggccccac tctctggctg ccttccctgc ctggggcact    660
caggacgaag gaaccctaga gtttacactc accacacaga gccggcaggc acccttggcc    720
ttccaggcag gggccggcg tggggacttc atctatgtgg acatatttga gggccacctg    780
cgggccgtgg tggagaaggg ccagggtacc gtattgctcc acaacagtgt gcctgtggcc    840
gatgggcagc cccatgaggt cagtgtccac atcaatgctc accggctgga aatctccgtg    900
gaccagtacc ctacgcatac ttcgaaccga ggagtcctca gctacctgga gccacggggc    960
agtctccttc tcggggggct ggatgcagag gcctctcgtc acctccagga acaccgcctg   1020
ggcctgacac cagaggccac caatgcctcc ctgctgggct gcatggaaga cctcagtgtc   1080
aatggccaga ggcgggggct gcgggaagct ttgctgacgc gcaacatggc agccggctgc   1140
aggctggagg aggaggagta tgaggacgat gcctatggac attatgaagc tttctccacc   1200
ctggcccctg aggcttggcc agccatggag ctgcctgagc catgcgtgcc tgagccaggg   1260
ctgcctcctg tctttgccaa tttcacccag ctgctgacta tcagcccact ggtggtggcc   1320
gagggggca cagcctggct tgagtggagg catgtgcagc ccacgctgga cctgatggag   1380
gctgagctgc gcaaatccca ggtgctgttc agcgtgaccc gaggggcacg ccatggcgag   1440
ctcgagctgg acatcccggg agcccaggca cgaaaaatgt tcaccctcct ggacgtggtg   1500
aaccgcaagg cccgcttcat ccacgatggc tctgaggaca cctccgacca gctggtgctg   1560
gaggtgtcgg tgacggctcg ggtgcccatg ccctcatgcc ttcggagggg ccaaacatac   1620
ctcctgccca tccaggtcaa ccctgtcaat gacccacccc acatcatctt cccacatggc   1680
agcctcatgg tgatcctgga acacacgcag aagccgctgg ggcctgaggt tttccaggcc   1740
tatgacccgg actctgcctg tgagggcctc accttccagg tccttggcac ctcctctggc   1800
ctccccgtgg agcgccgaga ccagcctggg gagccggcga ccgagttctc ctgccgggag   1860
ttggaggccg gcagcctagt ctatgtccac cgcggtggtc ctgcacagga cttgacgttc   1920
cgggtcagcg atggactgca ggccagcccc ccggccacgc tgaaggtggt ggccatccgg   1980
ccggccatac agatccaccg cagcacaggg ttgcgactgg cccaaggctc tgccatgccc   2040
atcttgcccg ccaacctgtc ggtggagacc aatgccgtgg ggcaggatgt gagcgtgctg   2100
ttccgcgtca ctggggccct gcagtttggg gagctgcaga agcagggggc aggtggggtg   2160
gagggtgctg agtggtgggc cacacaggcg ttccaccagc gggatgtgga gcagggccgc   2220
gtgaggtacc tgagcactga cccacagcac cacgcttacg acaccgtgga gaacctggcc   2280
ctggaggtgc aggtgggcca ggagatcctg agcaatctgt ccttcccagt gaccatccag   2340
agagccactg tgtggatgct gcggctggag ccactgcaca ctcagaacac ccagcaggag   2400
accctcacca cagcccacct ggaggccacc ctggaggagg caggcccaag ccccccaacc   2460
ttccattatg aggtggttca ggctcccagg aaaggcaacc ttcaactaca gggcacaagg   2520
ctgtcagatg gccagggctt cacccaggat gacatacagg ctggccgggt gacctatggg   2580
gccacagcac gtgcctcaga ggcagtcgag gacaccttcc gtttccgtgt cacagctcca   2640
```

-continued

```
ccatatttct ccccactcta taccttcccc atccacattg gtggtgaccc agatgcgcct   2700
gtcctcacca atgtcctcct cgtggtgcct gagggtggtg agggtgtcct ctctgctgac   2760
cacctctttg tcaagagtct caacagtgcc agctacctct atgaggtcat ggagcggccc   2820
cgccatggga ggttggcttg gcgtgggaca caggacaaga ccactatggt gacatccttc   2880
accaatgaag acctgttgcg tggccggctg gtctaccagc atgatgactc cgagaccaca   2940
gaagatgata tcccatttgt tgctacccgc cagggcgaga gcagtggtga catggcctgg   3000
gaggaggtac ggggtgtctt ccgagtggcc atccagcccg tgaatgacca cgcccctgtg   3060
cagaccatca gccggatctt ccatgtggcc cggggtgggc ggcggctgct gactacagac   3120
gacgtggcct tcagcgatgc tgactcgggc tttgctgacg cccagctggt gcttacccgc   3180
aaggacctcc tctttggcag tatcgtggcc gtagatgagc ccacgcggcc catctaccgc   3240
ttcacccagg aggacctcag gaagaggcga gtactgttcg tgcactcagg ggctgaccgt   3300
ggctggatcc agctgcaggt gtccgacggg caacaccagg ccactgcgct gctggaggtg   3360
caggcctcgg aaccctacct ccgtgtggcc aacggctcca gccttgtggt ccctcaagga   3420
ggccagggca ccatcgacac ggccgtgctc cacctggaca ccaacctcga catccgcagt   3480
ggggatgagg tccactacca cgtcacagct ggccctcgct ggggacagct agtccgggct   3540
ggtcagccag ccacagcctt ctcccagcag gacctgctgg atggggccgt tctctatagc   3600
cacaatggca gcctcagccc ccgcgacacc atggccttct ccgtggaagc agggccagtg   3660
cacacggatg ccaccctaca agtgaccatt gccctagagg gcccactggc cccactgaag   3720
ctggtccggc acaagaagat ctacgtcttc cagggagagg cagctgagat cagaagggac   3780
cagctggagg cagcccagga ggcagtgcca cctgcagaca tcgtattctc agtgaagagc   3840
ccaccgagtg ccggctacct ggtgatggtg tcgcgtggcg ccttggcaga tgagccaccc   3900
agcctggacc ctgtgcagag cttctcccag gaggcagtgg acacaggcag ggtcctgtac   3960
ctgcactccc gccctgaggc ctggagcgat gccttctcgc tggatgtggc ctcaggcctg   4020
ggtgctcccc tcgagggcgt ccttgtggag ctggaggtgc tgcccgctgc catccccacta   4080
gaggcgcaaa acttcagcgt ccctgagggt ggcagcctca ccctggcccc tccactgctc   4140
cgtgtctccg ggccctactt ccccactctc ctgggcctca gcctgcaggt gctggagcca   4200
ccccagcatg gagccctgca gaaggaggac ggacctcaag ccaggaccct cagcgccttc   4260
tcctggagaa tggtggaaga gcagctgatc cgctacgtgc atgacgggag cgagacactg   4320
acagacagtt ttgtcctgat ggctaatgcc tccgagatgg atcgccagag ccatcctgtg   4380
gccttcactg tcactgtcct gcctgtcaat gaccaacccc ccatcctcac tacaaacaca   4440
ggcctgcaga tgtgggaggg ggccactgcg cccatccctg cggaggctct gaggagcacg   4500
gacggcgact ctgggtctga ggatctggtc tacaccatcg agcagcccag caacgggcgg   4560
gtagtgctgc ggggggcgcc gggcactgag gtgcgcagct tcacgcaggc ccagctggac   4620
ggcgggctcg tgctgttctc acacagagga accctggatg gaggcttccg cttccgcctc   4680
tctgacggcg agcacacttc ccccggacac ttcttccgag tgacggccca gaagcaagtg   4740
ctcctctcgc tgaagggcag ccagacactg actgtctgcc cagggtccgt ccagccactc   4800
agcagtcaga ccctcagggc cagctccagc gcaggcactg acccccagct cctgctctac   4860
cgtgtggtgc ggggccccca gctaggccgg ctgttccacg cccagcagga cagcacaggg   4920
gaggccctgg tgaacttcac tcaggcagag gtctacgctg ggaatattct gtatgagcat   4980
gagatgcccc ccgagccctt ttgggaggcc catgataccc tagagctcca gctgtcctcg   5040
```

ccgcctgccc gggacgtggc cgccaccctt gctgtggctg tgtcttttga ggctgcctgt 5100
ccccagcgcc ccagccacct ctggaagaac aaaggtctct gggtccccga gggccagcgg 5160
gccaggatca ccgtggctgc tctggatgcc tccaatctct tggccagcgt tccatcaccc 5220
cagcgctcag agcatgatgt gctcttccag gtcacacagt tccccagccg gggccagctg 5280
ttggtgtccg aggagcccct ccatgctggg cagccccact tcctgcagtc ccagctggct 5340
gcagggcagc tagtgtatgc ccacggcggt gggggcaccc agcaggatgg cttccacttt 5400
cgtgcccacc tccaggggcc agcaggggcc tccgtggctg gaccccaaac ctcagaggcc 5460
tttgccatca cggtgaggga tgtaaatgag cggcccccctc agccacaggc ctctgtccca 5520
ctccggctca cccgaggctc tcgtgccccc atctcccggg cccagctgag tgtggtggac 5580
ccagactcag ctcctgggga gattgagtac gaggtccagc gggcacccca caacggcttc 5640
ctcagcctgg tgggtggtgg cctggggccc gtgacccgct tcacgcaagc cgatgtggat 5700
tcagggcggc tggccttcgt ggccaacggg agcagcgtgg caggcatctt ccagctgagc 5760
atgtctgatg ggccagccc acccctgccc atgtccctgg ctgtggacat cctaccatcc 5820
gccatcgagg tgcagctgcg ggcaccccctg gaggtgcccc aagctttggg gcgctcctca 5880
ctgagccagc agcagctccg ggtggtttca gatcgggagg agccagaggc agcataccgc 5940
ctcatccagg gaccccagta tgggcatctc ctggtgggcg ggcggcccac ctcggccttc 6000
agccaattcc agatagacca gggcgaggtg gtctttgcct tcaccaactt ctcctcctct 6060
catgaccact tcagagtcct ggcactggct aggggtgtca atgcatcagc cgtagtgaac 6120
gtcactgtga gggctctgct gcatgtgtgg gcaggtgggc catggcccca gggtgccacc 6180
ctgcgcctgg accccaccgt cctagatgct ggcgagctgg ccaaccgcac aggcagtgtg 6240
ccgcgcttcc gcctcctgga gggaccccgg catggccgcg tggtccgcgt gccccgagcc 6300
aggacggagc ccgggggcag ccagctggtg gagcagttca ctcagcagga ccttgaggac 6360
gggaggctgg ggctggaggt gggcaggcca gaggggaggg cccccggccc cgcaggtgac 6420
agtctcactc tggagctgtg ggcacagggc gtcccgcctg ctgtggcctc cctggacttt 6480
gccactgagc cttacaatgc tgcccggccc tacagcgtgg ccctgctcag tgtccccgag 6540
gccgcccgga cggaagcagg gaagccagag agcagcaccc ccacaggcga gccaggcccc 6600
atggcatcca gccctgagcc cgctgtggcc aagggaggct tcctgagctt ccttgaggcc 6660
aacatgttca gcgtcatcat ccccatgtgc ctggtacttc tgctcctggc gctcatcctg 6720
cccctgctct tctacctccg aaaacgcaac aagacgggca agcatgacgt ccaggtcctg 6780
actgccaagc cccgcaacgg cctggctggt gacaccgaga cctttcgcaa ggtggagcca 6840
ggccaggcca tcccgctcac agctgtgcct ggccaggggc cccctccagg aggccagcct 6900
gacccagagc tgctgcagtt ctgccggaca cccaaccctg cccttaagaa tggccagtac 6960
tgggtgtga 6969

<210> SEQ ID NO 3
<211> LENGTH: 375
<212> TYPE: DNA
<213> ORGANISM: Artificial Sequence
<220> FEATURE:
<223> OTHER INFORMATION: Sequence encoding the heavy chain variable
region of scFv(225.28S)

<400> SEQUENCE: 3
gccatggccc aggtgaagct gcagcagtca ggagggggct tggtgcaacc tggaggatcc 60

-continued atgaaactct cctgtgttgt ctctggattc actttcagta attactggat gaactgggtc 120
cgccagtctc cagagaaggg gcttgagtgg attgcagaaa ttagattgaa atccaataat 180
tttggaagat attatgcgga gtctgtgaaa gggaggttca ccatctcaag agatgattcc 240
aaaagtagtg cctacctgca aatgatcaac ctaagagctg aagatactgg catttattac 300
tgtaccagtt atggtaacta cgttgggcac tattttgacc actggggcca agggaccacg 360
gtcaccgtct cgagt 375

<210> SEQ ID NO 4
<211> LENGTH: 125
<212> TYPE: PRT
<213> ORGANISM: Artificial Sequence
<220> FEATURE:
<223> OTHER INFORMATION: Heavy chain variable region of scFv(225.28S)

<400> SEQUENCE: 4

```
Ala Met Ala Gln Val Lys Leu Gln Gln Ser Gly Gly Gly Leu Val Gln
1               5                   10                  15

Pro Gly Gly Ser Met Lys Leu Ser Cys Val Val Ser Gly Phe Thr Phe
            20                  25                  30

Ser Asn Tyr Trp Met Asn Trp Val Arg Gln Ser Pro Glu Lys Gly Leu
        35                  40                  45

Glu Trp Ile Ala Glu Ile Arg Leu Lys Ser Asn Asn Phe Gly Arg Tyr
    50                  55                  60

Tyr Ala Glu Ser Val Lys Gly Arg Phe Thr Ile Ser Arg Asp Asp Ser
65                  70                  75                  80

Lys Ser Ser Ala Tyr Leu Gln Met Ile Asn Leu Arg Ala Glu Asp Thr
                85                  90                  95

Gly Ile Tyr Tyr Cys Thr Ser Tyr Gly Asn Tyr Val Gly His Tyr Phe
            100                 105                 110

Asp His Trp Gly Gln Gly Thr Thr Val Thr Val Ser Ser
        115                 120                 125
```

<210> SEQ ID NO 5
<211> LENGTH: 336
<212> TYPE: DNA
<213> ORGANISM: Artificial Sequence
<220> FEATURE:
<223> OTHER INFORMATION: Sequence encoding the light chain variable region of scFv(225.28S)

<400> SEQUENCE: 5
gatatcgagc tcacccaatc tccaaaattc atgtccacat cagtaggaga cagggtcagc 60
gtcacctgca aggccagtca gaatgtggat actaatgtag cgtggtatca acaaaaacca 120
gggcaatctc ctgaaccact gcttttctcg gcatcctacc gttacactgg agtccctgat 180
cgcttcacag gcagtggatc tgggacagat ttcactctca ccatcagcaa tgtgcagtct 240
gaagacttgg cagagtattt ctgtcagcaa tataacagct atcctctgac gttcggtggc 300
ggcaccaagc tggaaatcaa acgggcggcc gcagaa 336

<210> SEQ ID NO 6
<211> LENGTH: 112
<212> TYPE: PRT
<213> ORGANISM: Artificial Sequence
<220> FEATURE:
<223> OTHER INFORMATION: Light chain variable region of scFv(225.28S)

<400> SEQUENCE: 6

```
Asp Ile Glu Leu Thr Gln Ser Pro Lys Phe Met Ser Thr Ser Val Gly
1               5                   10                  15

Asp Arg Val Ser Val Thr Cys Lys Ala Ser Gln Asn Val Asp Thr Asn
            20                  25                  30

Val Ala Trp Tyr Gln Gln Lys Pro Gly Gln Ser Pro Glu Pro Leu Leu
        35                  40                  45

Phe Ser Ala Ser Tyr Arg Tyr Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Leu
                85                  90                  95

Thr Phe Gly Gly Gly Thr Lys Leu Glu Ile Lys Arg Ala Ala Ala Glu
            100                 105                 110


<210> SEQ ID NO 7
<211> LENGTH: 550
<212> TYPE: PRT
<213> ORGANISM: Artificial Sequence
<220> FEATURE:
<223> OTHER INFORMATION: Heavy chain of chimeric anti-HMW-MAA IgE
      antibody

<400> SEQUENCE: 7

Gln Val Lys Leu Gln Gln Ser Gly Gly Gly Leu Val Gln Pro Gly Gly
1               5                   10                  15

Ser Met Lys Leu Ser Cys Val Val Ser Gly Phe Thr Phe Ser Asn Tyr
            20                  25                  30

Trp Met Asn Trp Val Arg Gln Ser Pro Glu Lys Gly Leu Glu Trp Ile
        35                  40                  45

Ala Glu Ile Arg Leu Lys Ser Asn Asn Phe Gly Arg Tyr Tyr Ala Glu
    50                  55                  60

Ser Val Lys Gly Arg Phe Thr Ile Ser Arg Asp Asp Ser Lys Ser Ser
65                  70                  75                  80

Ala Tyr Leu Gln Met Ile Asn Leu Arg Ala Glu Asp Thr Gly Ile Tyr
                85                  90                  95

Tyr Cys Thr Ser Tyr Gly Asn Tyr Val Gly His Tyr Phe Asp His Trp
            100                 105                 110

Gly Gln Gly Thr Thr Val Thr Val Ser Ser Ala Ser Thr Gln Ser Pro
        115                 120                 125

Ser Val Phe Pro Leu Thr Arg Cys Cys Lys Asn Ile Pro Ser Asn Ala
    130                 135                 140

Thr Ser Val Thr Leu Gly Cys Leu Ala Thr Gly Tyr Phe Pro Glu Pro
145                 150                 155                 160

Val Met Val Thr Trp Asp Thr Gly Ser Leu Asn Gly Thr Thr Met Thr
                165                 170                 175

Leu Pro Ala Thr Thr Leu Thr Leu Ser Gly His Tyr Ala Thr Ile Ser
            180                 185                 190

Leu Leu Thr Val Ser Gly Ala Trp Ala Lys Gln Met Phe Thr Cys Arg
        195                 200                 205

Val Ala His Thr Pro Ser Ser Thr Asp Trp Val Asp Asn Lys Thr Phe
    210                 215                 220

Ser Val Cys Ser Arg Asp Phe Thr Pro Pro Thr Val Lys Ile Leu Gln
225                 230                 235                 240

Ser Ser Cys Asp Gly Gly Gly His Phe Pro Pro Thr Ile Gln Leu Leu
```

```
                245                 250                 255

Cys Leu Val Ser Gly Tyr Thr Pro Gly Thr Ile Asn Ile Thr Trp Leu
            260                 265                 270

Glu Asp Gly Gln Val Met Asp Val Asp Leu Ser Thr Ala Ser Thr Thr
        275                 280                 285

Gln Glu Gly Glu Leu Ala Ser Thr Gln Ser Glu Leu Thr Leu Ser Gln
    290                 295                 300

Lys His Trp Leu Ser Asp Arg Thr Tyr Thr Cys Gln Val Thr Tyr Gln
305                 310                 315                 320

Gly His Thr Phe Glu Asp Ser Thr Lys Lys Cys Ala Asp Ser Asn Pro
                325                 330                 335

Arg Gly Val Ser Ala Tyr Leu Ser Arg Pro Ser Pro Phe Asp Leu Phe
            340                 345                 350

Ile Arg Lys Ser Pro Thr Ile Thr Cys Leu Val Val Asp Leu Ala Pro
        355                 360                 365

Ser Lys Gly Thr Val Asn Leu Thr Trp Ser Arg Ala Ser Gly Lys Pro
    370                 375                 380

Val Asn His Ser Thr Arg Lys Glu Glu Lys Gln Arg Asn Gly Thr Leu
385                 390                 395                 400

Thr Val Thr Ser Thr Leu Pro Val Gly Thr Arg Asp Trp Ile Glu Gly
                405                 410                 415

Glu Thr Tyr Gln Cys Arg Val Thr His Pro His Leu Pro Arg Ala Leu
            420                 425                 430

Met Arg Ser Thr Thr Lys Thr Ser Gly Pro Arg Ala Ala Pro Glu Val
        435                 440                 445

Tyr Ala Phe Ala Thr Pro Glu Trp Pro Gly Ser Arg Asp Lys Arg Thr
    450                 455                 460

Leu Ala Cys Leu Ile Gln Asn Phe Met Pro Glu Asp Ile Ser Val Gln
465                 470                 475                 480

Trp Leu His Asn Glu Val Gln Leu Pro Asp Ala Arg His Ser Thr Thr
                485                 490                 495

Gln Pro Arg Lys Thr Lys Gly Ser Gly Phe Phe Val Phe Ser Arg Leu
            500                 505                 510

Glu Val Thr Arg Ala Glu Trp Glu Gln Lys Asp Glu Phe Ile Cys Arg
        515                 520                 525

Ala Val His Glu Ala Ala Ser Pro Ser Gln Thr Val Gln Arg Ala Val
    530                 535                 540

Ser Val Asn Pro Gly Lys
545                 550


<210> SEQ ID NO 8
<211> LENGTH: 214
<212> TYPE: PRT
<213> ORGANISM: Artificial Sequence
<220> FEATURE:
<223> OTHER INFORMATION: Light chain of chimeric anti-HMW-MAA IgE
      antibody

<400> SEQUENCE: 8

Asp Ile Glu Leu Thr Gln Ser Pro Lys Phe Met Ser Thr Ser Val Gly
1               5                   10                  15

Asp Arg Val Ser Val Thr Cys Lys Ala Ser Gln Asn Val Asp Thr Asn
            20                  25                  30

Val Ala Trp Tyr Gln Gln Lys Pro Gly Gln Ser Pro Glu Pro Leu Leu
        35                  40                  45
```

-continued

```
Phe Ser Ala Ser Tyr Arg Tyr Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Leu
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 9
<211> LENGTH: 1653
<212> TYPE: DNA
<213> ORGANISM: Artificial Sequence
<220> FEATURE:
<223> OTHER INFORMATION: Sequence encoding the heavy chain of chimeric anti-HMW-MAA IgE antibody

<400> SEQUENCE: 9

```
caagtcaaac tgcagcagag cggtggaggc ctggtgcagc ctggtggcag catgaagctg     60

agctgcgtcg tgagcggctt caccttcagc aactactgga tgaactgggt ccggcagagc    120

cccgagaagg gcctggaatg gatcgccgag atccggctga aaagcaacaa cttcggccgg    180

tactacgccg agagcgtgaa gggccggttc accatcagcc gggacgacag caagagcagc    240

gcctacctgc agatgatcaa cctgcgggcc gaggacaccg gcatctacta ctgcaccagc    300

tacggcaact acgtgggcca ctacttcgac cactggggcc agggcaccac cgtgactgtc    360

agcagcgcta gcacacagag cccatccgtc ttccccttga cccgctgctg caaaaacatt    420

ccctccaatg ccacctccgt gactctgggc tgcctggcca cgggctactt cccggagccg    480

gtgatggtga cctgggacac aggctccctc aacgggacaa ctatgacctt accagccacc    540

accctcacgc tctctggtca ctatgccacc atcagcttgc tgaccgtctc gggtgcgtgg    600

gccaagcaga tgttcacctg ccgtgtggca cacactccat cgtccacaga ctgggtcgac    660

aacaaaacct tcagcgtctg ctccagggac ttcaccccgc ccaccgtgaa gatcttacag    720

tcgtcctgcg acggcggcgg gcacttcccc ccgaccatcc agctcctgtg cctcgtctct    780

gggtacaccc cagggactat caacatcacc tggctggagg acgggcaggt catggacgtg    840

gacttgtcca ccgcctctac cacgcaggag ggtgagctgg cctccacaca aagcgagctc    900

accctcagcc agaagcactg gctgtcagac cgcacctaca cctgccaggt cacctatcaa    960

ggtcacacct ttgaggacag caccaagaag tgtgcagatt ccaacccgag aggggtgagc   1020

gcctacctaa gccggcccag cccgttcgac ctgttcatcc gcaagtcgcc cacgatcacc   1080
```

```
tgtctggtgg tggacctggc acccagcaag gggaccgtga acctgacctg gtcccgggcc   1140

agtgggaagc ctgtgaacca ctccaccaga aaggaggaga agcagcgcaa tggcacgtta   1200

accgtcacgt ccaccctgcc ggtgggcacc cgagactgga tcgaggggga gacctaccag   1260

tgcagggtga cccacccccca cctgcccagg gccctcatgc ggtccacgac caagaccagc   1320

ggcccgcgtg ctgccccgga agtctatgcg tttgcgacgc cggagtggcc ggggagccgg   1380

gacaagcgca ccctcgcctg cctgatccag aacttcatgc ctgaggacat ctcggtgcag   1440

tggctgcaca acgaggtgca gctcccggac gcccggcaca gcacgacgca gccccgcaag   1500

accaagggct ccggcttctt cgtcttcagc cgcctggagg tgaccagggc cgaatgggag   1560

cagaaagatg agttcatctg ccgtgcagtc catgaggcag cgagcccctc acagaccgtc   1620

cagcgagcgg tgtctgtaaa tcccggtaaa tga                                1653
```

<210> SEQ ID NO 10
<211> LENGTH: 645
<212> TYPE: DNA
<213> ORGANISM: Artificial Sequence
<220> FEATURE:
<223> OTHER INFORMATION: Sequence encoding the light chain of chimeric anti-HMW-MAA IgE antibody

<400> SEQUENCE: 10

```
gacatcgagc tgacccagag ccccaagttc atgagcacca gcgtgggcga cagagtgtcc     60

gtgacctgca aggccagcca gaacgtggac accaacgtgg cctggtatca gcagaagccc    120

ggccagagcc ctgagcctct gctgttcagc gccagctaca gatacaccgg cgtgcccgac    180

agattcacag gcagcggctc cggcaccgac ttcaccctga ccatcagcaa cgtgcagagc    240

gaggacctgg ccgagtactt ctgccagcag tacaacagct accccctgac cttcggcgga    300

ggcaccaagc tggaaatcaa gcgtacggtg gcggcgccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gttag                    645
```

<210> SEQ ID NO 11
<211> LENGTH: 367
<212> TYPE: DNA
<213> ORGANISM: Artificial Sequence
<220> FEATURE:
<223> OTHER INFORMATION: Sequence comprising human codon optimisations, encoding the heavy chain variable region of chimeric anti-HMW-MAA IgE antibody

<400> SEQUENCE: 11

```
caagtcaaac tgcagcagag cggtggaggc ctggtgcagc ctggtggcag catgaagctg     60

agctgcgtcg tgagcggctt caccttcagc aactactgga tgaactgggt ccggcagagc    120

cccgagaagg gcctggaatg gatcgccgag atccggctga aaagcaacaa cttcggccgg    180

tactacgccg agagcgtgaa gggccggttc accatcagcc gggacgacag caagagcagc    240

gcctacctgc agatgatcaa cctgcgggcc gaggacaccg gcatctacta ctgcaccagc    300

tacggcaact acgtgggcca ctacttcgac cactggggcc agggcaccac cgtgactgtc    360

agcagcg                                                              367
```

<210> SEQ ID NO 12
<211> LENGTH: 322
<212> TYPE: DNA
<213> ORGANISM: Artificial Sequence
<220> FEATURE:
<223> OTHER INFORMATION: Sequence comprising human codon optimisations, encoding the light chain variable region of chimeric anti-HMW-MAA IgE antibody

<400> SEQUENCE: 12
gacatcgagc tgacccagag ccccaagttc atgagcacca gcgtgggcga cagagtgtcc 60
gtgacctgca aggccagcca gaacgtggac accaacgtgg cctggtatca gcagaagccc 120
ggccagagcc ctgagcctct gctgttcagc gccagctaca gatacaccgg cgtgcccgac 180
agattcacag gcagcggctc cggcaccgac ttcaccctga ccatcagcaa cgtgcagagc 240
gaggacctgg ccgagtactt ctgccagcag tacaacagct accccctgac cttcggcgga 300
ggcaccaagc tggaaatcaa gc 322

<210> SEQ ID NO 13
<211> LENGTH: 309
<212> TYPE: DNA
<213> ORGANISM: Artificial Sequence
<220> FEATURE:
<223> OTHER INFORMATION: Sequence encoding human immunoglobulin heavy chain constant domain CH(epsilon)1

<400> SEQUENCE: 13
ctagcacaca gagcccatcc gtcttcccct tgacccgctg ctgcaaaaac attccctcca 60
atgccacctc cgtgactctg ggctgcctgg ccacgggcta cttcccggag ccggtgatgg 120
tgacctggga cacaggctcc ctcaacggga caactatgac cttaccagcc accaccctca 180
cgctctctgg tcactatgcc accatcagct tgctgaccgt ctcgggtgcg tgggccaagc 240
agatgttcac ctgccgtgtg gcacacactc catcgtccac agactgggtc gacaacaaaa 300
ccttcagcg 309

<210> SEQ ID NO 14
<211> LENGTH: 321
<212> TYPE: DNA
<213> ORGANISM: Artificial Sequence
<220> FEATURE:
<223> OTHER INFORMATION: Sequence encoding human immunoglobulin heavy chain constant domain CH(epsilon)2

<400> SEQUENCE: 14
tctgctccag ggacttcacc ccgcccaccg tgaagatctt acagtcgtcc tgcgacggcg 60
gcgggcactt ccccccgacc atccagctcc tgtgcctcgt ctctgggtac accccaggga 120
ctatcaacat cacctggctg gaggacgggc aggtcatgga cgtggacttg tccaccgcct 180
ctaccacgca ggagggtgag ctggcctcca cacaaagcga gctcaccctc agccagaagc 240
actggctgtc agaccgcacc tacacctgcc aggtcaccta tcaaggtcac acctttgagg 300
acagcaccaa gaagtgtgca g 321

<210> SEQ ID NO 15
<211> LENGTH: 324
<212> TYPE: DNA
<213> ORGANISM: Artificial Sequence
<220> FEATURE:
<223> OTHER INFORMATION: Sequence encoding human immunoglobulin heavy chain constant domain CH(epsilon)3

<400> SEQUENCE: 15
attccaaccc gagaggggtg agcgcctacc taagccggcc cagcccgttc gacctgttca 60
tccgcaagtc gcccacgatc acctgtctgg tggtggacct ggcacccagc aaggggaccg 120
tgaacctgac ctggtcccgg gccagtggga agcctgtgaa ccactccacc agaaaggagg 180
agaagcagcg caatggcacg ttaaccgtca cgtccaccct gccggtgggc acccgagact 240
ggatcgaggg ggagacctac cagtgcaggg tgacccaccc ccacctgccc agggccctca 300
tgcggtccac gaccaagacc agcg 324

<210> SEQ ID NO 16
<211> LENGTH: 332
<212> TYPE: DNA
<213> ORGANISM: Artificial Sequence
<220> FEATURE:
<223> OTHER INFORMATION: Sequence encoding human immunoglobulin heavy
chain constant domain CH(epsilon)4

<400> SEQUENCE: 16
gcccgcgtgc tgccccggaa gtctatgcgt ttgcgacgcc ggagtggccg gggagccggg 60
acaagcgcac cctcgcctgc ctgatccaga acttcatgcc tgaggacatc tcggtgcagt 120
ggctgcacaa cgaggtgcag ctcccggacg cccggcacag cacgacgcag ccccgcaaga 180
ccaagggctc cggcttcttc gtcttcagcc gcctggaggt gaccagggcc gaatgggagc 240
agaaagatga gttcatctgc cgtgcagtcc atgaggcagc gagcccctca cagaccgtcc 300
agcgagcggt gtctgtaaat cccggtaaat ga 332

<210> SEQ ID NO 17
<211> LENGTH: 323
<212> TYPE: DNA
<213> ORGANISM: Artificial Sequence
<220> FEATURE:
<223> OTHER INFORMATION: Sequence encoding human light chain constant
domain

<400> SEQUENCE: 17
gtacggtggc ggcgccatct gtcttcatct tcccgccatc tgatgagcag ttgaaatctg 60
gaactgcctc tgttgtgtgc ctgctgaata acttctatcc cagagaggcc aaagtacagt 120
ggaaggtgga taacgccctc caatcgggta actcccagga gagtgtcaca gagcaggaca 180
gcaaggacag cacctacagc ctcagcagca ccctgacgct gagcaaagca gactacgaga 240
aacacaaagt ctacgcctgc gaagtcaccc atcagggcct gagctcgccc gtcacaaaga 300
gcttcaacag gggagagtgt tag 323

<210> SEQ ID NO 18
<211> LENGTH: 8
<212> TYPE: PRT
<213> ORGANISM: Artificial Sequence
<220> FEATURE:
<223> OTHER INFORMATION: Heavy chain CDR sequence

<400> SEQUENCE: 18

Gly Phe Thr Phe Ser Asn Tyr Trp
1 5

<210> SEQ ID NO 19
<211> LENGTH: 10
<212> TYPE: PRT
<213> ORGANISM: Artificial Sequence -continued
<220> FEATURE:
<223> OTHER INFORMATION: Heavy chain CDR sequence

<400> SEQUENCE: 19

Ile Arg Leu Lys Ser Asn Asn Phe Gly Arg
1               5                   10

<210> SEQ ID NO 20
<211> LENGTH: 13
<212> TYPE: PRT
<213> ORGANISM: Artificial Sequence
<220> FEATURE:
<223> OTHER INFORMATION: Heavy chain CDR sequence

<400> SEQUENCE: 20

Thr Ser Tyr Gly Asn Tyr Val Gly His Tyr Phe Asp His
1               5                   10

<210> SEQ ID NO 21
<211> LENGTH: 6
<212> TYPE: PRT
<213> ORGANISM: Artificial Sequence
<220> FEATURE:
<223> OTHER INFORMATION: Light chain CDR sequence

<400> SEQUENCE: 21

Gln Asn Val Asp Thr Asn
1               5

<210> SEQ ID NO 22
<211> LENGTH: 3
<212> TYPE: PRT
<213> ORGANISM: Artificial Sequence
<220> FEATURE:
<223> OTHER INFORMATION: Light chain CDR sequence

<400> SEQUENCE: 22

Ser Ala Ser
1

<210> SEQ ID NO 23
<211> LENGTH: 9
<212> TYPE: PRT
<213> ORGANISM: Artificial Sequence
<220> FEATURE:
<223> OTHER INFORMATION: Light chain CDR sequence

<400> SEQUENCE: 23

Gln Gln Tyr Asn Ser Tyr Pro Leu Thr
1               5

<210> SEQ ID NO 24
<211> LENGTH: 122
<212> TYPE: PRT
<213> ORGANISM: Artificial Sequence
<220> FEATURE:
<223> OTHER INFORMATION: Heavy chain variable domain of mAB 225.28S

<400> SEQUENCE: 24

Gln Val Lys Leu Gln Gln Ser Gly Gly Gly Leu Val Gln Pro Gly Gly
1               5                   10                  15

Ser Met Lys Leu Ser Cys Val Val Ser Gly Phe Thr Phe Ser Asn Tyr
            20                  25                  30

Trp Met Asn Trp Val Arg Gln Ser Pro Glu Lys Gly Leu Glu Trp Ile
        35                  40                  45

-continued

```
Ala Glu Ile Arg Leu Lys Ser Asn Asn Phe Gly Arg Tyr Tyr Ala Glu
    50                  55                  60

Ser Val Lys Gly Arg Phe Thr Ile Ser Arg Asp Asp Ser Lys Ser Ser
65                  70                  75                  80

Ala Tyr Leu Gln Met Ile Asn Leu Arg Ala Glu Asp Thr Gly Ile Tyr
                85                  90                  95

Tyr Cys Thr Ser Tyr Gly Asn Tyr Val Gly His Tyr Phe Asp His Trp
            100                 105                 110

Gly Gln Gly Thr Thr Val Thr Val Ser Ser
        115                 120


<210> SEQ ID NO 25
<211> LENGTH: 367
<212> TYPE: DNA
<213> ORGANISM: Artificial Sequence
<220> FEATURE:
<223> OTHER INFORMATION: Sequence encoding the heavy chain variable
      domain of scFv(225.28S)

<400> SEQUENCE: 25

caagtcaaac tgcagcagag cggtggaggc ctggtgcagc ctggtggcag catgaagctg      60

agctgcgtcg tgagcggctt caccttcagc aactactgga tgaactgggt ccggcagagc     120

cccgagaagg gcctggaatg gatcgccgag atccggctga aaagcaacaa cttcggccgg     180

tactacgccg agagcgtgaa gggccggttc accatcagcc gggacgacag caagagcagc     240

gcctacctgc agatgatcaa cctgcgggcc gaggacaccg gcatctacta ctgcaccagc     300

tacggcaact acgtgggcca ctacttcgac cactggggcc agggcaccac cgtgactgtc     360

agcagcg                                                               367


<210> SEQ ID NO 26
<211> LENGTH: 4
<212> TYPE: PRT
<213> ORGANISM: Artificial Sequence
<220> FEATURE:
<223> OTHER INFORMATION: Partial sequence from chimeric anti-HMW-MAA IgE
      antibody

<400> SEQUENCE: 26

Tyr Ala Thr His
1


<210> SEQ ID NO 27
<211> LENGTH: 107
<212> TYPE: PRT
<213> ORGANISM: Artificial Sequence
<220> FEATURE:
<223> OTHER INFORMATION: Light chain variable domain of mAB 225.28S

<400> SEQUENCE: 27

Asp Ile Glu Leu Thr Gln Ser Pro Lys Phe Met Ser Thr Ser Val Gly
1               5                   10                  15

Asp Arg Val Ser Val Thr Cys Lys Ala Ser Gln Asn Val Asp Thr Asn
            20                  25                  30

Val Ala Trp Tyr Gln Gln Lys Pro Gly Gln Ser Pro Glu Pro Leu Leu
        35                  40                  45

Phe Ser Ala Ser Tyr Arg Tyr Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80
```

-continued

```
Glu Asp Leu Ala Glu Tyr Phe Cys Gln Gln Tyr Asn Ser Tyr Pro Leu
                85                  90                  95

Thr Phe Gly Gly Gly Thr Lys Leu Glu Ile Lys
            100                 105


<210> SEQ ID NO 28
<211> LENGTH: 322
<212> TYPE: DNA
<213> ORGANISM: Artificial Sequence
<220> FEATURE:
<223> OTHER INFORMATION: Sequence encoding the light chain variable
      domain of mAB 225.28S

<400> SEQUENCE: 28

gacatcgagc tgacccagag ccccaagttc atgagcacca gcgtgggcga cagagtgtcc      60

gtgacctgca aggccagcca gaacgtggac accaacgtgg cctggtatca gcagaagccc     120

ggccagagcc ctgagcctct gctgttcagc gccagctaca gatacaccgg cgtgcccgac     180

agattcacag gcagcggctc cggcaccgac ttcaccctga ccatcagcaa cgtgcagagc     240

gaggacctgg ccgagtactt ctgccagcag tacaacagct accccctgac cttcggcgga     300

ggcaccaagc tggaaatcaa gc                                              322
```